US008697367B2

(12) United States Patent
Buhimschi et al.

(10) Patent No.: US 8,697,367 B2
(45) Date of Patent: Apr. 15, 2014

(54) MARKERS FOR DETECTION OF COMPLICATIONS RESULTING FROM IN UTERO ENCOUNTERS

(75) Inventors: Catalin S. Buhimschi, New Haven, CT (US); Irina Buhimschi, New Haven, CT (US); Vineet Bhandari, Cheshire, CT (US)

(73) Assignee: Yale University, New Haven, CT (US)

( * ) Notice: Subject to any disclaimer, the term of this patent is extended or adjusted under 35 U.S.C. 154(b) by 73 days.

(21) Appl. No.: 13/193,421

(22) Filed: Jul. 28, 2011

(65) Prior Publication Data

US 2012/0021442 A1 Jan. 26, 2012

Related U.S. Application Data

(63) Continuation-in-part of application No. PCT/US2010/000259, filed on Jan. 28, 2010.

(60) Provisional application No. 61/206,125, filed on Jan. 28, 2009.

(51) Int. Cl.
*G01N 33/53* (2006.01)

(52) U.S. Cl.
USPC .......................................... 435/7.1

(58) Field of Classification Search
None
See application file for complete search history.

(56) References Cited

U.S. PATENT DOCUMENTS

2007/0161125 A1 7/2007 Rosenfeld et al.

FOREIGN PATENT DOCUMENTS

WO WO 2008/046160 A1 4/2008

OTHER PUBLICATIONS

Buhimschi et al., "Comprehensive Proteomic Mapping of Cord Blood to Identify Novel Biomarkers and Functional Protein Networks Characteristic of Early Onset Neonatal Sepsis (EONS)," *American Journal of Obstetrics and Gynecology* 199(6):S3 (2008).
Buhimschi et al., "504: Significance of Early Haptoglobin (HP) Switching-on, Levels and Phenotypes in Preterm Newborns with Early Onset Neonatal Sepsis (EONS)," *American Journal of Obstetrics and Gynecology* 201(6):S188-S189 (2009).
Kalayci et al., "The Importance of Fibronectin, Haptolglobin, Ceruloplasmin and Transferrin in the Early Diagnosis of Neonatal Sepsis," *Turk J. Med. Sci.* 30:151-155 (2000).

*Primary Examiner* — Michael Pak
(74) *Attorney, Agent, or Firm* — Wolf, Greenfield & Sacks, P.C.

(57) ABSTRACT

Described herein are biomarkers, such as protein biomarkers, which are diagnostic of and predictive for complications that result from an in utero encounter, such as an infection by the fetus, that can lead to premature birth (PTB). The biomarkers can be used to identify fetuses and newborns at risk for complications of PTB, such as (Early Onset Neonatal Sepsis) EONS, intra-ventricular hemorrhage (IVH) and other poor outcomes.

8 Claims, 24 Drawing Sheets

PROTEOMICS STUDY DESIGN

- Proteomics techniques
  2D-DIGE after albumin & IgG depletion
  Robotic tryptic digests
  Tandem mass spectrometry
  PANTHER ontological classification

- Validation phase
  Immunoassays (n=155)
  Western blot

Figure 3

RESULTS

| Maternal and neonatal characteristics | EONS | |
|---|---|---|
| Median [IQ range] | NO (n=115) | YES (n=40) |
| GA at delivery (wks) | 30 [28 – 33] | 26 [25 – 30] |
| Birthweight (g) | 1,450 [1,121 – 1,985] | 920 [750 – 1,407] |
| Apgar - 1 min | 8 [5 – 9] | 5 [2 – 7] |
| Apgar - 5 min | 9 [8 – 9] | 8 [6 – 8] |
| Umbilical artery pH | 7.32 [7.2 – 7.4] | 7.33 [7.3 – 7.4] |
| Umbilical artery base deficit | 4.4 [3.2 – 5.5] | 5.1 [3.1 – 7.5] |

Figure 4

NEONATAL SEPSIS

| Hematological indices and microbiological studies | EONS NO (n=115) | EONS YES (n=40) |
|---|---|---|
| *Median [IQ range]* | | |
| Differential WBC count | | |
| Hematocrit (%) | 47 [42 - 52] | 43 [39 - 47] |
| Lymphocytes (%) | 44 [32 - 58] | 29 [23 - 44] |
| Hematologic indices | | |
| ABC (cells/mm3) | 310 [130 - 677] | 2,592 [1,557 - 3,795] |
| I:T ratio (%) | 4 [1 - 6] | 19 [14 - 25] |
| Microbiologic studies | | |
| Positive blood cultures: n (%) | 0 (0) | 8 (20) |

Figure 6

POTENTIAL PROTEIN BIOMARKERS

| Biomarkers | 2D-DIGE Fold change | P-value Immunoassay |
|---|---|---|
| *Down-regulated* | | |
| Apolipoprotein H | -1 | ns |
| Apolipoprotein E | -3 | ns |
| Vitamin D binding protein | -3 | ns |
| *Up-regulated* | | |
| Haptoglobin | 32 | |
| Haptoglobin-related protein | 60 | < 0.001 |

Figure 9

MARKERS FOR DETECTION OF COMPLICATIONS RESULTING FROM IN UTERO ENCOUNTERS

RELATED APPLICATION

This application is a continuation-in-part of PCT/US2010/000259 filed Jan. 28, 2010, which claims the benefit of the filing date of U.S. Provisional application 61/206,125, entitled "Novel biomarkers for detection of early onset neonatal sepsis (EONS) and other complications of prematurity" and filed Jan. 28, 2009. The entire teachings of the referenced applications are incorporated herein by reference.

GOVERNMENT FUNDING

This invention was made with government support under Grant Number R01 HD047321 and R01HD062007-01, awarded by the National Institutes of Health. The government has certain rights in the invention.

BACKGROUND OF THE INVENTION

Premature birth (PTB) is a significant public health problem. The technological advances in newborn intensive care of the past decades have increased survival of preterm infants and the awareness of the need to improve outcomes. Infection-induced PTB represents a unique environment, given that attempts to prolong pregnancy raise the risk for early onset neonatal sepsis (EONS). In such cases, there is an increased risk of poor neonatal outcomes, including intraventricular hemorrhage (IVH), which is a significant cause of brain injury, cerebral palsy and developmental disability. A key problem is that most hemorrhages occur in the first 24 hours and therapies aimed to prevent IVH must address the complexity of this condition. In 2001 the World Health Organization established the external Child Health Epidemiology Reference Group (CHERG) to develop epidemiological estimates for the various etiologies of death in young children.[1] In 2003, building on the work of CHERG, it was established that prematurity accounts for 75% of infant mortality and 10% of the 10.6 million yearly deaths in children younger than five years.[1] The latest U.S. vital statistics (2007) report a 12.7% rate of PTB.[2] Compared to 1990, the percentage of infants delivered <37 completed weeks of gestation has climbed 20%, resulting in ~550,000 premature infants born annually; 60,000 of them have a birthweight <1,500 grams. As support in the NBSCU has improved, more low- and very-low-birth weight (VLBW) infants survive. It has thus become clear that improving neonatal outcomes associated with prematurity is vital.[3,4] About 5% of the nearly 55,000 preemies who survive the newborn period exhibit cerebral palsy and up to 25-50% have sensorial, cognitive and behavioral deficits which include mental retardation, visual and hearing impairments, learning and language disabilities, attention deficit-hyperactivity disorder, motor coordination defects, behavioral, emotional and social difficulties. The immediate impact of PTB for society is underscored by the rising costs of caring for premature infants which in 2005 was estimated in the US in excess of $26 billion/year. This figure does not include rehabilitation or long-term care costs.[5] Even more concerning have been the recent childhood outcome results of studies aimed at preventing PTB by universally extending pregnancy. The results of ORACLE I & II clinical trials, released in 2008, show that antibiotics given to women in preterm labor and PPROM to increase the duration of gestation also increased the risk of cerebral palsy.[6,7] The underlying mechanisms remain unclear, but this data highlights the need for a paradigm shift in prematurity research from the unilateral goal of extending the duration of gestation to concurrently improving neonatal outcomes. Concerned by these issues and the alarming increase in the rate of PTB, the March of Dimes Scientific Advisory Committee on Prematurity[8] and the most recent report issued by the Institute of Medicine in 2008: Preterm Birth: Causes, Consequences and Prevention suggested that studies to identify biomarkers that may predict adverse outcomes for infants born preterm to allow for early intervention should become a priority.[9] Clearly, additional approaches to assessing neonatal and early postnatal risk independent of gestational age (GA), and particularly approaches that can provide an early diagnosis, are needed.

SUMMARY OF THE INVENTION

Described herein are biomarkers, such as protein biomarkers, which are diagnostic of and predictive for complications that result from an in utero encounter, such as an infection (e.g., bacterial, viral, parasitic or fungal), by the fetus. The biomarkers described herein are useful in methods of predicting fetal and neonatal outcome and can be assessed, for example, in cord blood (CB), in blood or in other body fluids obtained from the neonate/newborn. In some embodiments, the biomarkers can be assessed in fetal blood from the umbilical cord, for example, by cordocentesis a procedure sometimes called Percutaneous Umbilical Cord Blood Sampling (PUBS).

A specific embodiment described herein relates to protein biomarkers, originally identified in cord blood, that are diagnostic of and predictive for Early Onset Neonatal Sepsis (EONS). The risk of EONS increases when a pregnant woman is treated in an attempt to prolong pregnancy (to avoid PTB), such as in cases in which intrauterine infection occurs. As described herein, levels of biomarkers in cord blood samples from newborns who subsequently developed EONS were increased or decreased by 3-fold or more (at least three-fold), compared to controls. Newborns matched for gestational age (GA), low cord blood (CB) CB IL-6 (about 9 pg/mL) and delivered in the setting of idiopathic PTB or cord blood from a group of term babies with uncomplicated pregnancy and delivery may serve as negative controls. These groups may serve to establish the methodological baseline or reference point. Alternatively, a control or reference can be a premature neonate who progressed to EONS and/or at least one related complication of prematurity (preterm birth).

Also described herein is a rapid and relevant screening test that can be used at birth to identify neonates (newborns) at risk for intra ventricular hemorrhage (IVH) and other poor outcomes associated with premature birth. The screening test may also be performed before birth, e.g., by cordocentesis, or at any time after birth, preferably within the first 24 hours, 48 hours or 72 hours (within 1 day, 2 days or 3 days) after birth. The biomarkers described herein can also be used as markers for adverse outcomes associated with premature birth, regardless of the cause of PTB.

There are many complications that can occur as a result of PTB, only one of which is EONS. Conventionally, EONS is defined as a positive microbial culture in the first 72 hours of life. However, due to widespread use of antibiotics, culture results are frequently unreliable and diagnosis of EONS relies on clinical signs, combined with hematological and serological markers, which are non-specific. Culture results can be unreliable e.g., due to "difficult-to-cultivate" bacteria or because of the use of antibiotics to treat the mother, which may lead to false-negative diagnoses. Contamination, e.g. by personnel handling the samples, may lead to false positive results. Discovery of biomarkers that make it possible to diagnose complication(s) of PTB or predict that complication(s) of PTB will develop in a newborn or infant are critically needed. The method of screening described herein has made it possible to diagnose complication(s) of PTB and/or predict whether (predict the future development of, predict increased risk of) complication(s) of PTB will develop; it can be used at birth and in newborns to identify those at risk for complications of PTB, such as EONS, IVH and other poor outcomes. Prompt initiation of postnatal pharmacologic intervention strategies for IVH could result in health care savings of over 3 billion dollars/year.

As described herein, Applicant has shown that expression of haptoglobin (Hp) and/or haptoglobin-related protein (HpRP) switches on precociously in newborns who develop EONS. The quantitative and qualitative changes in Hp and/or HpRP expression provide the basis for predicting newborns at risk for EONS, IVH, other complications and/or death and for providing targeted interventions at birth.

Hp is an immunomodulatory protein linked to human susceptibility, as opposed to resistance, to infection. Two allelic variants (Hp1 and Hp2) in humans code proteins with different α-chains. As a result of developmental regulation of Hp transcription, Hp is essentially absent at birth and the adult phenotype (Hp1-1; Hp2-1 or Hp2-2) emerges within the first year of life. The Hp0-0 phenotype lacks both alleles. HpRP shares greater than 90% homology with Hp. As described herein, Applicant has carried out characterization of the cord blood proteome and shown that Hp is a biomarker of EONS. As also described herein, Hp phenotype variations and levels are critical determinants of susceptibility to adverse neonatal outcomes.

Applicant, without wishing to be bound by any particular theory, considers EONS to be a heterogeneous syndrome, rather than a single condition, and describes here four possible EONS variants, each of which would benefit from a different therapeutic ("theranostics") approach. These variants are as follows:

EONS I: Vertical transmission of live bacteria to the fetus, which would require prompt identification and targeted antibiotic treatment.

EONS II: Translocation of bacterial footprints (e.g., endotoxin) and damage-associated molecular pattern proteins (DAMPs) from the mother and damaged placenta to the fetus. This would require general cardio-vascular support, anti-inflammatory treatment and specific endotoxin neutralizing strategies.

EONS III: Translocation of cytokines (such as IL-6) from the mother and damaged placenta to the fetus. Treatment would include circulatory support and/or anti-inflammatory treatment.

EONS 0: None of the above, in the context of prematurity often leading to over-treatment.

Also described herein is a method of distinguishing among the variants of EONS and a method of determining which variant a neonate exhibits (determining which class or variant type a neonate falls into) and, further, determining whether therapy is needed and, if therapy is needed, the type(s) of appropriate therapy for the neonate. Such a method will result in more targeted therapy for newborns who exhibit EONS I, II, or III and avoid or reduce the use of unnecessary treatments for newborns who exhibit EONS 0.

In one embodiment, such a method for early diagnosis and pathogenic classification of EONS comprises at least one (a, one or more), at least two (two or more), at least three (three or more), at least four (four or more), or five of the following elements:

(a) Cord blood Hp and HpRP switching (antenatal switching), represented qualitatively as positive or negative and derived from an assessment of Hp and HpRP in cord blood, as assessed for example, by Hp and/or HpRP immunoreactivity above an established cut-off;

(b) Cord blood Hp and HpRP level represented quantitatively as the level of Hp and HpRP immunoreactivity;

(c) Cord blood Hp and HpRP phenotype, which is Hp 0-0, Hp 1-1, 1-2 or 2-2;

(d) Relationship of cord blood Hp and HpRP level with cord blood IL-6;

(e) Relationship of cord blood Hp and HpRP level and cord blood IL-6 with bacterial fingerprints.

In certain embodiments, methods are provided for early diagnosis and pathogenic classifications of EONS based on (a) Hp and HpRP switching represented qualitatively as positive or negative and (b) optionally further assessing IL-6 levels. The methods described herein may be carried out using body fluids other than cord blood. For example, fluids obtained from a subject such as neonatal blood, cerebral spinal (cerebrospinal) fluid, urine, saliva, tear fluid, meconium and feces, may also be used. Analysis of e.g. Hp and HpRP switching and/or Hp and/or HpRP level can be carried out by immunological, as well as non-immunological, methods known in the art.

Specific embodiments of the method are as follows:

(1) A method of diagnosing, or predicting the future development of, early onset neonatal sepsis or a (one, one or more) related complication(s) of premature birth (PTB) in a subject, comprising (the step of) detecting an increase in the level of (a) haptoglobulin and/or a fragment thereof; (b) haptoglobulin and/or a fragment thereof and haptoglobulin-related protein and/or a fragment thereof; or (c) haptoglobulin-related protein and/or a fragment thereof in a sample of blood, such as cord blood or neonatal blood from the subject. In this method, (the step of) detecting comprises detecting/determining (a) presence or absence of haptoglobin and/or a fragment thereof; (b) haptoglobin and/or a fragment thereof and/or haptoglobin-related protein and/or a fragment thereof; or (c) haptoglobin-related protein and/or a fragment thereof in a sample obtained from the subject. In this embodiment and all other embodiments described herein the method can be an ex vivo method.

(2) A method for diagnosing, or predicting the future development of (risk of developing), early onset neonatal sepsis or a (one, at least one, one or more) related complication(s) of premature birth in a subject, comprising (the step of) detecting, in a sample of blood, such as cord blood or neonatal blood from said subject, a change in the level of at least one (a, one, one or more) protein and/or a fragment thereof selected from:

TABLE 1

| IPI ID# | Abbreviation/Name |
|---|---|
| IPI00021842 | APOE apolipoprotein E precursor |
| IPI00022434 | ALB uncharacterized protein ALB |
| IPI00022443 | AFP alpha-fetoprotein precursor |
| IPI00216773 | ALB ALB protein |
| IPI00298828 | APOH Beta-2-glycoprotein 1 precursor |
| IPI00304273 | APOA4 Apolipoprotein A-IV precursor |
| IPI00384697 | ALB Isoform 2 of serum albumin procursor |
| IPI00431645 | HP HP protein |
| IPI00477597 | HPR isoform 1 of Haptoglobin-related protein precursor |
| IPI00478003 | A2M Alpha-2-macroglobulin precursor |

TABLE 1-continued

| IPI ID# | Abbreviation/Name |
|---|---|
| IPI00478493 | HP Haptoglobin Isoform 2 preprotein |
| IPI00555812 | GC Vitamin D-binding protein precursor |
| IPI00607707 | HPR Isoform 2 of Haptoglobin-related protein precursor |
| IPI00641737 | HP Haptoglobin precursor |
| IPI00742696 | GC Vitamin D-binding protein precursor |
| IPI00745872 | ALB Isoform 1 of serum albumin precursor |
| IPI00847179 | APOA4 apolipoprotein A-IV precursor |
| IPI00878517 | ALB 56 kDa protein |
| IPI00878953 | APOE MRNA for apolipoprotein E |
| IPI00879456 | APOE 25 kDa protein | and fragments of each of the above-listed proteins.

(3) A method of diagnosing, or predicting the future development of (risk of developing), early onset neonatal sepsis or a (one, at least one, one or more) related complication(s) of premature birth (PTB) in a subject, wherein the complication is intraventricular haemorrhage. The method can be a method of either of the preceding claims.

(4) A method of any one of the preceding claims, wherein the sample of cord blood is collected at birth.

(5) A method of any one of the preceding claims, wherein detecting (the detecting step) comprises detecting a decrease in the level(s) of apolipoprotein H (and/or a fragment thereof) and/or apolipoprotein E (and/or a fragment thereof) and/or vitamin D-binding protein (and/or a fragment thereof). In specific embodiments, detecting (the detecting step) comprises detecting a decrease in the level(s) of apolipoprotein H and/or a fragment thereof; apolipoprotein E and/or a fragment thereof; vitamin D-binding protein and/or a fragment thereof; apolipoprotein H and/or a fragment thereof and apolipoprotein E and/or a fragment thereof; apolipoprotein H and/or a fragment thereof and vitamin D-binding protein and/or a fragment thereof; apolipoprotein E and/of a fragment thereof and vitamin D-binding protein and/or a fragment thereof; or apolipoprotein H and/or a fragment thereof, apolipoprotein E and/or a fragment thereof and vitamin D-binding protein and/or a fragment thereof. In further embodiments, the method comprises detecting a decrease in the level(s) of at least one (a, one, one or more) of the listed biomarkers.

(6) A method of any one of claims 2 to 4, wherein detecting (the detecting step) comprises detecting an increase in the level(s) of (a) haptoglobulin and/or a fragment thereof; (b) haptoglobulin and/or a fragment thereof and haptoglobulin-related protein and/or a fragment thereof; or (c) haptoglobulin-related protein and/or a fragment thereof.

(7) A method of any one of the preceding claims, wherein detecting (the detecting step) comprises detecting (a) a decrease in the level(s) of apolipoprotein H and/or apolipoprotein E and/or vitamin D-binding protein and (b) an increase in the level(s) of haptoglobulin and/or haptoglobulin-related protein. In specific embodiments, detecting (the detecting step) comprises detecting (a) a decrease in the level(s) of (i) apolipoprotein H and/or a fragment thereof; (ii) apolipoprotein E and/or a fragment thereof; (iii) vitamin D-binding protein and/or a fragment thereof; (iv) apolipoprotein H and/or a fragment thereof and apolipoprotein E and/or a fragment thereof; (v) apolipoprotein H and/or a fragment thereof and vitamin D-binding protein or a fragment thereof; (vi) apolipoprotein E and/or a fragment thereof and vitamin D-binding protein and/or a fragment thereof; or (vii) apolipoprotein H and/or a fragment thereof, apolipoprotein E and/or a fragment thereof and vitamin D-binding protein and/or a fragment thereof and (b) detecting an increase in the level(s) of (i) haptoglobulin and/or a fragment thereof; (ii) haptoglobulin and/or a fragment thereof and haptoglobulin-related protein and/or a fragment thereof; or (iii) haptoglobulin-related protein and/or a fragment thereof.

(8) A method of any one of the preceding claims, wherein the subject is a premature neonate.

(9) The method of any one of the preceding claims wherein the blood is cord blood.

(10) A method of diagnosing, or predicting the future development of, early onset neonatal sepsis and/or at least one related complication of prematurity (preterm birth) in a subject, comprising determining if antenatal Hp switching on has occurred in the subject by analyzing a sample obtained from the subject for Hp; HpRP; or both Hp and HpRP, wherein if Hp; HpRp; or both Hp and HpRP is/are detected in the sample, antenatal HP switching on has occurred and the subject has or is at increased risk of developing EONS and/or at least one related complication of prematurity (preterm birth).

(11) The method of claim 10, wherein the subject is a premature neonate.

(12) The method of claim 10 or claim 11, wherein the sample is a cord blood sample, a neonatal blood sample, a cerebrospinal fluid sample, a urine sample, a tear fluid sample, a meconium fluid or a fecal sample.

(13) The method of any one of claims 10 to 12, further comprising determining the level of Hp; HpRP; or both Hp and HpRP in the sample and comparing the level with the corresponding level in an appropriate control.

(14) The method of any one of claims 10 to 13, wherein the appropriate control is (a) a newborn (i) matched for gestational age with the subject; (ii) with low cord blood IL-6 (such as less than 9 pg/ml); and (iii) delivered in the setting of idiopathic preterm birth or (b) a newborn delivered from an uncomplicated pregnancy and delivery.

(15) A method of diagnosing, or predicting the future development of, early onset neonatal sepsis and/or at least one related complication(s) of prematurity (preterm birth) in a subject, comprising determining the level of Hp; HpRP; or Hp and HpRP in a sample of blood obtained from the subject, wherein if Hp; HpRP; or Hp and HpRP is/are present in the sample at a level equal to or greater than the level of Hp; HpRP; or Hp and HpRP in an appropriate control, the subject has or is at increased risk of future development of EONS and/or at least one related complication of prematurity (preterm birth).

(16) The method of claim 10, wherein the subject is a premature neonate.

(17) The method of claim 15 or claim 16, wherein the blood sample is a cord blood sample or a neonatal blood sample.

(18) The method of any one of claims 15 to 17, wherein the level of Hp; HpRP; or Hp and HpRP is equal to or greater than the level in an appropriate control and the appropriate control is a premature neonate who progressed to EONS and/or at least one related complication of prematurity (preterm birth).

(19) The method of any one of claims 15 to 17, wherein the level of Hp; HpRP; or Hp and HpRP is greater than the level in an appropriate control and the appropriate control is (a) a newborn (i) matched for gestational age with the subject; (ii) with low cord blood IL-6 (such as less than 9 pg/ml); and (iii) delivered in the setting of idiopathic preterm birth or (b) a newborn delivered from an uncomplicated pregnancy and delivery.

(20) A method of diagnosing, or predicting the future development of, early onset neonatal sepsis and/or at least one related complication of prematurity (preterm birth) in a subject, comprising determining if (a) cord blood IL-6 is positive, relative to an appropriate control, and (b) Hp and/or HpRP switching has occurred, wherein if cord blood IL-6 is positive and Hp and/or HpRP switching has occurred, the subject has or is at increased risk of future development of EONS and/or at least one related complication of PTB.

(21) The method of claim 20, wherein the subject is a premature neonate.

(22) The method of claim 20 or claim 21, wherein the blood sample is a cord blood sample or a neonatal blood sample.

(23) The method of any one of claims 20 to 22, wherein the appropriate control for cord blood IL-6 is cord blood IL-6 in (a) a newborn (i) matched for gestational age with the subject; (ii) with low cord blood IL-6; and (iii) delivered in the setting of idiopathic preterm birth or (b) a newborn delivered from an uncomplicated pregnancy and delivery.

(24) The method of any one of claims 20 to 23, wherein the appropriate control has a cord blood IL-6 level of less than about 9 pg/mL.

(25) A method of diagnosing, or predicting the future development of, early onset neonatal sepsis and/or at least one related complication of prematurity (premature birth) in a subject, comprising determining IL-6 level and the phenotype of Hp in a sample of blood obtained from the subject, wherein if the IL-6 level is positive and the phenotype of Hp is Hp 0-0, Hp1-1, Hp2-1 or Hp2-2, the subject has or is at increased risk of future development of early onset neonatal sepsis and/or at least one related complication and if the IL-6 level is negative and the phenotype of Hp is Hp0-0, the subject does not have or is at less risk of developing EONS and/or at least one related complication of prematurity (premature birth).

(26) A method of diagnosing, or predicting the future development of, early onset neonatal sepsis and/or at least one related complication of prematurity (premature birth) in a subject, comprising determining the relationship of Hp with the presence of bacterial DNA in a sample of blood obtained from the subject, wherein if Hp and/or HpRP and bacterial DNA are present in the sample of blood, the subject has or is at risk of developing early onset neonatal sepsis and/or at least one related complication of prematurity (premature birth).

(27) A method of diagnosing, or predicting the future development of, early onset neonatal sepsis and/or at least one related complication of prematurity (premature birth) in a subject, comprising assessing at least two of the following characteristics in a sample of blood obtained from the subject: (a) antenatal Hp and/or HpRP switching on; (b) phenotype of Hp; HpRp; or Hp and HpRp; (c) level of Hp; HpRP; or Hp and HpRP; (d) cord blood IL-6 or the relationship of the level of Hp; HpRP; or Hp and HpRP to interleukin-6 level (referred to as Hp/IL-6 ratio); and (e) the relationship of Hp and/or HpRP with the presence of bacterial DNA, wherein if the sample is determined to comprise a blood signature comprising at least two characteristics indicative of early onset neonatal sepsis or an increased risk of developing at least one related complication of prematurity (preterm birth), the subject is diagnosed as having early onset neonatal sepsis or an increased risk of developing at least one related complication of prematurity (preterm birth).

(28) The method of claim 27, wherein antenatal Hp and/or HpRP switching on and cord blood IL-6 are assessed and Hp and/or HpRP switching on has occurred and cord blood IL-6 is positive.

(29) The method of claim 28 or claim 28, wherein the subject is a premature neonate.

(30) The method of any one of claims 27 to 29, wherein cord blood IL-6 is greater than about 9 pg/mL.

(31) The method of any one of claims 1 to 31, wherein the complication can be IVH, bronchopulmonary dysplasia (BPD, need for oxygen at 36 weeks postmenstrual age), retinopathy of prematurity (ROP), cerebral palsy and/or death.

(32) A method of diagnosing, or predicting the future development of, early onset neonatal sepsis and/or at least one related complication of prematurity (preterm birth) in a subject, comprising assessing, in a blood sample obtained from the subject, IL-6 level; Hp and/or HpRP switching; and, optionally (further comprising), Hp type, wherein:

(a) if the CB IL-6 level is negative (not elevated), relative to an appropriate control; Hp and/or HpRP switching is negative (has not occurred); and, optionally, Hp type is Hp 0-0, the conclusion is that the neonate has not been exposed to an in utero event (e.g., bacterial encounter), Hp and/or HpRP switching has not occurred, the subject does not have and is not at increased risk of developing EONS and/or at least one related complication(s), the prognosis is good and antibiotic therapy is not needed;

(b) if the IL-6 level is elevated, relative to an appropriate control; Hp and HpRP switching is negative (has not occurred); and, optionally, Hp type is Hp 0-0, the subject has or is at increased risk of developing EONS and/or at least one related complication(s), the conclusion is that the neonate has been exposed to an in utero event (e.g., bacterial encounter), Hp and HpRP switching has not occurred, the prognosis is poor and the neonate should receive treatment, such as admission to NICU and antibiotic therapy;

(c) if the IL-6 level is elevated, relative to an appropriate control; Hp and HpRP switching is positive (has occurred); and, optionally, Hp type is Hp 1-1, Hp 1-2 or Hp 2-2, the subject has or is at risk of developing EONS and/or at least one related complication(s), the conclusion is that the neonate has been exposed to an in utero event (e.g., bacterial encounter) and the outcome (prognosis) will vary, depending on the Hp phenotype and the neonate will need further assessment and should be admitted to NICU and treated, such as by antibiotic therapy.

(33) The method claim 32, wherein the blood sample is a cord blood sample or a neonatal blood sample.

(34) The method of claim 32 or claim 33, wherein the subject is a premature neonate.

(35) The method of any one of claims 1 to 34, wherein the complication can be IVH and/or bronchopulmonary dysplasia (BPD and/or need for oxygen at 36 weeks postmenstrual age) and/or retinopathy of prematurity (ROP) and/or cerebral palsy and/or death.

In each of the embodiments of the method, the biomarkers can be any of those described herein (e.g., any of the protein biomarkers listed in the Table, CB IL-6, Hp phenotype or HpRP phenotype, or Hp or HpRP switching), alone (individually) or in combination with one or more additional biomarker described herein. A single biomarker (at least one, one or more biomarker) can be used in a method of diagnosing, or predicting the future development of (risk of developing), early onset neonatal sepsis or a (one, at least one, one or more) related complication(s) of premature birth (PTB) in a subject. Two or more (at least two) biomarkers can be used in the method, as can any number of biomarkers described herein. The methods described herein can be used in conjunction with other methods, such as presently-available methods of diagnosing, or predicting the future development of, complication of premature birth.

In specific embodiments of diagnosing or predicting the future development of EONS, the one or more biomarker(s) detected are selected from the following group: apolipoprotein H, an apolipoprotein H fragment, apolipoprotein E, an apolipoprotein E fragment, Vitamin D-binding protein, a Vitamin D-binding protein fragment, haptoglobulin, a haptoglobulin fragment, haptoglobulin-related protein and a haptoglobulin-related protein fragment. In further specific embodiments, the method comprises detecting a decrease in the level(s) of a (one, one or more, at least one) biomarker selected from apolipoprotein H, apolipoprotein H fragments, apolipoprotein E, apolipoprotein E fragments, vitamin D-binding protein, and vitamin D-binding protein fragments and detecting an increase in the level(s) of a (one, one or more, at least one) biomarker selected from haptoglobulin, haptoglobulin fragments, haptoglobulin-related protein and haptoglobulin-related protein fragments.

The biomarker(s) are detected, using methods described herein, in blood obtained from a subject (neonate, newborn, infant), using known collection techniques. The blood can be cord blood, blood other than cord blood drawn from the subject, urine, cerebrospinal fluid, tear fluid, saliva, meconium or feces.

There are further embodiments of the method. In one embodiment, the method is a method, such as an ex vivo method, of diagnosing, or predicting the future development of, early onset neonatal sepsis or a (at least one, one, one or more) related complication(s) of prematurity (or PTB) in a subject (e.g., a neonate, such as a preterm or premature neonate), comprising (the step of) determining if antenatal Hp switching on has occurred in the subject by analyzing a sample of blood obtained from the subject (e.g., cord blood, neonatal blood or umbilical cord blood) for Hp; HpRP; or both Hp and HpRP or a fragment of any of the foregoing, wherein if Hp; HpRp; or both Hp and HpRP or a fragment thereof is/are detected in the sample, antenatal HP switching on has occurred and the subject has or is at increased risk of developing EONS and/or a (one, one or more) related complication(s) of PTB. The complication(s) can be, for example, IVH, bronchopulmonary dysplasia (BPD, need for oxygen at 36 weeks postmenstrual age), retinopathy of prematurity (ROP), cerebral palsy and/or death.

In another embodiment, the method is a method, such as an ex vivo method, of diagnosing, or predicting the future development of, early onset neonatal sepsis or a (at least one, one or more) related complication(s) of prematurity (PTB) in a subject, comprising (the step of) determining the level of Hp; HpRP; or Hp and HpRP in a sample of blood obtained from the subject, wherein if Hp; HpRP; or Hp and HpRP are present in the sample at a level equal to or greater than the level of Hp; HpRP; or Hp and HpRP in an appropriate control or reference, the subject has or is at increased risk of future development of EONS and/or a (one or more, at least one) related complication(s) of PTB. The appropriate control or reference can be the level of Hp, HpRP or Hp and HpRP in blood from newborns matched for GA with low CB IL-6 (<9 pg/mL) and delivered in the setting of idiopathic PTB, the level of HpRP or Hp and HpRP in blood from term babies with uncomplicated pregnancy and delivery assessed by the same method or the level of Hp; HpRP; or Hp and HpRP in blood from adults.

In another embodiment, the method is a method, such as an ex vivo method, of diagnosing, or predicting the future development of (risk of developing), early onset neonatal sepsis or a (one, one or more) related complication(s) of premature birth (PTB) in a subject, comprising (the step of) determining the relationship of the level of Hp; HpRP; or Hp and HpRP to interleukin-6 (IL-6) level (referred to as Hp/IL-6 ratio) in a sample of blood obtained from the subject, wherein if the Hp/IL-6 ratio is greater in the sample than the Hp/IL-6 ratio in an appropriate control or reference, the subject has or is at increased risk of future development of EONS and/or a (one or more, at least one) related complication(s) of PTB. The appropriate control or reference can be the Hp/IL-6 ratio in blood from newborns matched for GA and delivered in the setting of idiopathic PTB; the level of HpRP or Hp and HpRP in blood from term babies with uncomplicated pregnancy and delivery assessed by the same method or the level of Hp; HpRP; or Hp and HpRP in blood from adults.

In another embodiment, the method is a method, such as an ex vivo method, of diagnosing, or predicting the future development of, early onset neonatal sepsis and/or at least one related complication of prematurity (premature birth) in a subject, comprising determining IL-6 level and the phenotype of Hp in a sample of blood obtained from the subject, wherein if the IL-6 level is positive and the phenotype of Hp is Hp 0-0, Hp1-1, Hp2-1 or Hp2-2, the subject has or is at increased risk of future development of early onset neonatal sepsis and/or at least one related complication and if the IL-6 level is negative and the phenotype of Hp is Hp0-0, the subject does not have or is at less risk of developing EONS and/or at least one related complication of prematurity (premature birth).

In another embodiment, the method is a method, such as an ex vivo method, of diagnosing, or predicting the future development of (risk of developing), early onset neonatal sepsis and/or at least one (a, one, one or more) related complication of prematurity (premature birth) in a subject, comprising (the step of) determining the relationship of Hp with the presence of bacterial DNA in a sample of blood obtained from the subject, wherein if Hp and/or HpRP and bacterial DNA are present in the sample of blood, the subject has or is at risk of developing early onset neonatal sepsis and/or at least one related complication of prematurity (premature birth).

In a particular embodiment, two or more (three or more, four or more or five) of the characteristics (element) described above (antenatal Hp switching; level of Hp, HpRP, or Hp and HpRP; relationship of the level of Hp, HpRP, or Hp and HpRP to (IL-6) level (referred to as Hp/IL-6 ratio); phenotype of Hp; relationship of Hp with the presence of bacterial DNA) are assessed in diagnosing, or predicting the likelihood of future development of, early onset neonatal sepsis and/or a (one, one or more) related complication(s) of PTB in a subject. The result of this embodiment is referred to as a "cord blood Hp signature," which comprises results of assessing the two or more characteristics results. For example, in one embodiment, two or three of the following are assessed in diagnosing or predicting the likelihood of future development of EONS: Cord blood (CB) IL-6 (positive or negative); CB Hp and/or HpRP switching; and CB Hp phenotype. Diagnoses and predicted outcomes and suggested therapies are shown in Table 2. In one embodiment, CB IL-6 level; CB Hp and HpRP switching; and CB Hp type are assessed, using known methods. Several possible outcomes can result, including the following. (1) The CB IL-6 level is negative (not elevated, relative to an appropriate control); CB Hp and HpRP switching is negative (has not occurred); and CB Hp type is Hp 0-0 in the subject; the conclusion is that the neonate has not been exposed to an in utero event (e.g., bacterial encounter), Hp and HpRP switching has not occurred, the prognosis is good and antibiotic therapy is not needed. (2) The CB IL-6 level is elevated, relative to an appropriate control; CB Hp and HpRP switching is negative (has not occurred); and CB Hp type is Hp 0-0 in the subject and the conclusion is that the neonate has been exposed to an in utero event (e.g., bacterial encounter), Hp and HpRP switching has not occurred, the prognosis is poor and the neonate should receive treatment, such as admission to Neonatal Intensive Care Unit (NICU) and/or antibiotic therapy. (3) The CB IL-6 level is elevated, relative to an appropriate control; CB Hp and HpRP switching is positive (has occurred); and CB Hp type is Hp 1-1, Hp 1-2 or Hp 2-2 in the subject, the conclusion is that the neonate has been exposed to an in utero event (e.g., bacterial encounter), Hp and HpRP switching has occurred. In this case, the outcome (prognosis) will vary, depending on the Hp phenotype; the neonate will need further assessment and should be considered for admission to NICU and treatment, such as by antibiotic therapy. Hepatic Hp synthesis is dependent on cis-acting elements localized within the first 186 bp of the 5'-flanking region of the promoter. Interaction of this promoter site with trans-acting elements is postulated to provide a second level of complexity in regulation of Hp expression, which further explains why in individuals with the same genotype, Hp levels vary with exposure to environmental or epigenetic stressors (physical effort, methylation status).[10] It is known for adults that haptoglobin concentration measured by ELISA is phenotype-dependent. The reference range for haptoglobin concentration is lower in individuals carrying the Hp2-2 phenotype than individuals carrying the Hp1-1 and Hp2-1 phenotype. Therefore, Hp2-2 phenotype confers a state of relative ahaptoglobinemia. Few individuals may lack both Hp alleles, giving raise to Hp0-0 phenotype. Further assessment of the neonate can comprise determining his/her Hp phenotype and include the result of that assessment in decisions regarding treatment. (4) If the CB IL-6 level is not elevated (negative), relative to an appropriate control; CB Hp and HpRP switching is positive (has occurred); and CB Hp type is Hp 1-1, Hp 2-1 or Hp 2-2, the conclusion is that the neonate has been exposed to an in utero event (e.g., bacterial encounter), Hp and HpRP switching has occurred, the prognosis is poor and the neonate should be admitted to NICU and treated, such as with antibiotic therapy. This latter outcome is rare and occurs most often in neutropenic fetuses.

1) EONS (n=46) was characterized more often by antenatal Hp switching-on (P<0.001) and significantly higher Hp levels (P<0.001), independent of GA and IL-6;

2) Phenotypes impacted Hp level: Hp2-1>Hp2-2>Hp1-1 (P<0.001);

3) Newborns with EONS and Hp2-1 had the highest Hp levels, double that of Hp1-1 (P=0.003);

4) Neonates who developed IVH or died (n=36) had higher Hp levels (P<0.001) independent of GA, IL-6, cord pH, steroid and antibiotic use;

5) Newborns with switched-on Hp at birth had an increased risk of IVH and death (RR: 3.6 [1.8-7.8]); 6) No term neonate (but all adults) had switched-on Hp.

In all of the methods described herein, any of a variety of known techniques/methods can be used to assess the biomarkers. For example, inflammation, such as intraamniotic inflammation or fetal/neonatal inflammatory status can be assessed by IL-6 levels, which can be determined, for example, by SELDI-TOF mass spectrometry, ELISA (IL-6 Cytokine ELISA kit, Abnova, BD BioSciences, Cell Sciences), EIA (enzyme immune assay, Cayman Chemical), and other colorimetric assay, Western blot, semiquantitative PCR, and other nucleic acid based methods. Bacterial status (e.g., bacterial status of neonates with EONS who have negative microbial cultures) can be assessed using gene amplification techniques (e.g., PCR, RT-PCR, 16s-RNA gene amplification, other hybridization techniques, or antibody-based methods. Expression patterns and Hp presence can be detected by e.g. SELDI-TOF, ELISA, Western blot and PCR-based techniques, and phenotyping can be assessed by Western blot analysis, ELISA, high pressure gel permeation chromatography, SELDI-TOF, polyacrylamide gel isoelectric focusing (PAGIF), capillary zone electrophoresis, conventional starch gel electrophoresis or other electrophoresis methods using e.g. starch, acetate, agarose and polyacrylamide gels (J. Delanghe et al. "Fast determination of haptoglobin phenotype and calculation of hemoglobin binding capacity using high pressure gel permeation chromatography" Clinica Chimica Acta Vol. 291, 2000, 43-51; Fukuda et al. "Haptoglobin phenotyping by polyacrylamide gel isoelectric focusing and its application to simultaneous typing of serum proteins" Int. J. Legal Med. Vol. 101, 1988, 37-40; Wuyts et al. "A new method for fast haptoglobin phenotyping and hemoglobin binding capacity calculation based on capillary zone electrophoresis" Clin. Chem. Lab. Med. Vol. 38, 2000, 715-720; Levy et al. "ELISA for Determination of the Haptoglobin Phenotype" Clinical Chemistry, Vol. 50, 2004, 2148-2150; Wassell et al. "A new method for haptoglobin phenotyping" Ann Clin Biochem., 36, 1999, 609-12). Differential expression of Hp can be validated with ELISA. Other analytical methods can be immunological methods, for example employing one or more antibodies directed against all three polypeptide bands specific to Hp and/or HpRP, Hp isoform specific or HpRP specific and non-immunological methods. Non-immunological methods include mass spectrometry, colorimetric assays, using, for example, the ability of Hp to bind hemoglobin and of the resulting Hp-Hb complex to react with certain dyes. In addition to antibodies that are specific for Hp, other antibodies that are cross reactive with other proteins (bind non-specifically with Hp and/or HpRP) can be used, as described herein.

BRIEF DESCRIPTION OF THE DRAWINGS

FIGS. 2 and 3 show the design of proteomic studies. FIG. 2 outlines the discovery phase, in which the study group consisted of 3 neonates with confirmed positive *E. coli* sepsis, high cord blood IL-6, positive amniotic fluid cultures and grade 4 histological chorioamnionitis. Three fetuses matched for gestational age and delivered in the setting of idiopathic preterm birth served as control.

FIG. 3 outlines the proteomic techniques: to identify biomarkers, first fluorescence 2 dimensional differential gel electrophoresis was performed after albumin and IgG depletion. This was followed by robotic tryptic digest and tandem mass spectrometry. Pathway analysis was performed using Protein Analysis Through Evolutionary Relationships (PANTHER) ontological classification. In the validation phase, immunoassays and Western blot analysis were used to assess the differential expression of specific markers in the entire cohort.

FIG. 4 shows results of study-described herein. Forty neonates were diagnosed with early onset sepsis. They delivered at an earlier gestational age, had lower birth weight and Apgar scores. Their acid base status was not different compared to controls.

FIG. 6 shows results of assessment of neonatal sepsis. Analysis of hematological indices showed that neonates with early onset sepsis had lower hemoglobin levels and were more frequently lymphopenic. They had a higher absolute band count and immature to total neutrophil ratio. Overall, out of the 40 neonates with early onset sepsis, 8 had a documented positive microbial culture.

FIG. 9 shows results of analysis of potential protein biomarkers, using PANTHER. Of the 20 matched identities, several converged into the same protein and a smaller number of potential down- or up-regulated protein biomarkers was identified. These included Apolipoprotein H, Apolipoprotein E, Vitamin D binding protein, Haptoglobin and Haptoglobin related protein.

FIG. 14B: CB Hp&HpRP in the subgroup of 92 newborns that were evaluated for IVH (head ultrasound and/or MRI) or that died postnatally. Note the y-axis units in micrograms/mL. Standard curve ranged from 4-250 ng/mL. Serum was diluted 150-fold. Hp and HpRP are >90% homologous and are not differentiated in this ELISA.

FIG. 23A demonstrates that Hp phenotype impacts on optical density (OD) measured in ELISA. Samples of adult Hp purified from individuals with known phenotype (Hp1-1, 1-2 or 2-2, purchased from Sigma) were diluted progressively in the range of the standard curve and analyzed in ELISA (n=3 independent observations). FIG. 23B shows a relationship between cord blood Hp&HpRP immunoreactivity measured by ELISA and by Western blot in denatured and reducing conditions (n=180). The continuous red line represents the linear regression line, the red dotted lines mark the 95% confidence interval and the dotted black lines the 95% prediction interval. FIG. 23C is the ROC analysis which demonstrates the relationship between Hp switch-on pattern and Hp&HpRP cord blood levels measured by ELISA. An ELISA cut-off of 3,370 ng/mL was deemed optimal to discriminate between the Hp switch-on and Hp switch-off pattern by Western blot (n=180).

DETAILED DESCRIPTION OF THE INVENTION

Figure 1:
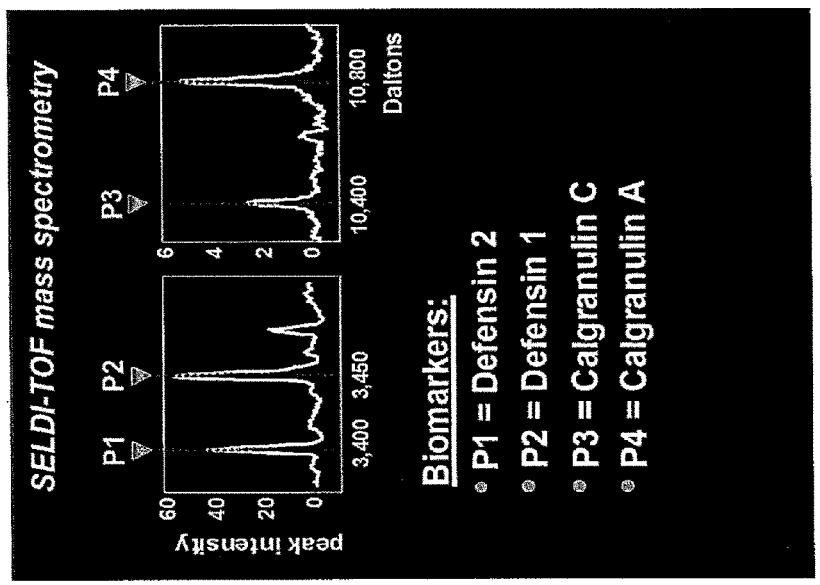
FIG. 1 is a representation of SELDI-TOF proteomic profiling of amniotic fluid for diagnosis of intra-amniotic inflammation, infection and early onset neonatal sepsis and Applicant's proteomic profile, the MR score, which is comprised of four biomarkers: defensin-2, defensin-1, calgranulin C and calgranulin-A.
Figure 2:
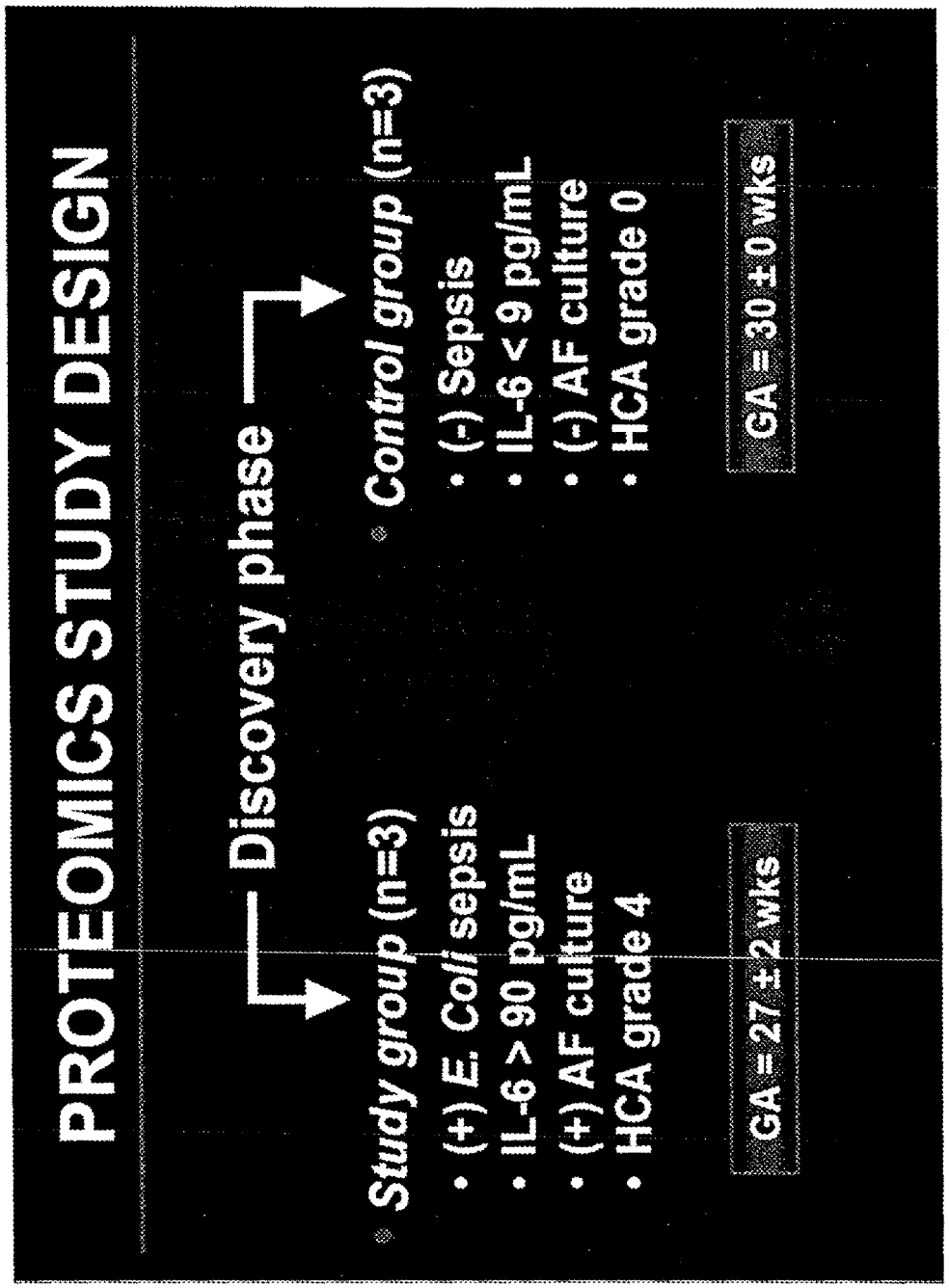

Using DNA-based technologies corroborated with proteomic analysis of amniotic fluid (AF), Applicant determined that microbial triggers involve a myriad of uncultivated or difficult-to-culture bacterial species capable of inducing potent fetal immune responses and cellular damage. Applicant found that such etiological agents are present in the cord blood (CB) of newborns who have early onset neonatal sepsis (EONS), yet have negative blood cultures. Using proteomics (2D-DIGE) Applicant further discovered that CB haptoglobin (Hp) and haptoglobin-related protein (HpRP) are biomarkers of EONS and IVH, independent of GA at birth or birth weight. Specifically, Applicant has shown that Hp, an abundant antimicrobial, anti-oxidant and immunomodulatory protein normally absent at birth, precociously switches on expression in fetuses who had an antenatal encounter with an infectious trigger. From a diagnostic standpoint, this marked quantitative and qualitative change creates a signature for use to predict newborns at high risk for adverse outcomes, thus enabling targeted immediate interventions in this select subgroup. Hp is a highly abundant and stable protein and, thus, it can be reliably and rapidly detected in minute amounts of blood, using technologies easily adaptable for point-of-care (immunoassay, biosensors, mass spectrometry).

Proteomic analysis of cord blood samples (using the methodology described in Buhimschi et al. PLoS ONE 3 (4): e2049) resulted in identification of 20 proteins and protein fragments (listed in the Table 1) in cord blood samples from babies who subsequently developed EONS. The levels of the 20 proteins and protein fragments were either increased or decreased by 3-fold or greater, compared to controls. Thus, proteomic analysis resulted in identification of biomarkers (proteins and protein fragments) and functional protein networks characteristic of EONS. Analysis of the levels of one or more (a, at least one) of these proteins or protein fragments is useful in diagnosing EONS in a newborn and predicting the likelihood that a newborn will develop EONS and/or related complications of prematurity. Based on these data, it is clear that detecting changes in the level of one or more of these proteins and/or protein fragments is diagnostic of EONS and predictive for the development of EONS and related complications of prematurity, such as intraventricular hemorrhage (IVH). Decreases in the levels of Apolipoprotein H and/or Apolipoprotein E and/or Vitamin D-binding protein and/or increases in Haptogobin and/or Haptoglobin-related protein are markers that can be used for assessing complications of prematurity or preterm birth (PTB), such as EONS and related complications of prematurity.

Use of such markers as described herein provides a significant advance. The ease of detection of such proteins and protein fragments makes it possible to provide diagnostic and prognostic information about a subject more rapidly than presently-available methods, with the result that situations where therapeutic intervention is necessary can be better identified and appropriate treatment can be initiated sooner.

As discussed herein, Applicant has assessed the hypothesis that interactions of environmental stressors with genetically determined variations in Hp phenotypes and/or Hp levels are important determinants of susceptibility to adverse neonatal outcomes. The environmental stressors can be an infectious agent, such as bacteria, virus, yeast or parasite. As further discussed, Applicant has developed a method of assessing the likelihood that a newborn or infant has (diagnosing or aiding in diagnosing) or will develop (is at risk of developing) early onset neonatal sepsis (EONS) or related complications of prematurity. The method is generally carried out up to and including three days after birth, but it can be used in older newborns, such as up to 4, 5, 6, 7 or more days after birth. The method is a method of diagnosing (the presence of) EONS in a subject (e.g., a human newborn or a human infant human, or predicting the future development of, early onset neonatal sepsis or related complications of prematurity). In one embodiment, the method of diagnosing, or predicting the future development of (risk of developing), early onset neonatal sepsis or related complications of prematurity in a subject (newborn), comprises detecting an increase in the level of haptoglobulin and/or haptoglobulin-related protein (detecting an increase in the level of at least one, one or more of haptoglobulin and/or haptoglobulin-related protein) in a sample of cord blood from the subject. In a specific embodiment, the method comprises the step of detecting an increase in the levels of haptoglobulin and/or haptoglobulin-related protein in a sample of cord blood from the subject. In other embodiments haptoglobulin and/or haptoglobulin-related protein levels are detected in a body fluid that is not cord blood, such as neonatal blood, cerebral spinal fluid, urine, tear fluid, meconium or feces. As also described herein, the biomarker is abundant in blood samples and is known to be stable, which supports its reliable detection in dried blood spots, such as archived Guthrie cards, dried fingerstick and dried CB spots. One embodiment described herein is a method of assessing the likelihood that a newborn or infant has or will develop early onset neonatal sepsis (EONS) or related complications of prematurity by detecting an increase in Hp and/or HpRP in a dried sample obtained from the subject, dried finger stick and dried CB, such as dried CB spots.

Also described herein is a method in which Hp and/or HpRP signature assessment at birth (in CB) and longitudinally in NICU thereafter (in neonatal blood) serves as (is used prospectively as) a biomarker of risk stratification for IVH and other adverse short-term outcomes in preterm newborns. The method is based on the relationship of the postnatal temporal change in Hp and/or HpRP signature and to outcome of preterm newborns. In the method, Hp, HpRP or Hp and HpRP signature is assessed in cord blood or other blood obtained from a preterm newborn and subsequently at intervals in neonatal blood and compared with an appropriate control or reference to assess the risk of IVH in the subject. These and other methods described herein can be carried out using one or a combination of a variety of known techniques, such as western blot analysis, ELISA, EIA, mass spectrometry, SELDI-TOF, OCR or AMMP biosensor technology. For example, assessment of CB Hp and HpRP signature can be carried out using one or a combination of western blot analysis, ELISA, EIA, mass spectrometry, SELDI-TOF, PCR and AMMP biosensor technology. Antibodies raised against Hp are known in the art and are commercially available, e.g., from DAKO, Abnova, Abcam, ABR/Thermo-Fisher-Pierce. See also Kuhajda, F P et al., Proc. Natl. Acad. Sci. USA 1989 86 (4): 1188-92; Kuhajda F P et al. Proc Natl. Acad. Sci. USA 1994 91 (14):6379-83; Epalbaum R. et al., Pathol. Oncol. Res. 1998 4 (4):271-6. These antibodies are derived from sheep, rabbit, goat, chicken (polyclonal) and mice (monoclonal) and can be used for example in ELISA, Western blot, immuno histochemistry (IHC) and radio immune assay (RIA). The antibodies can be specific for Hp, HpRP or both Hp and HpRP or cross react with proteins other than Hp or HpRP (nonspecific). Methods described herein can be carried out in samples, such as cord blood or other blood samples obtained from a neonate at or soon after birth or longitudinally after birth. Blood samples can be fresh or dried, such as archived samples or dried blood spots.

Interactions between maternal and/or fetal Hp phenotypes or levels can be assessed for their role as determinants of susceptibility to spontaneous PTB in pregnancies with infectious etiology. Hp 1-1 has the highest hemoglobin binding capacity but appears to be linked to greater susceptibility to infections. Hp 2-2 is the weakest binder to hemoglobin, which means that Hp 2-2 does not scavenge free radicals as well as the other phenotypes. After a neonate is exposed to an in utero event, (e.g., bacterial encounter) the Hp switching that occurs can determine the outcome. For example, a switching to Hp 1-1 phenotype leads to less of an ability to counter the bacterial infection, but the fetus or neonate is protected from oxidative injury. A switching to Hp 2-2 phenotype is effective in countering the bacterial infection but the fetus or neonate is less well protected from oxidative injury that can lead to brain injury. The phenotypic interplay between mother and fetus can be a determinant for outcome. For example, an Hp 1-1 mother may be more susceptible to infection and if the fetus/newborn exhibits switching to Hp 2-2 phenotype upon in utero encounter this may lead to brain damage; although a fetus/neonate with an Hp 2-2 phenotype can fight a bacterial infection, it is less well protected from brain injury caused by oxidative injury. Therefore, Hp phenotyping of the father and mother may be used for pre-birth counseling and determination of possible PTB-related outcomes, such as EONS, IVH and brain injury, according to genetic predispositions.

In another method, the Bioscale platform that is based on Acoustic Membrane Microparticle (AMMP™) resonance, a variant of surface plasmon resonance spectroscopy is used for detection of biomarkers. The AMMP technology was first developed at Massachusetts Institute of Technology (Cambridge, Mass.) and uses baits (antibodies, DNA strings) coupled to super-paramagnetic polymer particles that can be adsorbed onto a membrane using a magnetic field and quantified by the resulting change in frequency of a vibrating membrane as detected by a sensor. Because the detection relies on change in frequency of sound waves, it enables quantitative measurements of analytes at picogram levels in whole blood without need of centrifugation or dilution that are otherwise required for proper standard curve interpolation. A similar change in technology has led to virtually universal replacement of conventional end-point PCR with real-time PCR. Results with AMMP technology are available in 10-15 min. A significant advancement is that the sensor surfaces can be regenerated, reducing the cost per assay compared to other technologies (ELISA or mass spectrometry). The instrumentation varies from a hand held reader (ultra-rapid mode) to a tabletop model for enhanced sensitivity (ultra-sensitive mode).

Applicant has shown that PTB is a heterogeneous syndrome and that not all PTBs are equivalent, in terms of neonatal outcome. A major obstacle to a universal therapeutic intervention to prevent prematurity is the heterogeneous nature of PTB and the difficulties with defining the populations of women benefiting most from each available intervention versus no intervention. While several interventions (progesterone, cerclage, antibiotics) have been quoted as effective in preventing spontaneous PTB in subgroups of women at risk, not all have proven beneficial when neonatal outcomes are taken into consideration, as shown by the ORACLE trials.[11,12] Alternatively, given that long-term outcomes are only available for analyses after extended periods of time, it is difficult to evaluate in the short run the benefit versus detriment attributable to each particular intervention.

While multiple pathogenic mechanisms have been implicated in triggering PTB, several have received increased attention, specifically, genetic predisposition, stress, excessive stretching, decidual hemorrhage and infection inflammation.[13] The implicit paradigm that has governed the concept of the PTB syndrome is that independent activation of each of these pathways activates a final converging cascade of events leading to premature onset of myometrial contractions, preterm premature rupture of the membranes (PPROM) or both. Evidence suggests, however, that the poor outcome of many premature children is not entirely dependent on GA at birth or birthweight, but rather results from adverse processes that damage the fetus while in utero. Unfortunately, this process antedates the onset of PTB symptoms.[14] In particular, of all pathogenic pathways, intra-uterine infection and subsequent inflammation is the cause that contributes disproportionately to neonatal mortality and morbidity when adjusted for GA at birth.[15] The implication of this model is that in a subgroup of cases, particularities of the fetal innate immune response to infection cause pathology unique to the premature fetus including heightened oxidative and inflammatory states that act synergistically with microbial insult to induce damage. Obstetricians and their patients are faced daily with the dilemma of choosing between early delivery and the risk of iatrogenic prematurity and complications resulting from antenatal damage. The element which universally tips the balance towards early delivery in intra-uterine infection is the imminent risk for early-onset neonatal sepsis (EONS).[16] There is evidence to support the paradigm that prolonged exposure of the fetus to a noxious intra-uterine environment results in antenatal injury to vital organs, including the brain. One of the working models for infection-induced fetal damage is that some newborns have an inborn susceptibility to mount an increased state of inflammation in response to infection.[17] However, although infection-related PTBs have a disproportionately worse outcome than what could be attributed to prematurity alone, not all cases have a bad outcome. From an intervention standpoint, this model predicates the idea of "individualized medicine" aiming to use biomarkers to identify cases who may benefit from targeted rather than a "one size fits all therapy" in a modern diagnostic—therapeutic framework—"theranostics." To this end, predicting which infants are most likely to develop post-natal complications from infectious encounters in utero, with potential to exceed in severity those resulting from prematurity alone, remains a key problem.

The link between perinatal infection, inflammation and PTB is underestimated. The greatest etiological factor for PTB worldwide is infection, mainly due to malaria, HIV and parasites.[18] This is in contrast with most developed countries, where iatrogenic delivery is responsible for approximately half of the births between 28 and 35 weeks of gestation. One of the first evidence of intrauterine infection involvement in triggering PTB was provided by Larsen et al. at Yale more than 30 years ago.[19] Since then, data from Yale and other institutions directly implicate intrauterine infection as etiological factor for one quarter of pregnancies delivered before 34 weeks of gestation.[20,21] Adverse pregnancy outcomes related to infection are due to a direct microbial attack on the fetus and/or premature activation of the myometrial contractile machinery, dissolution of collagen architecture leading to cervical ripening or Preterm Premature Rupture of Membranes PPROM.[22,23]

Evidence of the causal role of infection in PTB is supported by a body of work demonstrating that microbial invasion of the amniotic cavity, as identified by positive amniotic fluid (AF) cultures, occurs in 10% of patients with preterm labor and intact membranes and in as many as 38% of patients with PPROM.[24] A variety of microbial pathogens have been implicated as etiologic agents of intra-amniotic infection.[25,26,27] The most frequently isolated pathogens are thought to originate primarily from the genital flora (*Gardnerella vaginalis, Mycoplasma hominis, Ureaplasma, Peptostreptococcus & Bacteroides* spp.).[27] This assumption is significantly biased by the limited number of laboratory techniques for pathogen cultivation which normally target for identification only a handful of microbes.[28] Thus, "uncultivated" or "difficult-to-cultivate" bacteria cannot be found when relying on culture conditions alone.[29,30] In contrast, culture-independent methods, such as PCR, can detect bacterial DNA in up to 35% to 60% of pregnancies complicated by PTB.[31,32] Yet, their use alone as diagnostics cannot discriminate between in vivo infection and ex vivo contamination and thus may result in unnecessary early deliveries. Irrespective of this potential bias, identification of intra-amniotic inflammation in the absence of a positive microbial culture result is a frequent finding in the clinical setting.[20] Using a proteomic fingerprint (the "MR score") as an indicator, Applicant observed that many women presenting with signs of PTB showed AF evidence of "severe inflammation," yet had negative cultures.[20] All samples that tested positive using Applicant's proteomics algorithm ultimately contained bacterial footprints.[33,34] Furthermore, most samples of AF with positive cultures contained additional bacteria compared to those found by cultures. In fact, 60% of species detected by culture-independent methods were missed by general laboratory cultures.[34] The missed prokaryotes belonged to the class of "uncultivated" and "difficult-to-cultivate" species, such as *Fusobacterium nucleatum, Leptotrichia/Sneathia, Bergeyella, Peptostreptococcus, Ureaplasma parvum, Bacteroides* and *Clostridiales* spp.[34] This suggests that in pregnancies complicated by PTB, the prevalence of AF infection and microbial diversity is underestimated. Moreover, it brings into perspective that the fetus may encounter pathogenic bacteria more often than previously thought. Interestingly, the majority of identified bacterial species were normal flora constituents with relatively low virulence, suggesting that their interaction with host's susceptibility may play a role.[35,36]

Early onset neonatal sepsis (EONS) is a major cause of neonatal morbidity and mortality. Sepsis in hospitalized neonates is a global problem and a significant contributor to morbidity and death. Both early- and late-onset sepsis occur with increased frequency in neonates born prematurely.[37,38,39] Mortality of culture positive (proven) neonatal sepsis ranges from 15% to 50%. In statistics published by Yale NBSCU, which holds the longest running, single-center database of neonatal sepsis started in 1928, mortality attributable to sepsis remains at 11% despite advances in neonatal care.[39] It is extremely important to make an early diagnosis of sepsis, because prompt institution of antimicrobial therapy improves outcomes. This is true for all newborns irrespective of GA at birth and more so for premature newborns because of their immature immune system. Isolation of bacteria from a central body fluid (usually blood) is the standard method to diagnose neonatal sepsis. However, the time required for the clinical laboratory to report results of cultures varies from 2-7 days, a timeframe which does not allow selection of cases for antibiotic therapy. Thus, the guidelines for clinical practice are that all newborns receive "empiric" broad spectrum antibiotics based on clinical suspicion of sepsis. In most circumstances, including at our institution, if blood culture results are not reported as positive by 48 to 72 hours, then antibiotics are discontinued.

There are significant downsides to overuse of this "initial empirical antibiotic therapy" for EONS. Aminoglycosides may be associated with important adverse effects and they require frequent monitoring of blood levels because of renal and oto-toxicity. Preterm infants have immature organs and therefore may not tolerate some antibiotics as well as term infants. In addition, the use of broad spectrum antibiotics in neonates may alter gut flora and increase the risk of developing necrotizing enterocolitis (NEC). A recent analysis conducted by the Neonatal NICHD Network on outcomes of over 3,000 premature newborns, concluded that each empiric antibiotic treatment day was associated with increased odds of death and/or NEC.[40] The current clinical practice dictates that antibiotics are mandatory in the antepartum period to decrease the risk of neonatal group B streptococcal (GBS) infections and to prolong pregnancy in women with PPROM. This antibiotic overuse in perinatal settings has and continues to create an environment for emerging bacterial resistance with potential for additional poor outcomes in the premature newborn population.[41] Moreover, the recent emergence of resistant Gram negative strains such as the ampicillin-resistant *E. coli*[24,25] is of concern and of major public health relevance. Not surprisingly, there is concern that continuing this practice will further change the diversity of microbes in NBSCUs, and will pose in the future a significant therapeutic challenge. The continuous increase in prevalence of antibiotic-resistant and ampicillin-resistant *E. coli* infections in preterm infants is a challenge and suggests that antibiotic prophylaxis in this group needs scientifically based restrictive guidelines.

There are several reasons why it is difficult to accurately diagnose EONS and why newborns are treated with empiric antibiotics, even when it is not necessary. Bloodstream infections fluctuate widely from 8% to 73% in the diagnosis of "suspected" EONS.[42,43] Another level of complexity is added by the observation that there are many newborns who have nonspecific clinical manifestations of EONS (e.g., lethargy, apnea, respiratory distress, hypoperfusion and shock). The majority of these newborns have negative cultures.[44] A different obstacle is technical and relates to the narrow spectrum of pathogens sought in microbiology laboratories. For example, searching for *Ureaplasma* and *Mycoplasma* spp. is not part of routine sepsis work-up in neonates. A study that evaluated the frequency of umbilical CB infections with these species found that that 23% of newborns born <32 weeks tested positive for these pathogens.[45] It is also plausible that analogous to intra-amniotic inflammation, the fetal and newborn insult is induced by additional uncultivated and difficult-to-cultivate species. Data supporting this premise has shown that 16S rDNA PCR technology improves the accuracy of culture-based methods for diagnosis of neonatal sepsis.[46]

In the context of the narrow spectrum of currently identifiable bacteria, attempts have been made to use physiologic parameters, such as hematologic indices and cytokine profiles, to identify neonates with sepsis and guide decisions related to initiation and duration of antibiotic treatment. Although the majority of the proposed cytokine markers (such as IL-6) have high negative predictive values (for ruling out sepsis), they have not been adopted for general use. This relates to the large volume of sample required (relative to the blood volume of a premature neonate), long interval to obtain the results (especially if ELISA techniques are used), high cost of tests and need for trained personnel. Hematologic indices on the other hand are readily achievable from a complete blood count and leukocyte differential assays. At Yale NBSCU results are available in 1 hour. Their disadvantages are the poor specificity for diagnosing culture proven sepsis and need for subjective interpretation. Applicant has developed a newborn hematological scoring system for EONS which in Applicant's clinical setting is used consistently to guide with antibiotic treatment. The Bhandari criteria are: absolute neutrophil count (ANC) <7,500/mL or >14,500/mL, absolute band count (ABC) >1,500/mL, immature/total neutrophil ratio (I:T) ratio >0.16, platelet count <150.000 cells/mm$^3$. Provided herein are methods to determine or to suspect the occurrence of sepsis in a newborn using one, two, three or four of the Bhandari criteria. In some embodiments, at least two criteria are used to determine or to suspect the presence of EONS, optionally further corroborated with one or more clinical manifestations. Per clinical protocol, at Yale NBSCU all infants with proven and suspected sepsis (by clinical and/or laboratory criteria) receive empiric antibiotherapy for at least 48 to 72 hours after which the indication is reevaluated. Therefore, there is an urgent need for improved diagnostic modalities of neonatal sepsis and of enabling technologies that can use either CB or minimal amounts of neonatal blood.

Another challenge posed in the diagnosis of EONS is its heterogeneous nature. This may thus explain why some neonates can manifest clinical symptoms or have hematological indices suggestive of EONS in the absence of a positive microbial culture results.[42,47,48] For instance, it is tempting to propose that there may not necessarily be a requirement for bacteria to passage live into fetal circulation to induce EONS manifestations. It would suffice for endotoxin, other bacterial products, lipophylic damage associated molecular pattern proteins (DAMPs) or just cytokines to "spill" from AF into the fetal circulation and cause manifestations consistent to septic shock. Evidence described herein supports this premise.

As described herein, Applicant has developed diagnostic proteomic profiles in AF and vaginal fluid characteristic of intra-amniotic inflammation and PTB.[49,50,51,52-53,54] Applicant used surface enhanced laser desorption ionization time-of-flight mass spectrometry (SELDI) and devised a novel, stepwise strategy based on mathematical filter preferences applied sequentially. This strategy was named mass restricted (MR) scoring. Four peaks (and thus the proteins they represent) were used to devise the MR score. The MR score ranges from 0 to 4, depending on the presence or absence of each of these 4 biomarkers. Proteomics identification techniques established that the component SELDI peaks corresponded to neutrophil defensin-2 (3.3 kDa), neutrophil defensin-1 (3.4 kDa), S100A12 (10.4 kDa) and S100A8 (10.8 kDa), all members of the innate immunity arm of antimicrobial defenses (3 or 4 peaks present of 4 possible) was highly successful in detecting intra-amniotic inflammation (90.1%). MR score has a unique ability to predict funisitis and EONS. In a prospective follow-up study Applicant observed a sequential appearance of biomarkers, as the process of intra-amniotic inflammation progresses from acute to chronic, with the peaks corresponding to the DAMPs S100A12 and S100A8 appearing last. This finding enabled stratification, based on severity of AF inflammation from MR 0 (absent) to MR 1-2 (mild) to MR 3-4 (severe) characterized by irreversible cellular injury.

Recent data from a prospective cohort of 132 consecutive mothers who had an amniocentesis to rule-out infection indicated that neonates of women with "severe" intra-amniotic inflammation by the MR score had higher CB IL-6 levels and a higher frequency of proven and suspected EONS. Of all newborns, 34 (26%) were clinically diagnosed with EONS, although only 6 (5%) of these had a positive blood culture. Overall, newborns with EONS had significantly elevated CB IL-6 levels, compared to those without sepsis when correcting for GA at birth. Yet, there was a wide margin of variation among CB IL-6 levels between individuals (newborns) from normal levels (despite positive AF culture and severe intra-amniotic inflammation by MR score), to extremely elevated concentrations (despite normal AF analysis). Wide variations in human cytokine levels data are frequently encountered in other studies and thus Applicant investigated in greater depth the reasons for this marked individual variation in newborns. The CB-to-AF IL-6 ratio (CB/AF IL-6; an indicator of the differential inflammatory response in the fetal versus the AF compartment) correlates with the MR score in a manner dependent on the severity of histological inflammation of the chorionic plate, chorio-decidua and umbilical cord (funistis). This finding suggests that inflammation-induced damage to the maternal-fetal interface may play a permissive role in cytokine trafficking between the AF and CB. In most EONS cases with evidence of severe intra-amniotic inflammation (88% of all EONS cases in the study), the absolute AF IL-6 concentration was significantly higher than that measured in CB. This suggests that should the maternal-fetal interface become damaged, the IL-6 gradient favors spillage into the fetal compartment. Yet, in a minority of EONS newborns, the CB/AF IL-6 reversed. This finding provided support for the conclusion that an outpouring of cytokines may occur in the fetal compartment independent of AF space. In fetuses with a reversed CB/AF IL-6 ratio, EONS confirmed by positive blood cultures reached 50%. It is possible that in the remaining 50% sepsis was induced by "uncultivated" bacteria or that these fetuses had a disproportionate activation of their innate immune response to bacterial products leaked into fetal circulation. Data in support of this premise is coming from the evidence that maternal antibiotic treatment, which results in killing of maternal bacteria, may induce excess release of endotoxin. In addition, data derived from animal models of sepsis show that antibiotic-treated rats display higher plasma endotoxin levels than untreated animals despite decreased bacteremia. Moreover, different antibiotics may induce the release of different forms of endotoxin which may be lethal for sensitized animals.[55] This may explain why attempts to prevent PTB with antibiotic treatment in patients with bacterial vaginosis, Trichomonas or preterm labor either had no effect or paradoxically increased the rate of PTB.

For the last 3 decades obstetricians, neonatologists and developmental neurobiologists had debates regarding the appropriate time to deliver a fetus exposed to a hostile intrauterine environment. In the absence of either a preventive or curative therapy for intra-amniotic infection and inflammation the answers to questions such as how much of an inflammatory stress can each fetus withstand or whether there is time to wait for a complete course of steroid when infection/inflammation is diagnosed remain rhetorical. A key to providing answers to all these questions is discovery of biomarkers highly predictive of fetal and, neonatal outcome. The work and method described herein offer a new opportunity to provide evidence-based answers to several of the above queries.

There will be a clinical and economic impact of a rapid method that makes it possible to improve identification of EONS and other complications of PTB. Early initiation of antibiotic treatment in the neonatal period has been shown to reduce mortality due to sepsis.[56] However, as described herein, antibiotic treatment remains contingent on early identification of signs of infection, which is a difficult task. Given that even a 4-hour delay may increase mortality rate and the fact that it takes at least 48 to 72 hours until bacterial growth can be confirmed, NICUs around the world initiate "empirical antibiotic therapy" in all cases of suspected EONS immediately after microbial cultures have been obtained.[57] This treatment is intended to cover both Gram-negative and Gram-positive bacteria, generally through a combination of an aminoglycoside (i.e., gentamicin) and a beta-lactam antibiotic (i.e., penicillin or ampicillin).[58] A study that evaluated the duration of therapy for suspected, but not proven, sepsis found that antibiotic administration in NICUs across the U.S. is highly inconsistent, lasting approximately 2-3 days in most cases, but extending to 10 days for some neonates.[59] This non-discriminatory practice adds significant cost from use of NICUs, specialized nursing, physician and pharmacy resources, in addition to sometimes prohibitive drug costs.

For the late preterm and term infants admitted in NICUs for sepsis evaluation and/or antibiotic treatment the benefits of a tool to 'rule-out EONS' and to discriminate among pathophysiological EONS variants is cost beneficial and can be incorporated into the hospital setting without delay. In addition to decreasing the length of stay reducing hospital costs, such tool will facilitate infant-parental attachments and successful establishment of breast-feeding, as well as lower the risks of exposure to resistant microorganisms frequently encountered in the setting of prolonged hospitalization.

Hp and HpRP

Hp is an acute phase glycoprotein with a great variety of important biological functions, of which the most recognized is hemoglobin binding.[60] Hp is a tetrameric protein of two $\alpha$ and two $\beta$ chains derived from a single mRNA that encodes a precursor that is cleaved post-translationally to generate the two chains. The liver is the main site of Hp synthesis, although Hp synthesis has been demonstrated many extrahepatic sites such as adipose tissue, lung, ovary, testis, arteries and placenta. However, beyond its role as a hemoglobin scavenger, Hp is also a stimulator of angiogenesis and an inhibitor of prostaglandin synthesis.[61] Importantly, Hp plays a vital role in regulating innate host defense mechanisms, which is consistent with a global immunosuppressive and antioxidant function.[62] Hp blocks neutrophil responses by binding directly to neutrophils and inhibiting their oxidative burst. Hp also inhibits lymphocyte transformation and decreases antibody production.[63] Hp has a direct bacteriostatic activity by limiting utilization of iron by adventitious bacteria.[64] There is evidence to support a key role of Hp in modulating immune mechanisms at the materno-fetal interface by regulating NK-decidual cell interaction.[65] However, the extent to which Hp satisfies these functions is subjected to significant phenotypic and developmental variation.

In humans, but not in other mammals, Hp has been shown to occur in two allelic forms, Hp1 and Hp2, which differ in the length of the $\alpha$-chain. The longer $\alpha$-chain (in Hp2) seems to have arisen by an internal duplication of a gene segment coding for almost the entire $\alpha$-chain of Hp1.[66] The human population has 3 major haptoglobin phenotypes (Hp1-1, Hp2-2 and the heterozygous type 2-1) derived from variations in the $\alpha$-chain with identical $\beta$-chains.[67] Hp1 has two additional allelic variations $Hp1^{Fast}$ and $Hp1^{Slow}$ which code for $\alpha$-chains of equal length but different charge and generate minor phenotypic differences among carriers.

The complex evolution of the human Hp gene cluster offers the classical example of how rearrangements in parts of existing genes can generate new genes coding for new proteins which confer survival advantages in certain stressing environments. Highly conserved homologs to Hp1 allele are found in all mammals. The Hp2 allele is found only in humans and is believed to have arisen ~100,000 years ago early in human evolution. Today Hp2 allele frequency is higher that Hp1 allele frequency in nearly every ethnic group and geographic area and continues to increase, suggesting that the driving force for this positive selection continues to be present. It has been hypothesized that the ability of Hp2 allele to spread so rapidly in humans was due to its ability to provide a selective advantage against life-threatening infectious diseases which was the dominant environmental pressure early in human evolution. It is postulated that the severe environmental challenge of *Plasmodium falciparum* infection has resulted in emergence of Hp 2-2 phenotype in malaria endemic environments to boost Th1 cytokine and oxidative responses to which the parasite is vulnerable in a somewhat similar manner to sickle cell trait.[68]

Hp posses a phenotype-dependent antioxidant activity that exceeds by far that of vitamin C.[69] However, Hp2-2 has a lesser anti-oxidant capacity, compared to that of Hp1-1, due to the lower affinity of Hp2-2 for free hemoglobin. Moreover, Hp2-2, but not Hp1-1, has been shown to have direct antimicrobial activity in vitro. Hp2-2 binds to the *streptococcus* T antigen, thereby resulting in its aggregation and slowing its growth. Recently, there has been an increasing interest in relationships of Hp phenotypes and individual variation in susceptibility to infectious diseases versus susceptibility to chronic diseases with pro-inflammatory and oxidative component. Several studies demonstrate that individuals homozygous for the Hp1 allele (Hp1-1) are more susceptible to acquire infectious diseases, such as malaria, streptococcal or staphylococcal infections. This is in contrast to Hp2 allele carriers (Hp 2-1 or Hp2-2 phenotypes), who display resistance. These individuals, however, seem to have increased risk of diseases with oxidative and inflammatory mediated-tissue damage[70,71,72] of either infectious (pulmonary tuberculosis, HIV) or non-infectious etiology (diabetes, arteriosclerosis, coronary disease).

An important regulator of Hp expression is the inflammatory cytokine Hepatic Hp synthesis is dependent on cis-acting elements localized within the first 186 bp of the 5'-flanking region of the promoter. Interaction of this promoter site with trans-acting elements is postulated to provide a second level of complexity in regulation of Hp expression, which further explains why in individuals with the same genotype, Hp levels vary with exposure to environmental or epigenetic stressors (physical effort, methylation status).[73] It is known for adults that haptoglobin concentration measured by ELISA is phenotype-dependent. The reference range for haptoglobin concentration is lower in individuals carrying the Hp2-2 phenotype than individuals carrying the Hp1-1 and Hp2-1 phenotype. Therefore, Hp2-2 phenotype confers a state of relative ahaptoglobinemia. Few individuals may lack both Hp alleles, giving raise to Hp0-0 phenotype. In the US adult population ahaptoglobinemia varies from 0.1% in Caucasians to much higher frequency 4% in African-Americans.

Another interesting feature is that in humans, the entire Hp gene is itself duplicated as Hp-related (HpRP) gene, which also contains elements of retroviral insertion. The transcription of the HpRP gene generates 21 kDa protein, but is silenced in the adult liver through an unknown mechanism. However, based on published reports, the human serum, breast carcinoma, decidua and placenta are four compartments where the HpRP protein product appears expressed. At amino-acid level HpRP is 90% identical with Hp, which explains cross-reactivity in Western blots and ELISA assays with most available antibodies.[74] Other than conferring innate immunity to humans against *Trypanosoma brucei*, the function of HpRP protein remains a unknown.[75] Recently, expression of HpRP has been implicated an oncofetal tumor marker in breast cancer.

Applicant has shown that Hp and HpRP levels in CB of newborns with EONS are elevated, which is remarkable, in view of the well established developmental regulation of Hp transcription and the evidence that in normal term newborns, Hp is absent at birth. Normal levels of Hp in newborns at term are measured at <2 mg/dL (clinical assay limit) and the switch to the adult level of 100-150 mg/dL occurs within the first year of life.[76] The mechanism responsible for Hp gene silencing in the fetal developmental period and its activation switch in the adult life remains unknown. The presence and levels of HpRP in CB, have not previously been established. Hp and HpRP are referred to herein as components of Hp. Using ELISA, Applicant confirmed that a group of 7 healthy term newborns had undetectable CB Hp and HpRP and their mothers had levels of ~100 µg/mL.

Figure 15:
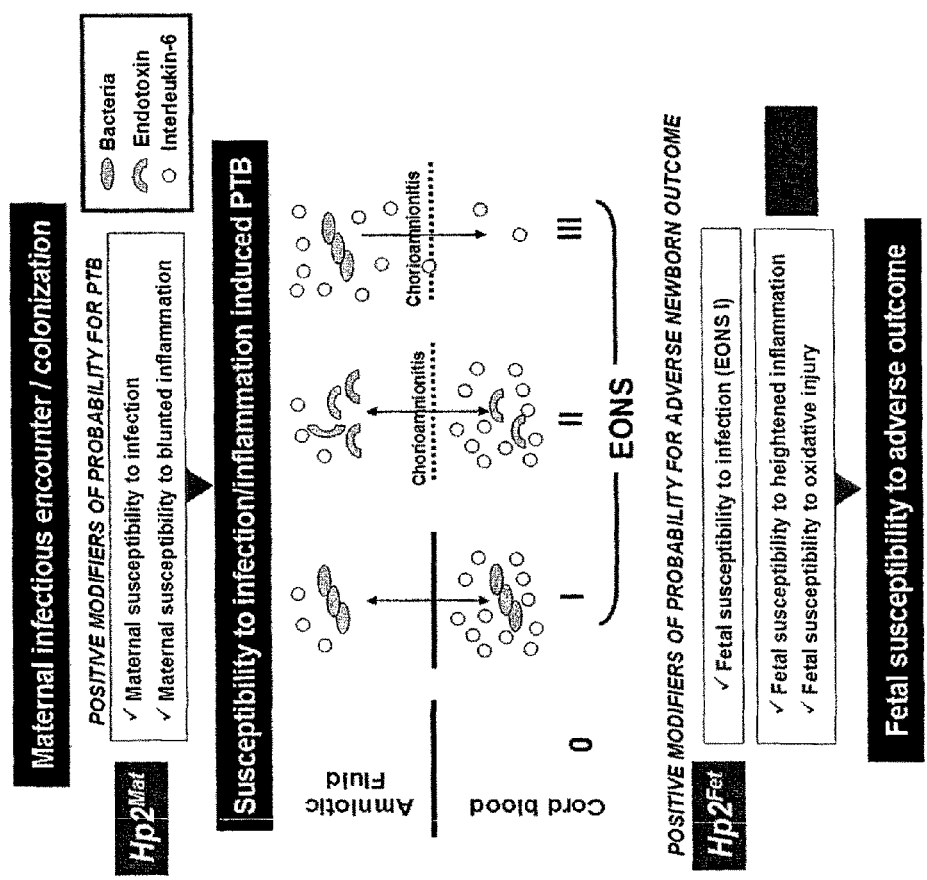
FIG. 15 shows a working model of how interactions of environmental stressors (bacteria) with genetically determined Hp phenotypes may impact on susceptibility to PTB and adverse neonatal outcomes. Positive modifiers facilitate disease progression. For each, Applicant postulated how maternal (Mat) or fetal (Fet) carriage of Hp2 allele will impact on disease susceptibility (red) vs. resistance (blue). The proposed pathogenic variants of EONS are differentiated as EONS 0 (lack thereof), EONS I (passage of a live bacterial inoculum to the fetus), EONS II (passage of endotoxin, other bacterial products or DAMPs through a damaged maternal-fetal interface) and EONS III (spillage of inflammatory cytokines only).

As described herein, Applicant has shown that an elevated Hp level at birth is a predictor of EONS (independent of GA) and of the composite outcome variable IVH and death (independent of EONS). Applicant's results are consistent with the current knowledge on the significance of genetically determined Hp phenotypes for susceptibility to infectious diseases (Hp0-0>Hp1-1>Hp2-1>Hp2-2) versus susceptibility to inflammation-induced oxidative stress and cellular damage (Hp2-2>Hp2-1>Hp1-1>Hp0-0), led Applicant to formulate the hypothesis that interactions of environmental stressors (bacteria) with genetically determined variations in haptoglobin phenotypes and/or haptoglobin levels are critical determinants of susceptibility to adverse neonatal outcomes. A schematic representation of this view is shown in FIG. 15. Based on assessment of Hp switching (from absent to adult level) in CB, a rapid diagnostic test for EONS is available. The methods described herein improve existing point-of-care technologies that seek to detect EONS at birth (analysis of CB Hp and/or HpRP signatures) and monitor thereafter sepsis in preterm newborns (analysis of neonatal blood). Useful here is a biosensor technology which has attributes to differentiate among pathogenic EONS variants, thus enabling a "theranostic" (diagnostics+targeted therapy) treatment, in which one "treatment" is no treatment e.g., no antibiotic therapy. This approach may result in substantial health care savings. One strategy utilizes SELDI-TOF, which has the potential to provide a rapid modality for individual Hp phenotyping. Other assays are known in the art. Together with evidence of exposure to infection (positive Hp switching), SELDI-TOF or other methods could be used at birth in each premature newborn to estimate risk of developing EONS, IVH and other major complications of premature birth. A significant advantage is that Hp subtyping is a well-established forensics method. In old blood spots, Hp forms adducts with hemoglobin which render the protein resistant to degradation. Hp may be detected in archived Guthrie cards, dried fingerstick spots and CB spots.

Platforms to Evaluate Hp and HpRP Signatures

In preliminary experiments Applicant confirmed the ability to detect differences among Hp and Hp signatures in CB using ELISA and western blot. Western blot results correlate strongly with densitometric analysis of westerns (P>0.001, suggesting that normalization for total protein may not be required). However for a rapid diagnosis other technologies may further facilitate detection of Hp and HpRP signatures for point-of-care in Labor and Birth and NICUs. An advantage of SELDI-TOF is the antibody-independent separation and the high resolution which enables detection not only of the major but also minor Hp phenotypes. An important step for separation in mass spectrometry is breaking the bonds among Hp chains and among Hp and hemoglobin through stringent reducing conditions. The results could be available within 1 hour reliant on availability of a SELDI-TOF mass spectrometer.

Furthermore, it is also possible to carry out methods described herein using analytical instruments based on AMMP technology, a hybrid variant of surface plasmon resonance and MEMS sensors. This cutting-edge technology offers the promise to provide the needed speed for simultaneous quantitative information for Hp and HpRP, IL-6 and bacterial fingerprints (endotoxin) within the same CB sample. The company has already validated the platform for bacteria (whole bacterial cells and endotoxin) and IL-6 measurement in adult whole blood. One approach that can be used is concurrent assessment of Hp and HpRP (using the same antibody validated by Applicant in ELISA and western blots) and IL-6 within the same sensitivity range.

It is likely that in most newborns with EONS, Hp and HpRP levels will exceed by several orders of magnitude those of IL-6, while in a minority of cases IL-6 will far exceed Hp and HpRP. Both these scenarios will prompt a need for intervention. This information would thus suffice for point-of-care enabling of a theranostic approach within 1 hour of birth, which can be followed by a clinical laboratory type analysis (Western blot, SELDI or other techniques) to determine the phenotype and compute the risk assessment.

"Antenatal switching" or Hp switching, as used herein, can be assessed, for example by western blot, with the appearance of ~40 kDa Hp and/or HpRP bands (corresponding to the beta-chain) and optionally accompanied by one or two additional bands that are Hp and/or HpRP specific. Full term newborns have essentially no Hp and normal levels of Hp and/or HpRP in newborns are considered undetectable and below clinical assay limits. Applicant showed that when employing the same polyclonal antibody which detects all three polypeptide bands specific for Hp and/or HpRP in paired ELISA and western blot assays, a determination of switched Hp could be made when a signal (or assay value) is measured that is above a pre-established cut-off. The cut-off for the signal (or assay value) upon which a determination can be made may vary with method sensitivity depending on the assay. For example, a determination of switched Hp and/or HpRP obtained from visual inspection of a western blot may, under the conditions used, correspond to an immunoreactivity level above 3,370 ng/mL in ELISA immunoreactivity (>3.37 micrograms/mL). A similar analysis in a group of 19 normal term newborns (controls) measured an immunoreactivity level (for ELISA) ranging from 1.9 to 0.9 micrograms/mL with none exhibiting switching based on visual inspection of western blots. In contrast, the control mothers all showed a switched Hp and/or HpRP signature and the measured level in ELISA ranged from 909-63 micrograms/mL. In certain assays, minimum detection levels can be around 2 mg/dl of protein and an analyte (e.g. a protein) is considered undetectable if the concentration is below the detection limit. Normal levels of newborns at term are at undetectable levels. In newborns with uncomplicated pregnancy and delivery the switch to adult levels of about 100-150 mg/dL occurs within the first year of life.

In certain embodiments, antibodies are provided that are specific for Hp and/or HpRP or cytokines, such as IL-6 or other biomarkers described herein, for example, those listed in Table 2 and neutrophil defensin-1 and -2, S100A12 and S100A8, found in fluid samples of a fetus or newborn. Antibodies provided herein include polyclonal and monoclonal antibodies, as well as antibody fragments and derivatives that contain the relevant antigen binding domain of the antibodies. The term "antibody" as used herein refers to immunoglobulin molecules or other molecules which comprise at least one antigen-binding domain. The term "antibody" as used herein is intended to include whole antibodies (e.g. IgG, IgA, IgE, IgM, or IgD), monoclonal antibodies, polyclonal antibodies, chimeric antibodies, humanized antibodies, primatized antibodies, multi-specific antibodies, single chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, and totally synthetic and recombinant antibodies.

Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Monoclonal antibodies may be produced in animals such as mice and rats by immunization. B cells can be isolated from the immunized animal, for example from the spleen. The isolated B cells can be fused, for example with a myeloma cell line, to produce hybridomas, that can be maintained indefinitely in in vitro cultures. These hybridomas can be isolated by dilution (single cell cloning) and grown into colonies. Individual colonies can be screened for the production of antibodies of uniform affinity and specificity. Hybridoma cells may be grown in tissue culture and antibodies may be isolated from the culture medium. Hybridoma cells may also be injected into an animal, such as a mouse, to form tumors in vivo (such as peritoneal tumors) that produce antibodies that can be harvested as intraperitoneal fluid (ascites). The lytic complement activity of serum may be optionally inactivated, for example by heating.

For example, specific proteins, peptides, haptens, and chemical compounds may be used to generate antibodies. One skilled in the art will recognize that the amount of polypeptides used for immunization will vary based on a number of factors, including the animal which is immunized, the antigenicity of the polypeptide selected, and the site of injection. The polypeptides used as an immunogen may be modified as appropriate or administered in an adjuvant in order to increase the peptide antigenicity. In some embodiments, polypeptides, peptides, haptens, and small compounds may be conjugated to a carrier protein to elicit an immune response or may be administered with and adjuvant, e.g. incomplete Freund's adjuvant.

Suitable methods to increase antigenicity are well known in the art, and include, for example, coupling the antigen with a heterologous protein (such as globulin or β-galactosidase) or through the inclusion of an adjuvant during immunization.

Antibody titers can be monitored e.g., by antigen-specific ELISA, western blot analysis, or radioimmunoassay. One or more animals are commonly used for antibody production. Antibodies or immunospecific fragments thereof of provided herein may be from any animal origin including rabbits, sheep, goats, chicken, mice, rats, hamsters, guinea pigs, donkey, camel, llama, or horse.

After one or more injections of the antigen, approximately 7-10 days after each boost, serum may be taken to determine the production of specific antibodies (titer). The test bleeds may be assayed against the immunogen itself, for example in an ELISA assay. Antibodies may be stored in several different buffers, for example at neutral pH, such as 0.01 M phosphate-buffered saline (PBS) at pH 7.4, optionally containing, for example 0.1% sodium azide to inhibit microbial growth. For long-term storage, antibodies may be kept at a low temperature, such as 4° C., −20° C. or −70° C. Antibodies may be stored at >0.5 mg/mL and/or in the presence of a carrier protein (e.g., 1% bovine serum albumin (BSA)), or if frozen, for example in 50% glycerol.

Protocols for generating antibodies, including preparing immunogens, immunization of animals, and collection of antiserum may be found in Antibodies: A Laboratory Manual, E. Harlow and D. Lane, ed., Cold Spring Harbor Laboratory (Cold Spring Harbor, N.Y., 1988) pp. 55-120 and A. M. Campbell, Monoclonal Antibody Technology: Laboratory Techniques in Biochemistry and Molecular Biology, Elsevier Science Publishers, Amsterdam, The Netherlands (1984).

The term "antibody fragment" as used herein is intended to include any appropriate antibody fragment which comprises an antigen-binding domain that displays antigen binding function. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab[1] fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. Antibody fragments, including single-chain antibodies, may comprise the variable region(s) alone or in combination with the entirety or a portion of the following: hinge region, CH1, CH2, and CH3 domains.

In some aspects, the antibody or antibody fragment comprises an antibody light chain variable region (VL) and an antibody heavy chain variable region (VH) which generally comprise the antigen binding site. In certain embodiments, the antibody or antibody fragment comprises all or a portion of a heavy chain constant region, such as an IgG1, IgG2, IgG3, IgG4, IgA1, IgA2, IgE, IgM or IgD constant region. In some aspects, the heavy chain constant region is an IgG1 heavy chain constant region, or a portion thereof. Furthermore, the antibody or antibody fragment may comprise all or a portion of a kappa light chain constant region or a lambda light chain constant region, or a portion thereof. In some aspects, the light chain constant region is a lambda light chain constant region, or a portion thereof. All or part of such constant regions may be produced naturally or may be wholly or partially synthetic. Appropriate sequences for such constant regions are well known and documented in the art.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). It will be understood by one of ordinary skill in the art that these domains (e.g., the heavy chain portions) may be modified such that they vary in amino acid sequence from the naturally occurring immunoglobulin molecule.

As used herein, the term "light chain portion" includes amino acid sequences derived from an immunoglobulin light chain. Preferably, the light chain portion comprises at least one of a VL or CL domain.

Recombinant techniques are preferred for generating large quantities of antibodies, antibody fragments and single chain antibodies. In general, recombinant production of antibodies, antibody fragments or derivatives thereof, uses mRNA encoding an antibody which is isolated from hybridoma cells that produce the desired antibody. This mRNA is used as a source for generating a cDNA molecule which encodes the antibody, or a fragment thereof. Once obtained, the cDNA may be amplified and expressed according to known methods in a variety of eukaryotic and prokaryotic hosts.

In certain embodiments, antibody derivatives are provided. As used herein, "antibody derivatives" contain an antibody or a fragment thereof, as well as an additional moiety. Such moieties may improve the solubility, absorption, biological half-life, etc., of the antibody, decrease the toxicity of the antibody in vivo or in vitro, eliminate or attenuate any undesirable side effect of the antibody in vivo, or serve as a detectable marker of the presence of the antibody. Moieties capable of mediating such effects are well known in the art. In certain embodiments, detectably labeled antibodies are provided. An antibody is referred to as "detectably labeled" if the antibody, or fragment thereof, is attached to a molecule which is capable of identification, visualization, or localization using known methods. Suitable detectable labels include radioisotopic labels, enzyme labels, non-radioactive isotopic labels, fluorescent labels, toxin labels, affinity labels, and chemiluminescent labels.

Biomarkers of the invention can be measured in different types of biological samples, preferably biological fluid samples such as blood. Examples of biological fluid samples that may be used in methods of the invention, although not intended to be limiting, include cord blood, neonatal blood, cerebral spinal fluid, tears, saliva, urine, feces, and meconium. If desired, a sample can be prepared to enhance detectability of the biomarkers. For example, a sample from the subject can be fractionated. Any method that enriches for a biomarker polypeptide of interest can be used. Sample preparations, such as prefractionation protocols, are optional and may not be necessary to enhance detectability of biomarkers depending on the methods of detection used. For example, sample preparation may be unnecessary if an antibody that specifically binds a biomarker is used to detect the presence of the biomarker in a sample. Sample preparation may involve fractionation of a sample and collection of fractions determined to contain the biomarkers. Methods of prefractionation include, for example, size exclusion chromatography, ion exchange chromatography, heparin chromatography, affinity chromatography, sequential extraction, gel electrophoresis and liquid chromatography. Examples of methods of fractionation are described in PCT/US03/00531 (incorporated herein in its entirety).

As an example, a sample is pre-fractionated by anion exchange chromatography. Anion exchange chromatography allows pre-fractionation of the proteins in a sample roughly according to their charge characteristics. For example, a Q anion-exchange resin can be used, and a sample can be sequentially eluted with eluants having different pHs. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

As another example, biomolecules in a sample can be separated by high-resolution electrophoresis, e.g., one or two-dimensional gel electrophoresis. A fraction containing a biomarker can be isolated and further analyzed by gas phase ion spectrometry. Preferably, two-dimensional gel electrophoresis is used to generate two-dimensional array of spots of biomolecules, including one or more biomarkers. See, e.g., Jungblut and Thiede, Mass Spectr. Rev. 16:145-162 (1997). The two-dimensional gel electrophoresis can be performed using methods known in the art. See, e.g., Deutscher ed., Methods In Enzymology vol. 182. In certain cases, biomolecules in a sample are separated by, e.g., isoelectric focusing, during which biomolecules in a sample are separated in a pH gradient until they reach a spot where their net charge is zero (isoelectric point). This first separation step results in one-dimensional array of biomolecules. The biomolecules in one-dimensional array is further separated using a technique generally distinct from that used in the first separation step. Typically, two-dimensional gel electrophoresis can separate chemically different biomolecules in the molecular mass range from 1000-200,000 Da within complex mixtures. The pI range of these gels is about 3-10 (wide range gels).

As another example, high performance liquid chromatography (HPLC) can also be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more biomarkers can be collected. The fraction can then be analyzed by gas phase ion spectrometry to detect biomarkers. For example, the spots can be analyzed using either MALDI or SELDI as described herein.

Optionally, a biomarker can be modified before analysis to improve its resolution or to determine its identity. For example, the biomarkers may be subject to proteolytic digestion before analysis. Any suitable protease may be used. Proteases, such as trypsin, that are likely to cleave the biomarkers into a discrete number of fragments are particularly useful. The fragments that result from digestion may function as a fingerprint for the biomarkers, thereby enabling their detection indirectly. This is particularly useful where there are biomarkers with similar molecular masses that might be confused for the biomarker in question. Also, proteolytic fragmentation is useful for high molecular weight biomarkers because smaller biomarkers are more easily resolved by mass spectrometry. Optionally, the identity of the biomarkers can be further determined by matching the physical and chemical characteristics of the biomarkers in a protein database (e.g., SwissProt).

Optionally samples containing biomarkers can be treated with one or more stabilizing agent and the container used for collection of the sample(s) may be pretreated with one or more stabilizing agent prior to measuring the levels of biomarkers. The term "stabilizing agent" refers to one or more molecules, such as polypeptides or nucleic acids, that can be used to prevent the degradation of the biomarkers. In one embodiment, the stabilizing agent is a protease inhibitor, including any of 4-(2-Aminoethyl) benzenesulphonyl fluoride (AEBSF) and Pefabloc SC, Antipain and Antipain-dihydrochloride, Aprotinin, Benzamidine and Benzamidine hydrochloride, Bestatin, Chymostatin, E-64 (L-trans-epoxysuccinyl-leucylamide-(4-guanido)-butane or N—[N-(L-trans-carboxyoxiran-2-carbonyl)-L-leucyl]-agmatine), Ethylenediaminetetraacetic acid and its sodium salt (EDTA-Na2), Leupeptin, Ethylmaleimide, Pepstatin and Pepstatin A, Phosphoramidon, Sodium azide, Trypsin inhibitor or E-aminocaproic acid.

Levels of a biomarker discussed herein that is useful in a method of the present invention (e.g., Hp and/or HpRP, IL-6) may be assessed by any of a wide variety of well known methods for detecting expression of a transcribed molecule or its corresponding protein. Non-limiting examples of such methods include immunological methods for detection of secreted proteins, protein purification methods, protein function or activity assays, nucleic acid hybridization methods, nucleic acid reverse transcription methods, and nucleic acid amplification methods. In one embodiment, levels of a biomarker is assessed using an ELISA assay. Resulting values may be compared to a control or known (pre-established) standard. As used herein, the term "control" refers to the levels of the biomarker in a sample obtained from a reference subject.

Biomarkers such as Hp and/or HpRP and IL-6 are preferably captured with capture reagents immobilized to a solid support, such as any biochip described herein, a multiwell microtiter plate, a resin, or other suitable support. A preferred mass spectrometric technique for use in the invention is Surface Enhanced Laser Desorption and Ionization (SELDI), as described, for example, in U.S. Pat. No. 5,719,060 and U.S. Pat. No. 6,225,047, in which the surface of a probe that presents the analyte to the energy source plays an active role in desorption/ionization of analyte molecules. In this context, the term "probe" refers to a device adapted to engage a probe interface and to present an analyte to ionizing energy for ionization and introduction into a gas phase ion spectrometer, such as a mass spectrometer. A probe typically includes a solid substrate, either flexible or rigid, that has a sample-presenting surface, on which an analyte is presented to the source of ionizing energy.

One version of SELDI, called "Surface-Enhanced Affinity Capture" or "SEAC," involves the use of probes comprised of a chemically selective surface ("SELDI probe"). A "chemically selective surface" is one to which is bound either the adsorbent, also called a "binding moiety," or "capture reagent," or a reactive moiety that is capable of binding a capture reagent, e.g., through a reaction forming a covalent or coordinate covalent bond.

The phrase "reactive moiety" here denotes a chemical moiety that is capable of binding a capture reagent. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact noncovalently with histidine containing peptides. A "reactive surface" is a surface to which a reactive moiety is bound. An "adsorbent" or "capture reagent" can be any material capable of binding a biomarker of the invention. Suitable adsorbents for use in SELDI, according to the invention, are described in U.S. Pat. No. 6,225,047.

One type of adsorbent is a "chromatographic adsorbent," which is a material typically used in chromatography. Chromatographic adsorbents include, for example, ion exchange materials, metal chelators, immobilized metal chelates, hydrophobic interaction adsorbents, hydrophilic interaction adsorbents, dyes, mixed mode adsorbents (e.g., hydrophobic attraction/electrostatic repulsion adsorbents). "Biospecific adsorbent" is another category, for adsorbents that contain a biomolecule, e.g., a nucleotide, a nucleic acid molecule, an amino acid, a polypeptide, a simple sugar, a polysaccharide, a fatty acid, a lipid, a steroid or a conjugate of these (e.g., a glycoprotein, a lipoprotein, a glycolipid). In certain instances, the biospecific adsorbent can be a macromolecular structure such as a multiprotein complex, a biological membrane or a virus. Illustrative biospecific adsorbents are antibodies, receptor proteins, and nucleic acids. A biospecific adsorbent typically has higher specificity for a target analyte than a chromatographic adsorbent.

Another version of SELDI is Surface-Enhanced Neat Desorption (SEND), which involves the use of probes comprising energy absorbing molecules that are chemically bound to the probe surface ("SEND probe"). The phrase "Energy absorbing molecules" (EAM) denotes molecules that are capable of absorbing energy from a laser desorption ionization source and, thereafter, contributing to desorption and ionization of analyte molecules in contact therewith. The EAM category includes molecules used in MALDI, frequently referred to as and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. The category also includes EAMs used in SELDI, as enumerated, for example, by U.S. Pat. No. 5,719,060.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light. For instance, see U.S. Pat. No. 5,719,060. SEPAR and other forms of SELDI are readily adapted to detecting a biomarker or biomarker profile, pursuant to the present invention.

The detection of the biomarkers according to the invention can be enhanced by using certain selectivity conditions, e.g., adsorbents or washing solutions. The phrase "wash solution" refers to an agent, typically a solution, which is used to affect or modify adsorption of an analyte to an adsorbent surface and/or to remove unbound materials from the surface. The elution characteristics of a wash solution can depend, for example, on pH, ionic strength, hydrophobicity, degree of chaotropism, detergent strength, and temperature.

In some embodiments of the invention, a sample is analyzed by means of a "biochip," a term that denotes a solid substrate having a generally planar surface, to which a capture reagent (adsorbent) is attached. Frequently, the surface of a biochip comprises a plurality of addressable locations, each of which has the capture reagent bound there. A biochip can be adapted to engage a probe interface and, hence, function as a probe, which can be inserted into a gas phase ion spectrometer, preferably a mass spectrometer. Alternatively, a biochip of the invention can be mounted onto another substrate to form a probe that can be inserted into the spectrometer.

A variety of biochips is available for the capture of biomarkers, in accordance with the present invention, from commercial sources such as Ciphergen Biosystems (Fremont, Calif.), Packard BioScience Company (Meriden, Conn.), Zyomyx (Hayward, Calif.), and Phylos (Lexington, Mass.). Exemplary of these biochips are those described in U.S. Pat. Nos. 6,225,047, 6,329,209, and in PCT Publication Nos. WO 99/51773 and WO 00/56934.

A substrate with an adsorbent is contacted with the urine sample for a period of time sufficient to allow biomarker that may be present to bind to the adsorbent. After the incubation period, the substrate is washed to remove unbound material. Any suitable washing solutions can be used; preferably, aqueous solutions are employed. An energy absorbing molecule then is applied to the substrate with the bound biomarkers. As noted, an energy absorbing molecule is a molecule that absorbs energy from an energy source in a gas phase ion spectrometer, thereby assisting in desorption of biomarkers from the substrate. Exemplary energy absorbing molecules include, as noted above, cinnamic acid derivatives, sinapinic acid and dihydroxybenzoic acid. Preferably sinapinic acid is used.

Once captured on a substrate, e.g., biochip or antibody, any suitable method can be used to measure one or more biomarkers in a sample. For example, biomarkers can be detected and/or measured by a variety of detection methods including for example, gas phase ion spectrometry methods, optical methods, electrochemical methods, atomic force microscopy and radio frequency methods. Using these methods, one or more biomarkers can be detected.

In one embodiment, methods of detection and/or measurement of the biomarkers use mass spectrometry and, in particular, SELDI. SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above.

Another method for detection of biomarkers employs acoustic membrane microparticle (AMMP) resonance, a variant of surface plasmon resonance spectroscopy (Bioscale, Cambridge, Mass.) as described, for example in e.g., US2009-0148857 and US2007-0281371.

In another embodiment, an immunoassay can be used to detect and analyze biomarkers in a sample. An immunoassay is an assay that uses an antibody to specifically bind an antigen (e.g., a biomarker). An immunoassay is characterized by the use of specific binding properties of a particular antibody to isolate, target, and/or quantify the antigen. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a biomarker from specific species such as rat, mouse, or human can be selected to obtain only those polyclonal antibodies that are specifically reactive with that biomarker and not with other proteins, except for polymorphic variants and alleles of the biomarker. This selection may be achieved by subtracting out antibodies that cross-react with the biomarker molecules from other species.

Using purified biomarkers or their nucleic acid sequences, antibodies that specifically bind to a biomarker (e.g., Hp and/or HpRP) can be prepared using any suitable methods known in the art. See, e.g., Coligan, Current Protocols in Immunology (1991); Harlow & Lane, Antibodies: A Laboratory Manual (1988); Goding, Monoclonal antibodies: Principles and Practice (2d ed. 1986); Kohler & Milstein, Nature 256:495-497 (1975); Huse et al., Science 246:1275-1281 (1989); Ward et al., Nature 341:544-546 (1989).

Generally, a sample obtained from a subject can be contacted with the antibody that specifically binds the biomarker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or a protein chip.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads, fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the biomarker in the sample can be detected using an indirect assay, wherein, for example, a second, labeled antibody is used to detect bound biomarker-specific antibody, and/or in a competition or inhibition assay wherein, for example, a monoclonal antibody which binds to a distinct epitope of the biomarker is incubated simultaneously with the mixture.

Methods for measuring the amount or presence of an antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Useful assays are well known in the art, including, for example, an enzyme immune assay (EIA) such as enzyme-linked immunosorbent assay (ELISA), a radioimmune assay (RIA), a Western blot assay, or a slot blot assay.

Immunoassays can be used to determine presence or absence of a biomarker in a sample as well as the quantity of a biomarker in a sample. The amount of an antibody-marker complex can be determined by comparing to a standard. A standard can be, e.g., a known compound or another protein known to be present in a sample. It is understood that the test amount of biomarker need not be measured in absolute units, as long as the unit of measurement can be compared to a control.

When the sample is measured and data is generated, e.g., by mass spectrometry, the data may then be analyzed by a computer software program. In certain cases, a biomarker bound to the substrate can be detected in a gas phase ion spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Generally, data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set as zero in the scale.

A computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen, in another useful format, two or more spectra are compared, conveniently highlighting unique biomarkers and biomarkers that are up- or down-regulated between samples. Using any of these formats, one can readily determine whether a particular biomarker is present in a sample.

Software used to analyze the data can include code that applies an algorithm to the analysis of the signal to determine whether the signal represents a peak in a signal that corresponds to a biomarker according to the present invention.

EXAMPLES

Example 1

Proteomic Study of Cord Blood Obtained from Newborns

This example describes proteomic assessment of cord blood and results of that assessment.

Figure 13:
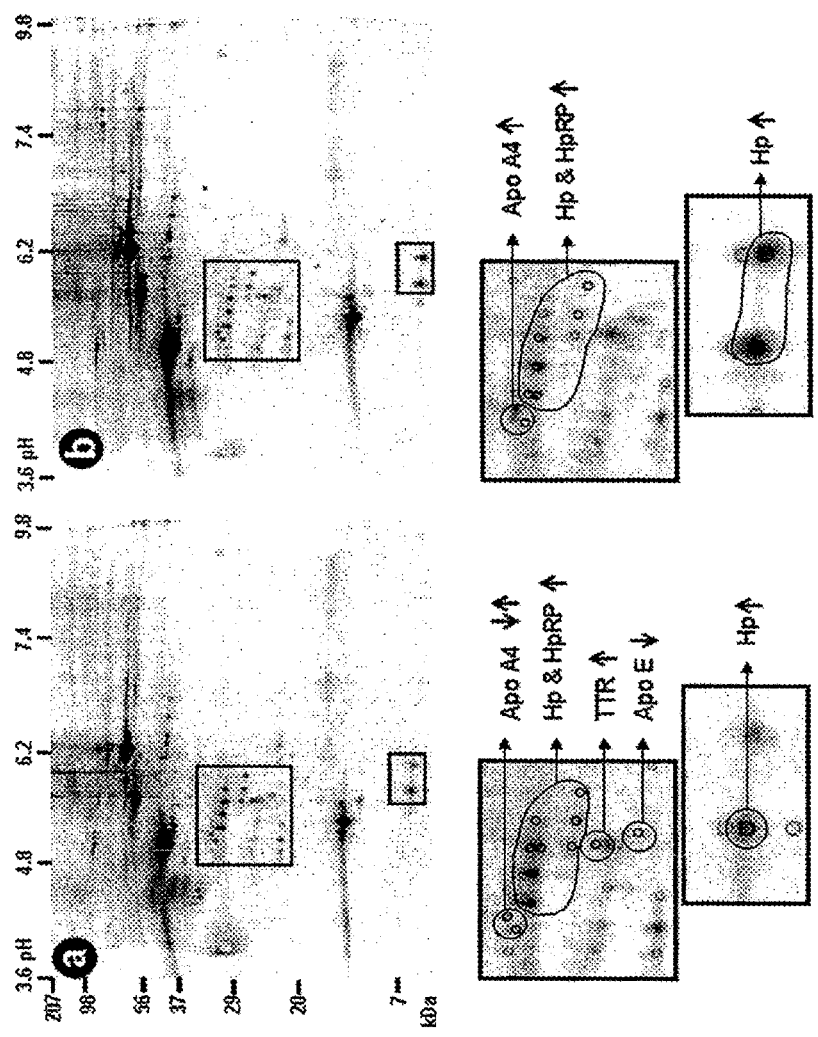
FIGS. 13a and 13b show 2D-DIGE gels obtained with cord serum from two newborns with EONS I and two with EONS 0, matched for GA at birth (28±1 wk). Nine proteins were differentially expressed >3-fold in at least 2 of 3 of the gels. They were either up-regulated or down-regulated. Different spots matching to the same precursor could appear both up and down-regulated, as shown for ApoA4. TTR (transthyretin) exceeded the cut-off on a single gel (A) and thus was not classified as biomarker by Applicant's algorithm. Circled spots were picked for identification.
Figure 14:
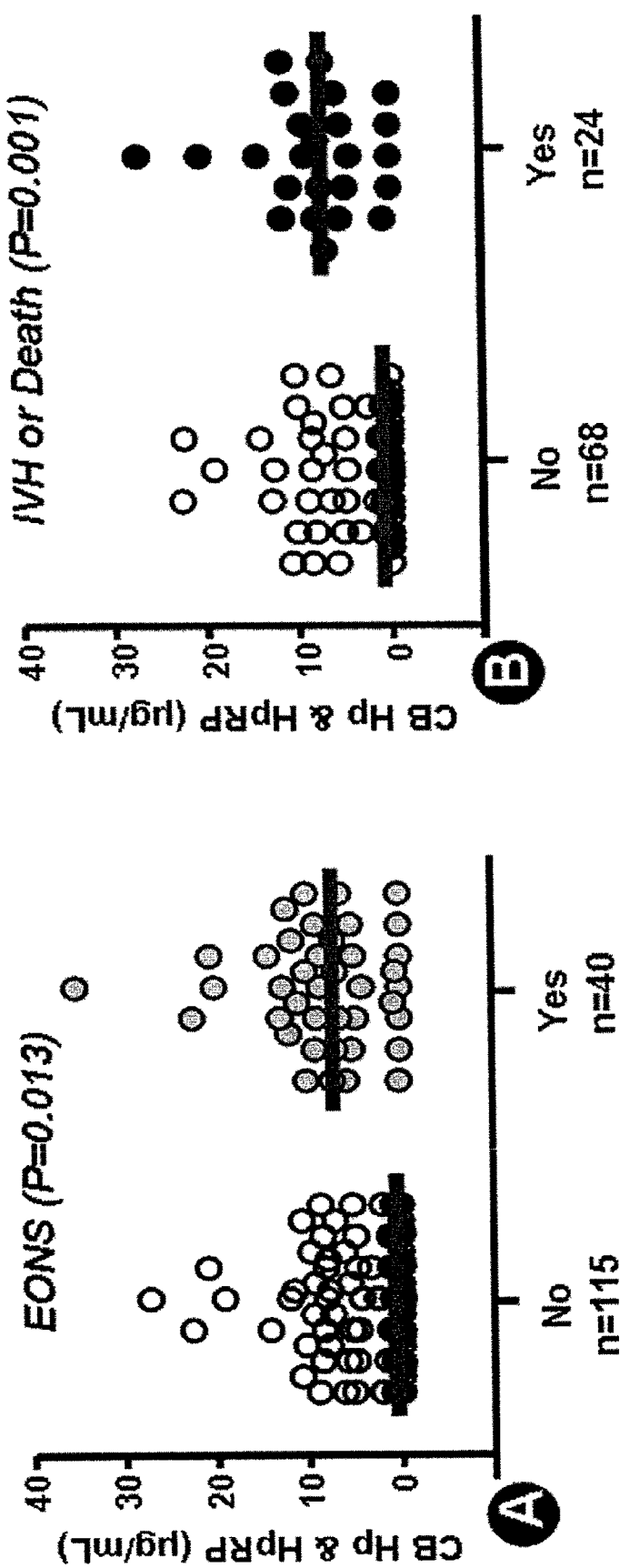
FIGS. 14A and 14B show, respectively: Hp and HpRP immunoreactivity in cord blood (CB) of 155 preterm newborns born at YNHH. Of these, 40 had a diagnosis of EONS, either confirmed (by positive cultures, n=8) or suspected (by clinical and hematological criteria, n=36).

In a prospective study design, Applicant enrolled 155 premature newborns whose mothers presented with symptoms of preterm labor or PPROM and had a clinically indicated amniocentesis to rule out infection. Intra-amniotic inflammation was assessed by SELDI-TOF mass spectrometry. Neonatal hematological indices and sepsis categorization were assessed from blood specimens and cultures obtained immediately following delivery for all neonates. Proteomic studies were conducted in 2 phases. In the discovery phase, the study group consisted of 3 neonates with confirmed positive $E.$ $coli$ sepsis, high CB IL-6 (>90 pg/mL), positive AF cultures and grade 4 histological chorioamnionitis. Three newborns matched for GA, low CB IL-6 (<9 pg/mL) delivered in the setting of idiopathic PTB served as control (reference). Applicant performed 2D-DIGE after albumin and IgG depletion. Two of the three 2D-DIGE gels analyzed for the purpose of biomarker identification are presented in FIG. 13. A total of 69 spots that were differentially expressed >3-fold. These were automatically picked and subjected to robotic tryptic digest and tandem mass spectrometry. 230 identities were matched in International Protein Index (IPI) database. 68 non-redundant IPI identities were extracted, of which 20 were common to 2/3 gels. Because several different spots matched to the same protein precursor, only 9 proteins were retained as potential biomarkers. ApoH, ApoE, vitamin D binding protein and albumin appeared in average downregulated. ApoA4, α-fetoprotein, α2-macroglobulin, Hp and HpRp appeared up-regulated. The highest fold increase differences were seen for Hp (32-fold) and for HpRP (60-fold). In the validation phase immunoassays were performed to confirm or refute the differential expression of these potential biomarkers in the entire cohort. Following correction for GA, Applicant determined that significant differences between neonates without and with EONS (confirmed by culture [n=8] or suspected [n=36]) maintained only for Hp and HpRP (FIG. 14A). Applicant next asked the question whether Hp and HpRP have relevance for neonatal outcomes other than EONS, which as shown earlier, has inherent clinical diagnostic challenges. In multivariate logistic regression analysis Applicant determined that after correction for GA and EONS status, neonates who developed IVH or died had higher Hp levels at birth (F ratio=11.4, P<0.001) (FIG. 14B). Other variables excluded from the model were level of intra-amniotic inflammation (MR score), severity of histological chorioamnionitis, CB IL-6, cord pH, antenatal steroid and antibiotic use.

Example 2

Identification of Protein Biomarkers Identified in the Cord Blood Take and Delivery that are Diagnostic of and Predictive for EONS Proteomic analysis of cord blood samples (using the methodology described in Buhimschi et al. PLoS ONE 3 (4): e2049) identified 20 proteins and protein fragments (listed in Table 1) in cord blood samples from babies who subsequently developed EONS, whose levels were either increased or decreased by 3-fold or greater, compared to controls. The mothers had a clinically indicated amniocentesis to rule out infection. For research purposes, intra-amniotic inflammation was assessed by SELDI-TOF mass spectrometry. In this study, histological chorio-amnionitis was scored using well recognized criteria. Umbilical cord blood was used to assess fetal acid-base and inflammatory status at birth. 16s-RNA gene amplification was applied in a select group of cord blood samples to provide proof of concept that bacteria may be present in neonates who have EONS, but negative microbial cultures. Neonatal hematological indices and sepsis categorization were assessed from blood specimens and cultures obtained immediately following delivery for all neonates. Analysis of the levels of one or more (a, at least one) of these proteins or protein fragments is useful in diagnosing EONS.

TABLE 1

Proteins and Protein Fragments Identified in Cord Blood of Babies Who Developed EONS

| IPI ID# | Abbreviation/Name |
| --- | --- |
| IPI00021842 | APOE apoliprotein E precursor |
| IPI00022434 | ALB uncharacterized protein ALB |
| IPI00022443 | AFP alpha-fetoprotein precursor |
| IPI00216773 | ALB ALB protein |
| IPI00298828 | APOH Beta-2-glycoprotein 1 precursor |
| IPI00304273 | APOA4 Apolipoprotein A-IV precursor |
| IPI00384697 | ALB isoform 2 of serum albumin procursor |
| IPI00431645 | HP HP protein |
| IPI00477597 | HPR isoform 1 of Haptoglobin-related protein precursor |
| IPI00478003 | A2M Alpha-2-macroglobulin precursor |
| IPI00478493 | HP Haptoglobin isoform 2 preprotein |
| IPI00555812 | GC Vitamin D-binding protein precursor |
| IPI00607707 | HPR Isoform 2 of Haptoglobin-related protein precursor |
| IPI00641737 | HP Haptoglobin precursor |
| IPI00742696 | GC Vitamin D-binding protein precursor |
| IPI00745872 | ALB Isoform 1 of serum albumin precursor |
| IPI00847179 | APOA4 apolipoprotein A-IV precursor |
| IPI00878517 | ALB 56 kDa protein |
| IPI00878953 | APOE MRNA for apolipoprotein E |
| IPI00879456 | APOE 25 kDa protein |

Example 3

Assessment of Hp Phenotype Variations and Levels as Determinants of Susceptibility to Adverse Neonatal Outcomes OBJECTIVE: Hp is an immunomodulatory protein linked to human susceptibility versus resistance to infection. Two allelic variants (Hp1 and Hp2) code proteins with different α-chains. Developmental regulation of Hp transcription shows that Hp is near to absent at birth, with the adult phenotype (Hp1-1; Hp2-1 or Hp2-2) emerging in the first year of life. Characterization of the cord blood proteome enabled the discovery of Hp as a biomarker of EONS. Hp phenotype variations and levels are critical determinants of susceptibility to adverse neonatal outcomes.

STUDY DESIGN: Applicant analyzed cord blood from 163 preterm neonates (GA: 29 [23-34] wks). Fetal inflammatory status was assessed by IL-6 levels. Symptoms, hematological criteria and bacterial cultures were used to define EONS. Expression patterns and Hp phenotyping was performed using Western blot. Serum from adult individuals and normal term newborns (n=19) served as reference (control). Differential expression of Hp was validated using ELISA. Relationships among Hp switching-on, levels, phenotypes and outcomes including EONS, IVH and death were explored using multivariate regression and nonparametric statistics.

RESULTS showed the following:

1) EONS (n=46) was characterized more often by antenatal Hp switching-on (P<0.001) and significantly higher Hp levels (P<0.001), independent of GA and IL-6;

2) Phenotypes impacted Hp level: Hp2-1>Hp2-2>Hp1-1 (P<0.001);

3) Newborns with EONS and Hp2-1 had the highest Hp levels, double that of Hp1-1 (P=0.003);

4) Neonates who developed IVH or died (n=36) had higher Hp levels (P<0.001) independent of GA, IL-6; cord pH, steroid and antibiotic use;

5) Newborns with switched-on Hp at birth had an increased risk of IVH and death (RR: 3.6 [1.8-7.8]); 6) No term neonate (but all adults) had switched-on Hp.

CONCLUSION: Applicant provides the first evidence that Hp switches on precociously to the adult phenotype in newborns with EONS. The quantitative and qualitative changes in Hp expression provide the basis for predicting newborns at risk for IVH and/or death and targeted interventions at birth.

Example 4

Cord Blood Hp and HpRP Signature as Eons Biomarker

Figure 16:
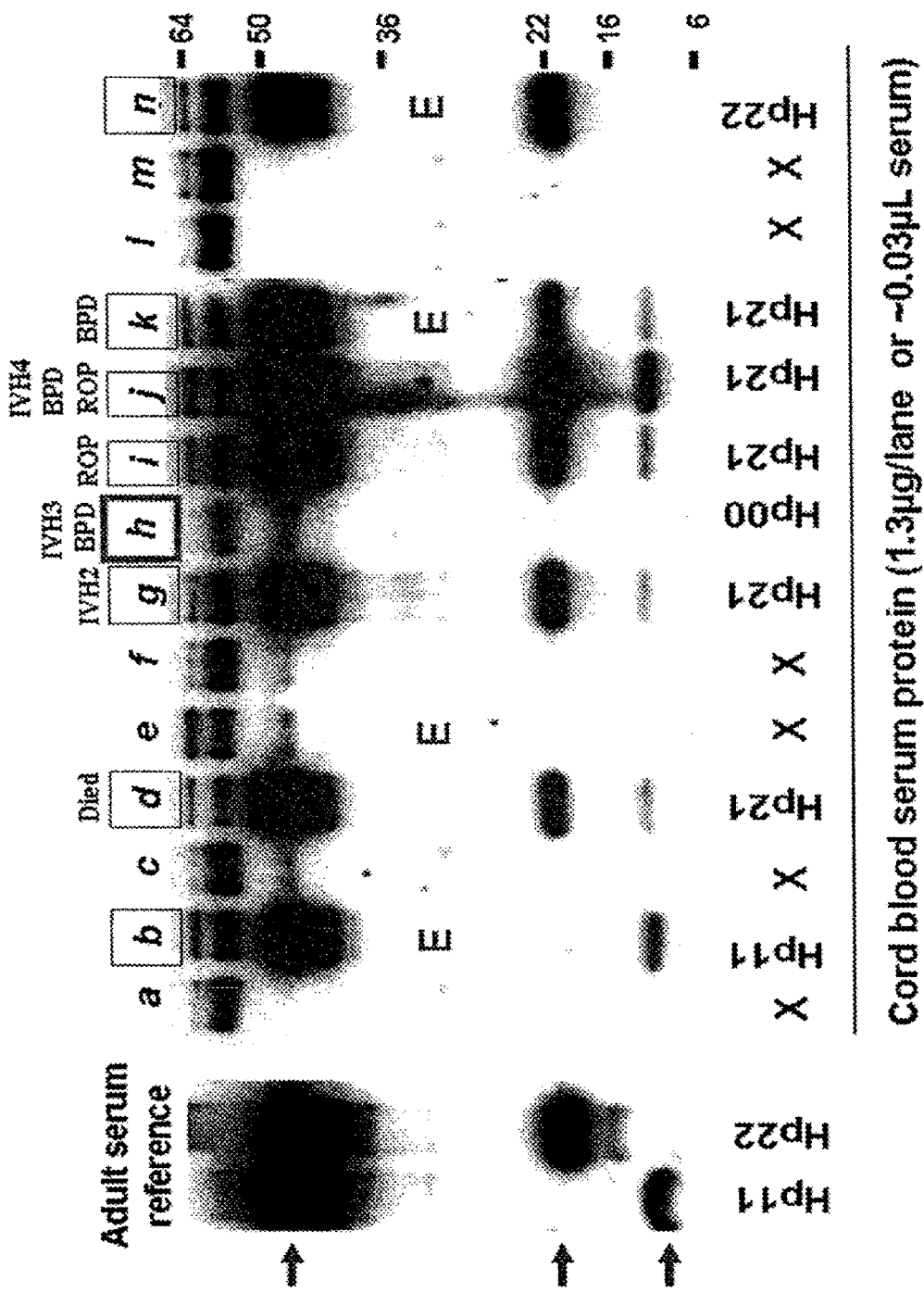
FIG. 16 shows Hp and HpRP signatures revealed by Western blot using an antibody that reacts with both Hp chains and with HpRP. The lanes to the left contain serum of Hp1-1 or Hp 2-2 adults (Sigma). Lanes a-n were loaded with cord serum from preterm newborns who were admitted to Yale NBSCU and had a sepsis workup. EONS was diagnosed in 4 newborns who received i.v. antibiotics (marked with E) but only in one cultures were positive (baby "e"; *S. aureus*). Red squares note babies with elevated cord IL-6. Adverse short-term outcomes are specified above each lane as death, intra-ventricular hemorrhage (IVH grade 2 or more), bronchopulmonary dysplasia (BPD, need for oxygen at 36 weeks postmenstrual age) and retinopathy of prematurity (ROP grade 2 or more). All newborns have known short-term outcomes and some are enrolled in the long-term follow-up program where they are followed with neuro-developmental assessments part of the NICHD Research Network. Babies "h" and "j" have severe forms of cerebral palsy.

To validate cord blood Hp and HpRP ELISA results and provide further understanding of how Hp phenotypes impact on total immunoreactivity, Applicant performed Western blot analysis under reducing and denaturing conditions (normalized for amount of total protein to rule out hemoconcentration as a potential bias). Control sera from adult Hp1-1 and Hp2-2 individuals served as reference. As illustrated in FIG. 16 for representative CB samples, Applicant made several interesting observations: 1) Each lane yields a pattern of 3 possible Hp and HpRP bands (or lack thereof) shown by the red arrows; 2) CB Hp and HpRP signature is composed of at least 5 pieces of information for each baby: antenatal switching, defined with reference to this figure as appearance of at least 2 of 3 Hp and HpRP bands (newborns b, d, g, i-k & n); Hp and HpRP level; Hp phenotype; relationship of Hp and HpRP with IL-6 levels; relationship of Hp and HpRP with bacterial footprints; 3) The amount of sample required to yield this information is minimal (<1 µL cord serum).

At this time Applicant analyzed Hp and HpRP signatures for only a small portion of the available samples. Following are several aspects derived from an analysis of CB retrieved from 14 random newborns in the cohort (FIG. 16). The results point out that 7 fetuses had positive antenatal Hp switching, yet only 3 of these had a diagnosis of EONS (marked as E). This suggests that the current clinical and hematological criteria for EONS still miss newborns who progress to have major adverse outcomes. In contrast, the CB of baby "e", a 28-week newborn of 1,200 grams who did not appear to have a positive antenatal switch, tested positive for S. aureus. This neonate received i.v. antibiotics and had a favorable course in NBSCU (the baby was discharged after 24 days with no evidence of short or long-term complications). Based on Applicant's assessment, it is likely that the cultures were contaminated ex vivo. Also notable is baby "h," who out of all 14 newborns had the highest level of CB IL-6 (>1,200 pg/mL), yet did not appear to have switched its Hp and HpRP expression antenatally. This Hp signature is consistent with a genetically determined Hp0-0 phenotype, which results in a fetus unable to up-regulate an important endogenous antioxidant resource such as Hp, despite excess transcriptional trigger (IL-6). It is thus not surprising to determine that this newborn had the worst outcome despite a birthweight of 1,380 grams (GA at delivery $31^{2/7}$ weeks). The mother was admitted with PPROM at 27 weeks and was managed expectantly with antibiotics in accordance to ACOG guidelines. Development of non-specific signs of chorioamnionitis on day 17 of PPROM prompted an amniocentesis to rule out infection. The AF tested positive for S. viridans. By mass spectrometry SELDI-TOF Applicant found an MR score 4 consistent with "severe inflammation." Histological analysis of the placenta demonstrated stage III chorioamnionitis and grade 4 funisitis. Based on this case, Applicant questioned whether other newborns in the cohort had a similar signature (elevated cord IL-6 and absent Hp and HpRP switching). Preliminary data analysis identified two cases who matched baby "h." One neonate (600 grams at birth) died on postnatal day 2. A second neonate weighed 1,280 grams at birth (GA at delivery $30^{2/7}$ weeks). The baby was admitted to NBSCU where EONS was established based on a positive blood culture for E. coli. The baby developed grade 4 IVH and undergoes follow-up at Yale Child Study Center for cerebral palsy. The AF MR score showed evidence of "severe inflammation" (MR score 3) and display proteomic biomarkers characteristic for bleeding. AF in this case tested negative for infection by conventional tests. Applicant's measure of CB IL-6 was 1,533 pg/mL. The level of total Hp and HpRP by ELISA was undetectable; lack of Hp switching was observed by Western blot.

Example 5

Assessment of Elements for Early Diagnosis and Pathogenic Classification of EONS Described herein is an algorithm for early diagnosis and pathogenic classification of EONS, based on one (a, at least one, one or more) of the following elements:

(a) Cord blood Hp and HpRP switching, represented qualitatively as positive or negative and derived from Hp and HpRP immunoreactivity above an established cut-off;

(b) Cord blood Hp and HpRP level represented quantitatively as the level of Hp and HpRP immunoreactivity;

(c) Cord blood Hp and HpRP phenotype, which is Hp 0-0, Hp 1-1, 1-2 or 2-2;

(d) Relationship of cord blood Hp and HpRP level with cord blood IL-6; and (e) Relationship of cord blood Hp and HpRP level and cord blood IL-6 with bacterial fingerprints.

One or more (a, at least one) of these elements can be used for early diagnosis and pathogenic classification of EONS (one or more, two, two or more, three, three or more, four, four or more or five elements can be used). In a specific embodiment, the method comprises assessing at least elements (a)-(d). In addition, element (e) can be included in the method, if it is of interest to distinguish among the 3 variants of EONS (I, II or III), in order to identify specific drug targets, such PAMPs or DAMPs. If the testing enables sub classification of EONS, antibiotics could be substituted by anti DAMP and/or anti PAMP strategies, such as: N-acetylcysteine, ethylpyruvate or quercetin (flavonoid with potent anti-oxidant properties and DAMP inhibitor)[77] or soluble RAGE (sRAGE, an extracellular truncated form of RAGE which acts as a decoy DAMP receptor) or antibodies or peptides targeted against RAGE or HMGB1 attenuate the lethal effects of endotoxin, acetaminophen and ischemia-reperfusion.[78,79,80,81,82,83,84]

There are several reasons why it is particularly useful to determine these elements concurrently for an accurate diagnosis of EONS (and why probably other authors concluded that haptoglobin is not a good biomarker of sepsis in newborns.[85,86]) First, the Hp and HpRP level measured in immunoassay is dependent not on only on the amount of Hp in solution, but also on the phenotype that is measured. Applicant observed that in ELISA, Hp2-2 measures consistently higher than Hp 1-1. Although the exact reasons are still to be elucidated, it is possible that the multimeric aggregates formed by Hp2-2 have a higher antibody affinity than Hp1-1. Therefore, the ELISA level is a non-linear combination of the amount and phenotype and not of the concentration alone. To substantiate this premise, Applicant tested how phenotypes impacted on Hp level and found among newborns with positive switching a significant difference in the measured level of Hp and HpRP immunoreactivity with Hp2-1>Hp2-2>Hp1-1 ($P<0.001$). Newborns with EONS and Hp2-1 had the highest Hp levels, double that of Hp1-1 ($P=0.003$). Although this could also suggest that upon the same inflammatory insult, the heterozygote phenotype produces more Hp than does the homozygous phenotype, it could also mean that the fetal Hp phenotype has relevance for complications occurring in postnatal life that could make the heterozygote more susceptible to diseases with a free radical component. Indeed, neonates who developed IVH or died (n=36) had higher Hp levels ($P<0.001$) independent of gestational age, cord blood IL-6, cord pH, steroid and antibiotic use. Overall, newborns with switched Hp at birth had an increased risk of IVH & death (Relative Risk: 3.6 [1.8-7.8]). Because a minority of fetuses may have genetically determined Hp 0-0, they will not be able to respond with Hp switching when faced with an inflammatory insult. These fetuses will have highly elevated IL-6 levels in cord blood, in the absence of Hp and HPRP switching and it is likely that they will have the worst outcomes. Because of the importance of producing a tool to rule out EONS at birth, it is important to distinguish this small subgroup from the newborns who did not have a bacterial encounter in utero. The phenotype corrected cord blood ratio of Hp and HpRP-to-IL6 can be used to achieve this goal.

Described herein and represented in Table 2 is a simple diagnostic and treatment algorithm that can be implemented immediately in intensive neonatal care units and could serve to decrease considerably the adverse effects the costs of empiric antibiotic therapy.

This algorithm is underscored by the observation that no healthy term neonate tested to date (n=19), but all matched mothers, had switched Hp. Moreover, this algorithm could also be extended to ruling out EONS in term newborns. To this end, Applicant tested cord blood in one case of clinical chorioamnionitis at term and found that this newborn, who was diagnosed with suspected EONS and received antibiotics, also had positive Hp and HpRP switching at birth. An advantage of this algorithm is that it can be assessed with various methodologies within 1 hour of birth. The high level of Hp and HpRP (microgram/mL) can be easily detected in various rapid methods and can even be multiplexed with IL-6, since the only subcategory that benefits from addition of IL-6 would have a high CB IL-6 immunoreactivity.

Example 6

A Proteomics Analysis of Umbilical Cord Blood to Identify Biomarkers and Functional Role in Networks Characteristic of EONS Summary Design The initial proteomics discovery phase used two-dimensional differential gel electrophoresis (2D-DIGE). Spots differentially expressed between gestational age (GA)-matched preterm newborns without or with culture-confirmed EONS (n=3/group) were identified by mass spectrometry. A 1st-level validation was conducted by ELISA in a distinct cohort of 174 preterm newborns. Validated biomarkers were subjected to latent class analysis (LCA) for unbiased clustering of all 180 newborns based on probability of "antenatal exposure to infection/inflammation". The final algorithm was subjected to a 2nd-level validation against indicators of adverse short-term neonatal outcome.

Participants This study used 180 consecutive women with preterm birth and clinically indicated amniocentesis to rule-out infection. All newborns were admitted to Newborn Special Care Unit and followed until death or discharge.

Maine outcome measures Concentration (ELISA) and phenotypical characteristics (western blot) of putative biomarkers, clinical diagnosis of EONS (hematological indices, clinical manifestations and/or blood cultures) and short-term neonatal adverse were measured outcomes in this study.

Results Differentially expressed protein identities (n=19) converged into ontological classes, which included transfer/carrier, protease/extracellular matrix and defense/immunity. An upregulation in haptoglobin (Hp) and haptoglobin-related protein (HpRP) immunoreactivity passed the $1^{st}$-level validation independent of GA at birth ($P<0.001$). A higher number of premature newborns with clinical EONS expressed Hp and HpRP in cord blood (i.e. "switch-on pattern") as opposed to the majority of non-EONS preterm or term newborns (n=19) who displayed a normal switch-off pattern. An LCA model combining the Hp and HpRP switch-on pattern, an elevated cord blood interleukin-6, and hematological indices sugges-

TABLE 2

| CB IL6 | CB Hp & HpRP switching | CB Hp type | Conclusion | Prognosis and recommendation relative to antibiotic profilaxis In NICU |
|---|---|---|---|---|
| neg | neg | Hp 0-0 | non-exposed and non-switched | Good. Should not receive antibiotics |
| pos | neg | Hp 0-0 | exposed and non-switched | Poor. Should be admitted to NICU and treated |
| pos | pos | Hp 1-1, 1-2 or Hp 2-2 | exposed and switched | Variable depending on Hp type. Should be admitted to NICU and treated |
| neg | pos | Hp 1-1, 1-2 or Hp 2-2 | past-exposed and switched | Poor. This is a rare instance that occurs mostly in neutropenic fetuses. Should be admitted and treated | tive of EONS delineated a cluster with high probability of antenatal exposure to infection/inflammation. This algorithm resulted in reclassification of ~30% of cases with respect to EONS diagnosis improving number needed to harm (NNH) and the odds ratios for several adverse outcomes. In exposed newborns, disparity in Hp phenotype impacted on cord blood Hp and HpRP levels and on outcome with Hp 2-2-expressing newborns having lower morbidity.

Conclusions Antenatal exposure to infection/inflammation results in precocious switch-on in Hp and HpRP expression. Cord blood Hp and HpRP has biomarker potential to improve the diagnostic scheme of EONS.

Methods

Study population. The Applicant studied samples of umbilical cord blood serum retrieved from 180 consecutive preterm singleton neonates born to mothers who had an amniocentesis to rule out intra-amniotic infection (May 2004-September 2009). All fetuses were born live and were admitted to the Newborn Special Care Unit (NBSCU) of Yale New Haven Hospital (YNHH). A flowchart of the neonates enrolled in this study and subgroups of samples analyzed during the discovery and validation phases presented in FIG. 17.

All women presented with symptoms of preterm labor, preterm premature rupture of membranes (PPROM), advanced cervical dilatation (≥3 cm), or uterine contractions intractable to tocolysis. Gestational age of the fetus was determined based on maternal last menstrual period and ultrasound evaluation performed prior to 20 weeks GA.[12] Preterm labor and PPROM were established based on well-established clinical criteria.[13] All mothers provided written informed consent. The Yale University Human Investigation Committee approved the study protocol.

All amniocentesis procedures were clinically indicated and were performed under sterile conditions. Inclusion criteria for the study population included: singleton fetus born alive, admission to NBSCU, appropriate growth for GA, normal anatomic ultrasonographic survey. Newborns delivered by women with medical conditions (e.g., hypertension, diabetes, thyroid disease), human immunodeficiency, hepatitis or other viral infections were not enrolled. Other exclusion criteria included presence of fetal heart rate abnormalities at enrollment (e.g., bradycardia, or prolonged variable decelerations) or fetal structural abnormalities. Following amniocentesis each patient was followed prospectively to delivery, independent of our research protocol. In the absence of signs/symptoms of clinical chorioamnionitis (fever >37.8° C., uterine tenderness, fetal tachycardia), AF laboratory results suggestive of infection, non-reassuring fetal heart and/or abruption, PPROM was managed expectantly. Prior to delivery, corticosteroids for lung maturity and antibiotics were administered when Clinically indicated.[13] Induction of labor or a surgical delivery was performed for indications such as AF laboratory results traditionally considered to indicate IAI/infection,[2] prolapsed umbilical cord and/or GA≥34 weeks.[14] The neonatology resuscitation team was present at the time of delivery for all neonates.

To investigate the effect of GA on expression levels of potential biomarkers, the Applicant retrieved paired maternal and cord blood samples from 19 healthy non-laboring women at term (GA: 38-40 weeks). Term women underwent a scheduled elective Cesarean delivery for indications such as fetal malpresentation (e.g., breech) or prior Cesarean delivery. All their infants were appropriately grown for GA and had reassuring fetal heart patterns prior to surgery.

Biochemical and microbiological studies of AF For clinical management, a diagnosis of IAI/infection was established based on well-recognized clinical, biochemical and microbiological test results for AF. Clinical laboratory tests were: glucose (cut-off of ≤15 mg/dL), lactate dehydrogenase (LDH, cut-off ≥419 U/L), white blood cell count (WBC, cut-off ≥50 cells/mm$^3$), Gram stain and microbiological cultures for aerobes, anaerobes, *Ureaplasma* and *Mycoplasma* species.[2,15,16]

Histological chorioamnionitis In all 180 cases, hematoxylin and eosin-stained sections of extraplacental membranes (amnion and chorio-decidua), chorionic plate, chorio-decidua and umbilical cord were examined systematically for inflammation. Three histological stages of chorioamnionitis[17] (stage I: intervillositis, stage II: chorionic inflammation, and stage III: full thickness inflammation of both chorion and amnion) were complemented by a previously described histological grading system that includes 4 grades of inflammation of the amnion, chorio-decidua and umbilical cord.[18]

Umbilical cord blood. Umbilical cord blood was obtained by sterile puncture of the clamped umbilical vein at the time of delivery. Immediately following collection, the cord blood was centrifuged at 1,000 g at 4° C. for 15 min. Serum was aliquoted in sterile tubes and stored at −80° C. until 2D-DIGE and MALDI-MS/MS was applied in select cases and the levels of IL-6 and other potential biomarkers evaluated by ELISA.

Diagnoses of EONS and of other short-term neonatal outcomes (IVH, ROP, NEC, BPD and death) Neonatal hematological indices were assessed from blood specimens and cultures obtained within 2 hours from birth. A diagnosis of "suspected EONS" was based on presence of at least two of the following hematological criteria: 1) absolute neutrophil count of <7,500 or >14,500 cells/mm3; 2) absolute band count >1,500 cells/mm3; 3) immature/total neutrophil (I:T) ratio>0.16; 4) platelet count <150,000 cells/mm.[3,19] "Clinical EONS" was defined as the presence of suspected EONS corroborated with clinical symptoms or culture-positive EONS at ≤72 hours after birth. Per institutional protocol, all neonates with clinical EONS received antibiotherapy.

Evaluation for IVH was done per institutional protocol using serial cranial ultrasounds on days 3, 7-10 and 30 of life. Additional scans were performed if clinically indicated. The diagnosis and grading of IVH was established by experienced pediatric radiologists: grade 1, germinal matrix hemorrhage; grade 2, intraventricular blood without distension of the ventricular system; grade 3, blood filling and distending the ventricular system and grade 4, parenchymal involvement of hemorrhage, also known as periventricular venous infarction.[20] The ophthalmologist classified ROP in each eye according to the international classification.[21] Clinical, metabolic, hematologic and abdominal x-ray abnormalities (e.g., pneumatosis intestinalis, portal venous gas) criteria were used to diagnose NEC.22 BPD was defined as receiving supplemental oxygen at 36 weeks postmenstrual age.[23]

Figure 17:
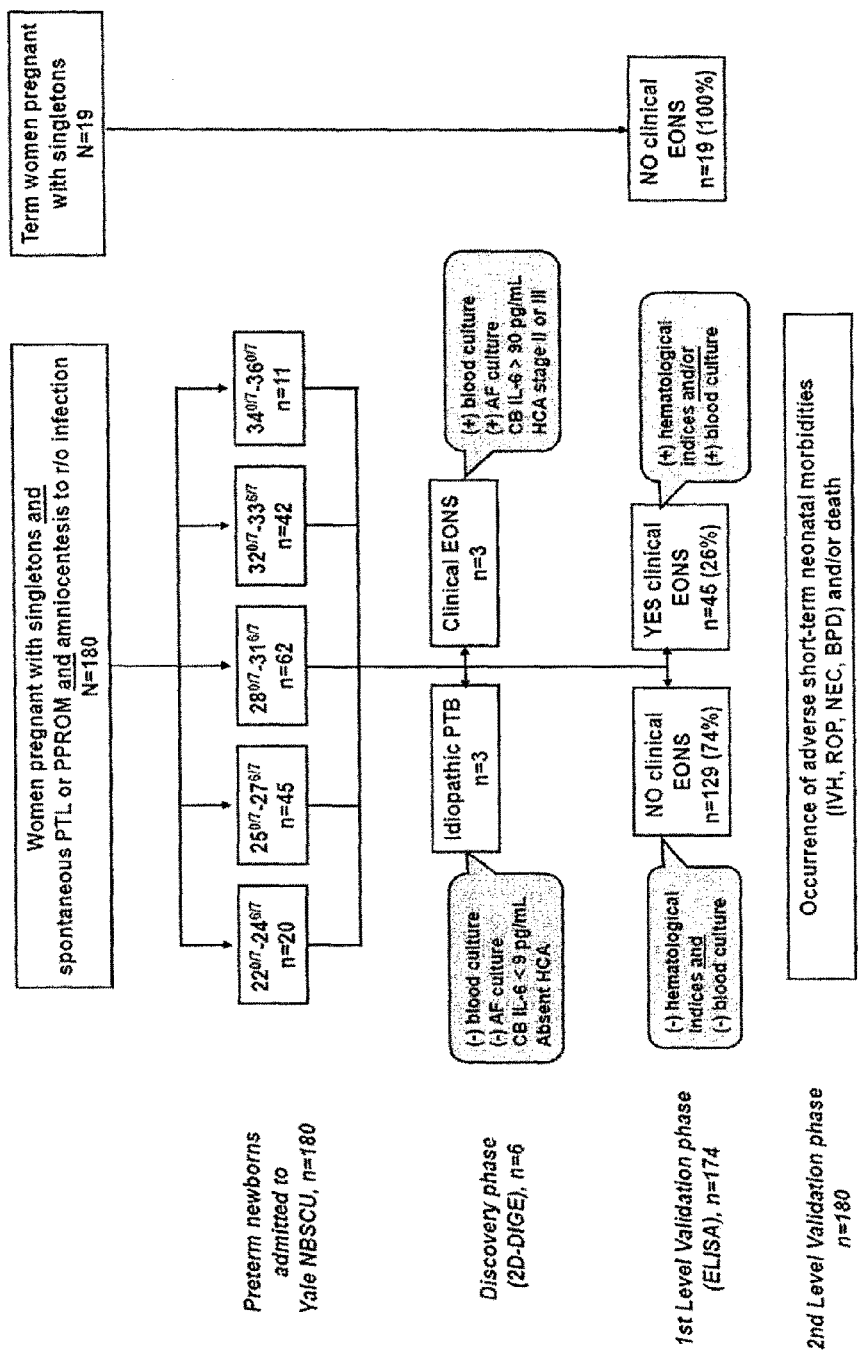
FIG. 17 is a schematic of the study design.

Study design—Discovery phase To identify biomarkers and functional protein networks characteristic of EONS, Applicant first employed 2D-DIGE on select pairs of cord blood serum samples from 3 preterm newborns (GA: median, interquartile range [IQR]: 28 [25-30] weeks) with clinical EONS (FIG. 17). All neonates in the EONS group of the discovery phase had positive blood cultures for *Escherichia coli* and an elevated fetal inflammatory response to infection (cord blood IL-6>90 pg/mL).[24] Histopathological evaluation of their placenta showed histological chorioamnionitis. Three neonates without EONS delivered in the setting of idiopathic PTB (GA: 26 [25-30], absent IAI, negative AF cultures, absent histological chorioamnionitis) were used as control. There was no statistical GA difference between EONS and idiopathic PTB cases (paired t-test P=0.169). 2D-DIGE was performed using the Ettan DIGE system (GE Healthcare, Piscataway, N.J.). Identification of low abundant proteins was facilitated with the aid of albumin and IgG removal kit (GE Healthcare), as previously described.[25] Cord blood proteins (50 μg) were labeled with either Cy5 (EONS group) or Cy3 (idiopathic PTB group). A reference pool (25 μg total protein) was labeled with Cy2 and used as internal control. For each pair, labeled samples were pooled and isoelectric focusing performed using an isoelectric point range of 3-10. SDS-PAGE on a 12% gel was performed for the second dimension. After spot detection, automatic background correction, spot volume normalization and volume ratio calculation, dye ratios were determined using DeCyder Extended Data Analysis software (GE Healthcare). Spots corresponding to ≥1.5-fold changes were robotically excised using the Ettan Spot Picker instrument (GE Healthcare) and subjected to automated in-gel tryptic digestion on the Ettan TA Digester (GE Healthcare). Automated MALDI-MS/MS spectra were acquired on the 4800 TOF/TOF proteomics analyzer (Applied Biosystems, Foster City, Calif.). The resulting peptide sequences along with spot information (Cy5/Cy3 ratio, location on gels) were uploaded in the web-accessible Yale Protein Expression Database (YPED—medicine.yale.edu/keck/proteomics/yped/index.aspx).[26] The data was analyzed using the Applied Biosystems GPS Explorer software with Mascot analysis against the nr database of National Center for Biotechnology Information (NCBInr) as well as the International Protein Index (IPI) database.[27] A combined peptide mass fingerprint and MS/MS search was done. A comprehensive list of probable identities (Mascot scores of ≥81 for NCBInr and ≥61 for IPI) generated.

Study design—Pathway analysis Unique protein IPI identities differentially expressed ≥1.5 fold were classified based on the PANTHER (Protein ANalysis THrough Evolutionary Relationships) system (pantherdb.org). PANTHER is unique resource that classifies genes and proteins by their functions, using published scientific experimental evidence and evolutionary relationships abstracted by curators with the goal of predicting function even in the absence of direct experimental evidence. Proteins are classified into families and subfamilies of shared function, which are then categorized using a highly controlled vocabulary (ontology terms) by biological process, molecular function and molecular pathway.

Study design—1st Level Validation Phase A reductionist algorithm was next applied to extract unique identities differentially expressed in at least 2 of the 3 DIGE gels. Such strategy gives priority to biological consistency rather than to in-silico database matching scores. This approach pointed toward haptoglobin (Hp) and haptoglobin-related protein (HpRP), α-fetoprotein (AFP), vitamin D binding protein (VDBP), apolipoprotein A4 (APOA4), apolipoprotein E (APOE) and apolipoprotein H (APOH), potential cord blood biomarkers for EONS.

The HpRP gene product has >90% sequence with Hp.[28] Although reportedly expressed in adult serum, HpRP represents at the best estimate ~7% of total Hp and HpRP immunoreactivity.[29] Identification of a distinct mRNA coding for HpRP and an antibody that specifically differentiates HpRP from Hp continues to be elusive.[30] Thus, for the purpose of this study, the Applicant refers to the combined Hp and HpRP immunoreactivity (Hp&HpRP) as assessed by an anti-Hp antibody pair bioassay (H1820-04, US Biological, Swampscott, Mass.). Samples for Hp&HpRP ELISA were diluted with blocking buffer (5% non-fat dry milk) 100, 1,000 or 10,000-fold (cord blood) or only 10,000-fold (maternal blood). A mixed Hp standard (250-3.9 ng/ml) was used for standard curve. Immunoassays for AFP (R&D Systems, Minneapolis, Minn.), total VDBP (ICL Inc, Newberg, Oreg.), actin-free VDBP (Alpco, Salem, N.H.), ApoA4 (Cederlane Labs, Burlington, N.C.), ApoE (MBL International, Woburn, Mass. and ApoH (Enzyme Research Laboratories, South Bend, Ind.) were performed according to each procedure summary. In pilot experiments, the Applicant determined the cord blood serum optimal sample dilutions for AFP (50,000-fold), VDBP (total 50,000-fold, actin-free 5,000-fold). ApoA4 (100-fold), ApoE (500-fold) and ApoH (10,000-fold). IL-6 (Pierce-Endogen, Rockford, Ill.) was measured in AF and cord blood to assess the inflammatory status of the two biological compartments. All samples were tested in duplicate by investigators unaware of case origin or outcome. Cord serum total protein was quantified using bicinchoninic acid (BCA) assay (Pierce Biotechnology, Rockford, Ill.).

Study design—Western blotting of Hp&HpRP immunoreactivity for determination of Hp switch-on pattern and Hp phenotypes. SDS-PAGE gels (10-20%, InVitrogen, Carlsbad, Calif.) were loaded with equal amounts of cord blood protein (2 μg/lane) mixed 1:2 with reducing sample buffer (Bio-Rad, La Jolla, Calif.) and boiled for 5 min. After electrophoretic transfer, nitrocellulose membranes (Bio-Rad) were blocked with 5% milk and then incubated overnight at 4° C. rabbit anti-Hp polyclonal antibody (1:3,000, Sigma, St Louis, Mo.). Detection was performed using biotinylated goat anti-rabbit secondary antibody (1:5,000, Jackson Immunoresearch, West Grove, Pa.) followed by streptavidin-linked horseradish peroxidase, (1:8,000, Amersham Biosystems, Piscataway, N.J.), chemiluminescence (ECL-Plus, Amersham) and a timed 3 min. exposure to film (Kodak Biomax).

Hp is an acute phase glycoprotein with a great variety of important biological functions, of which the most recognized is hemoglobin binding.[31] Hp is a tetrameric protein with two α and two β-chains linked by disulfide bonds. In humans, Hp occurs in two co-dominant allelic forms, Hp1 and Hp2 which differ in the length of the α-chain.[32] The human population has 3 major Hp phenotypes (Hp1-1, Hp2-2 and the heterozygous type Hp1-2) derived from variations in the α-chain with identical β-chains.[33] Absence of Hp at protein level denotes Hp0-0 phenotype (ahaptoglobinemia) which may result from a genetic lack of both Hp alleles, consumption in the process of hemoglobin scavenging or a switch-off in expression (gene silencing).

For the purpose of this study a detectable Hp β-chain (~42 kDa) on Western blot was indicative of a switch-on in Hp expression as opposed to the switched-off pattern if the β-chain was undetectable. Hp phenotypes were defined by additional presence of α-chain bands at ~9 kDa (α1: Hp1-1), ~20 kDa (α2: Hp2-2), or both (Hp1-2). Hp purified from blood of adults with known Hp phenotypes (Hp1-1, 1-2 or 2-2) was purchased from Sigma and used as positive control. Optical density of the bands of interest was analyzed with Image J software (NIH—rsb.info.nih.gov). The results were expressed as the optical density of each band and as total optical density calculated from the sum of α- and β-chains.

Study design—2nd Level Validation The performance of a new diagnostic test is traditionally evaluated relative to a gold standard. In the setting of EONS, a perfect gold standard does not exist due to clinical circumstances related to delivery of the neonate (e.g., antenatal antibiotics treatment, uncultivable bacteria, specimen contamination ex vivo). In response to this challenge, the Applicant applied latent class analysis (LCA), a statistical solution which has gained increasing acceptance when a perfect gold standard does not exist. Briefly, LCA assumes that a hidden (latent) variable is responsible for heterogeneity among observed variables (indicators: measurable characteristics involved in cluster formation). By studying the patterns of covariation among indicators, the nature of the latent variable can be characterized.[34] Specifically, rather than testing an a priori classifier (e.g., biomarker level above or lower than a pre-determined cut-off), the fit of a series of different models is examined. Each model combines several indicators and covariates (e.g., demographical variables, potentially adding to the characterization of the cluster). A single cluster model is examined first, then clusters are added until no further improvement in classification is observed. For the purpose of this study the latent variable was set as "antenatal exposure to infection/inflammation."

The goodness of fit was evaluated using several indices including BIC (Bayesian Information Criterion), AIC (Akaike information criterion). Lower BICs indicate model improvement. Conditional bootstrap re-sampling procedures (500 random iterations) were employed to compare fit indices between models. The input of each indicator to the final model was measured by the nominal correlation coefficient Goodman-Kruskal tau b (GK-θ). Finally, a posterior probability classifying each case to each cluster of the final model was calculated. Odds ratios (OR) and number needed to harm (NNH) were calculated to determine the risk of adverse neonatal outcomes. NNH indicates how many subjects need to be exposed to a risk factor to cause harm in one subject that would not otherwise have been harmed. The lower the NNH the worse the risk factor.

Statistical analysis Normality testing was performed using the Shapiro-Wilk test. Data were compared with one-way ANOVA followed by Holm-Sidak method (parametric) or Kruskal-Wallis on ranks followed by Dunn's tests (non-parametric) as appropriate. Pearson correlations were used to measure co-linearity between the selected independent variables as well as other relevant relationships between dependent and independent variables. Comparisons between proportions were done with Chi-square tests. The phi-coefficient of correlation (Φ), an index of agreement for binary data was calculated.[35] Stepwise multivariable regression analysis was used to determine concurrent relationships between variables and to correct for possible influences of gestational age and birthweight.

Statistical analyses were performed with SigmaPlot 11.0 (Systat Software) MedCalc (Broekstraat, Belgium), PASW Statistics (SPSS Inc) and Latent Gold 4.5 (Statistical Innovations) softwares. A P value of <0.05 was considered significant throughout the analysis.

Results

Figure 18:
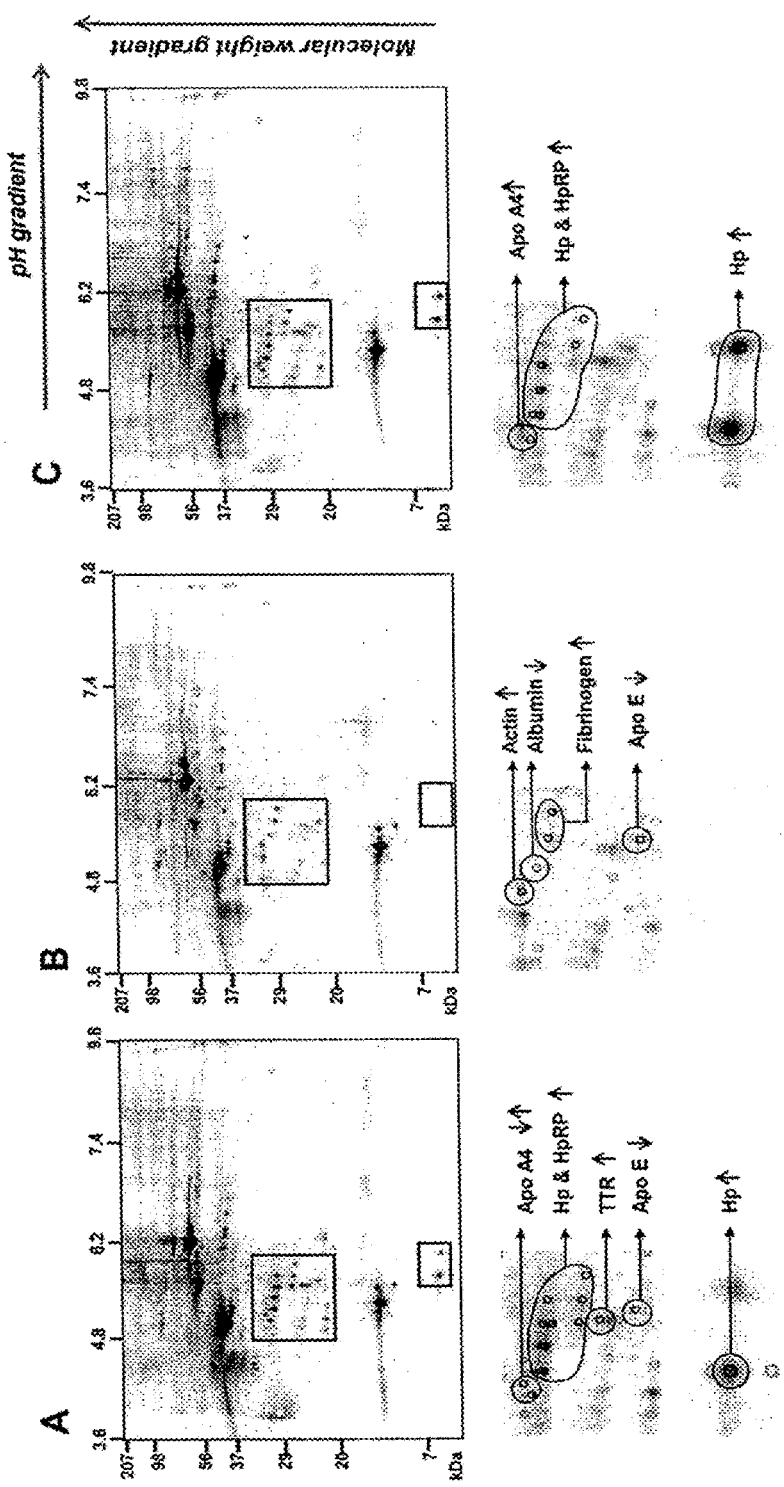
FIG. 18A-18C shows merged 2D-DIGE images of the three gels from the proteomics discovery phase and representative identified spots.

Differences in cord blood serum proteomes between newborns with proven culture EONS and idiopathic PTB. Mapping of the cord blood proteome identified 414 protein spots on 2DDIGE gels (n=3, FIG. 18). Cy5 (EONS)/Cy3 (idiopathic PTB) ratio was ≥1.5-fold different in 69 spots which were all subjected to identification by mass spectrometry. A total of 67 spots were matched to at least one gi identifier (down-regulated: 17 spots, up-regulated: 50 spots). With 1-5 identifiers/spot and multiple spots matching to the same identifier, the Applicant's most inclusive list had 135 unique NCBI nr identities. The analogous analysis against IPI human database found 70 unique IPI identities in at least ⅓ gels. The Applicant next excluded identifiers originating from a single 2D-DIGE gel with the rationale that these were most likely resulting from randomness (technical or biological). This novel approach resulted in the identification of 19 unambiguous IPI human identities that changed in the context of EONS ≥1.5-fold in at least ⅔ gels (Table 3).

Figure 19:
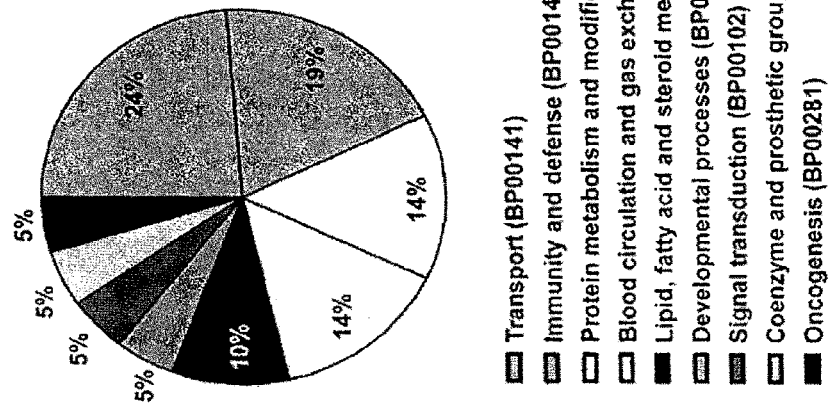
FIGS. 19A and 19B are schematics showing pathway analysis results and ontological classifications of identities differentially expressed at least 1.5-fold in cord blood of premature newborns with EONS.
Figure 19:
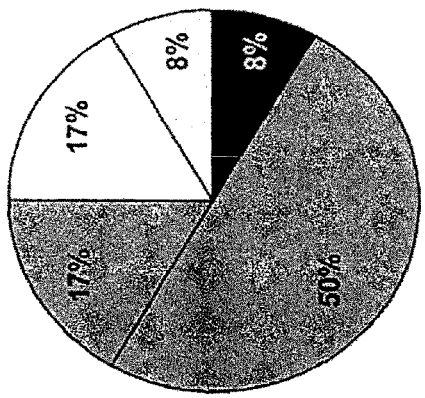

Data mining using PANTHER ontological classification system distributed the 19 IPI identities into 5 distinct molecular functions and 9 biological processes. The top populated functions and biological processes were transport and immunity/defense (FIG. 19). PANTHER converged the differentially expressed 19 IPI identities by matching several identities to the same protein precursor in the database (Table 3). This allowed us to conclude that pending validation, cord blood serum of EONS newborns is potentially characterized by net up-regulation in HpRP (60-fold), Hp (33-fold), alpha-fetoprotein (7-fold), VDBP (2-fold), and by net down-regulation of albumin (6-fold), apolipoproteins APOA4 (5-fold), APOE (3-fold) and APOH (3-fold). Spots matching to α2-macroglobulin changed in divergent directions resulting in null net change.

Validation of potential cord blood biomarkers for EONS Clinical characteristics of the mothers and newborns used for validation of potential biomarkers are included in Table 4. Mothers of neonates with EONS were of lower GA at recruitment, had shorter amniocentesis-to-delivery intervals, delivered at earlier GA newborns with lower birth weights and lower Apgar scores. Gestational age (GA) at delivery is an important determinant of neonatal maturity and outcome. Following correction for GA at birth, the Applicant determined that EONS impacted independently only on the 1-minute Apgar score. Results of clinical laboratory analyses are presented in Table 5. Women that delivered neonates with EONS had more often amniotic fluid biochemical and microbiological tests consistent with intra-amniotic inflammation and infection. There was a higher frequency of histological chorioamnionitis and funisitis in the EONS group. Neonatal hematological tests and indices affected by EONS independent of GA were WBC, neutrophil and lymphocyte counts, ABC and I:T ratio. In 7 newborns EONS was confirmed by a positive blood culture. Together, these results point to the relevance of this cohort for validation of cord blood biomarkers resulting from antenatal encounters with etiological agents of intra-amniotic infection, inflammation and EONS.

Of the list of potential proteomic targets, the Applicant chose to validate those with a net change ≥3-fold (HpRP, Hp, AFP, VDBP, APOA4, APOE and APOH). Despite albumin depletion prior to 2D-DIGE, the Applicant noted consistent changes in 12 spots matching to albumin (72-45 kDa). Although albumin variants and fragments thereof could be true biomarkers, specific knowledge on antibody affinity against each of the peptides is lacking at this time. Thus, changes in serum albumin were indirectly validated through the non-immunological measure of total protein concentration.

The results of validation immunoassays and of additional relevant cord blood analytes (total protein and IL-6 concentrations) are presented in Table 6. Cord serum concentration of Hp&HpRP but not of the other proteomic targets were significantly elevated in newborns with EONS. Neonates with EONS also had lower total cord blood protein and a higher cord blood IL-6 level. However, after correction for GA at birth only Hp&HpRP and IL-6 immunoreactivity remained independently impacted by EONS status (GA corrected P=0.001 for both). The above findings led the Applicant to conclude that exposure of the fetus to infection/inflammation resulting in EONS elevates fetal Hp&HpRP along with IL-6 immunoreactivity.

Figure 20:
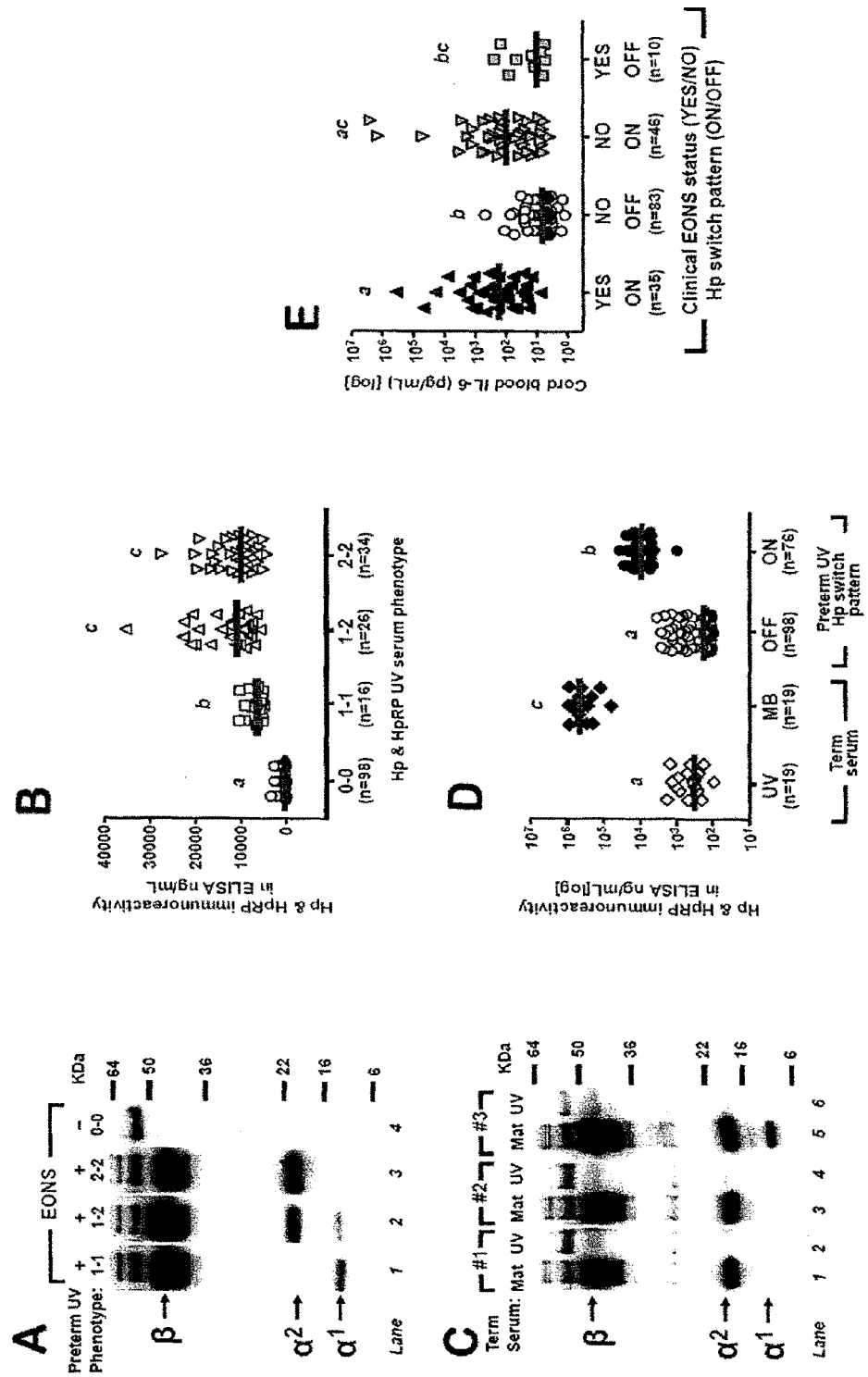
FIG. 20A-20E show, respectively, representative Western blots of cord blood serum from newborns with EONS (20A); results of an ELISA (20B); a representative western blot of 3 maternal-fetal pairs (20C); ELISA results (20D); and results of assessment of cord blood IL-6 levels (20E).

Western blotting of cord blood Hp&HpRP immunoreactivity Expression of Hp is developmentally regulated. Specifically, prior to the work described herein, Hp was considered near absent at birth with a switching to the adult level within the first year of life.[36,37] Thus, the Applicant's discovery that cord blood Hp&HpRP immunoreactivity was elevated in preterm newborns affected by EONS required further validation by Western blotting. FIG. 20A shows representative Western blots of cord blood serum newborns with EONS (Lanes 1-3). The conspicuous immunoreactive band corresponding to the β-chain (~42 kDa) is consistent with Applicant's defined switched-on Hp pattern. The band ~9 kDa (Lanes 1&2) corresponds to the α1-chain, whereas the band at ~20 kDa (Lanes 2-3) corresponds to the α2-chain. The cord blood samples shown in Lanes 1-3 are representative for the phenotypes Hp1-1, 1-2 and 2-2, respectively. A Western blot from a newborn without EONS is shown in Lane 4. As shown, the Hp switch-on pattern was absent (switched-off, consistent with in this case with Hp 0-0 phenotype) despite similar GA at birth. The Applicant found that a significantly higher number of neonates with EONS in the validation cohort displayed the Hp switched-on pattern (Yes EONS: 78% (35/45) vs. No EONS 36% (46/129), P<0.001). Among preterm newborns with switched-on Hp pattern (n=81), the distribution of Hp phenotypes was as follows 6.0% Hp0-0 (5/81, only the β-chain detected), 19.3% (16/81) Hp1-1, 32.5% (26/81) Hp1-2, and 42.1% (34/81) Hp2-2.

There was a significant direct correlation between the total optical density of Hp&HpRP immunoreactivity by Western blot and by ELISA (R=0.886, P<0.001). Cord blood samples with a switched-off pattern (Hp 0-0) had significantly lower ELISA immunoreactivity compared to all other 3 phenotypes (P<0.001, FIG. 20B). A Hp&HpRP cord blood concentration >3,370 ng/mL was best in indicating a switched-on Hp pattern (ROC area: 0.998, 95% CI [93.5-100]). Among samples with switched-on patterns the Hp phenotype impacted on ELISA immunoreactivity with Hp1-1 measuring lower compared to both Hp1-2 (P<0.001) and Hp2-2 (P=0.002) (FIG. 20B), independent of neonatal race, gender and GA at birth (multivariate corrected P=0.011).

To provide further evidence that Hp&HpRP can be switched-on prematurely in a select group of preterm newborns, Applicant performed both Western blotting and ELISA on a consecutive group of maternal and cord blood samples retrieved from healthy term newborns and their mothers. FIG. 20C shows a representative Western blot of 3 maternal-fetal pairs. All the healthy term babies (0/19) displayed a switched-off cord blood Hp pattern (Hp 0-0). This was in contrast to their mothers who all showed present Hp chains as expected for adult subjects. ELISA results confirmed the marked difference in immunoreactivity (>3 orders of magnitude) between maternal and cord serum of healthy term women (P<0.001, FIG. 20D). Preterm newborns with Hp switched-off pattern had similar ELISA immunoreactivity with healthy term newborns (P=0.189). Conversely, preterm newborn with switched-on pattern had significantly higher Hp&HpRP immunoreactivity compared to the above groups (P<0.001), albeit lower than the adult samples (P<0.001).

Relationships of cord blood Hp&HpRP with IL-6 IL-6 is a known transcriptional activator of Hp expression.[38] As shown in FIG. 20E, neonates who displayed the Hp switched-on pattern had significantly elevated cord blood IL-6 levels irrespective of clinical EONS diagnosis (P<0.001). Cord blood IL-6 levels were lower in the groups of neonates with Hp switched-off pattern. In a multivariate analysis cord blood IL-6 was independently impacted by the Hp switch-on pattern (P<0.001), number of expressed Hp2 alleles (none for Hp0-0 or Hp1-1, one for Hp 1-2 and two for Hp2-2 phenotype; P=0.005) and a clinical diagnosis of EONS (P=0.003).

Figure 21:
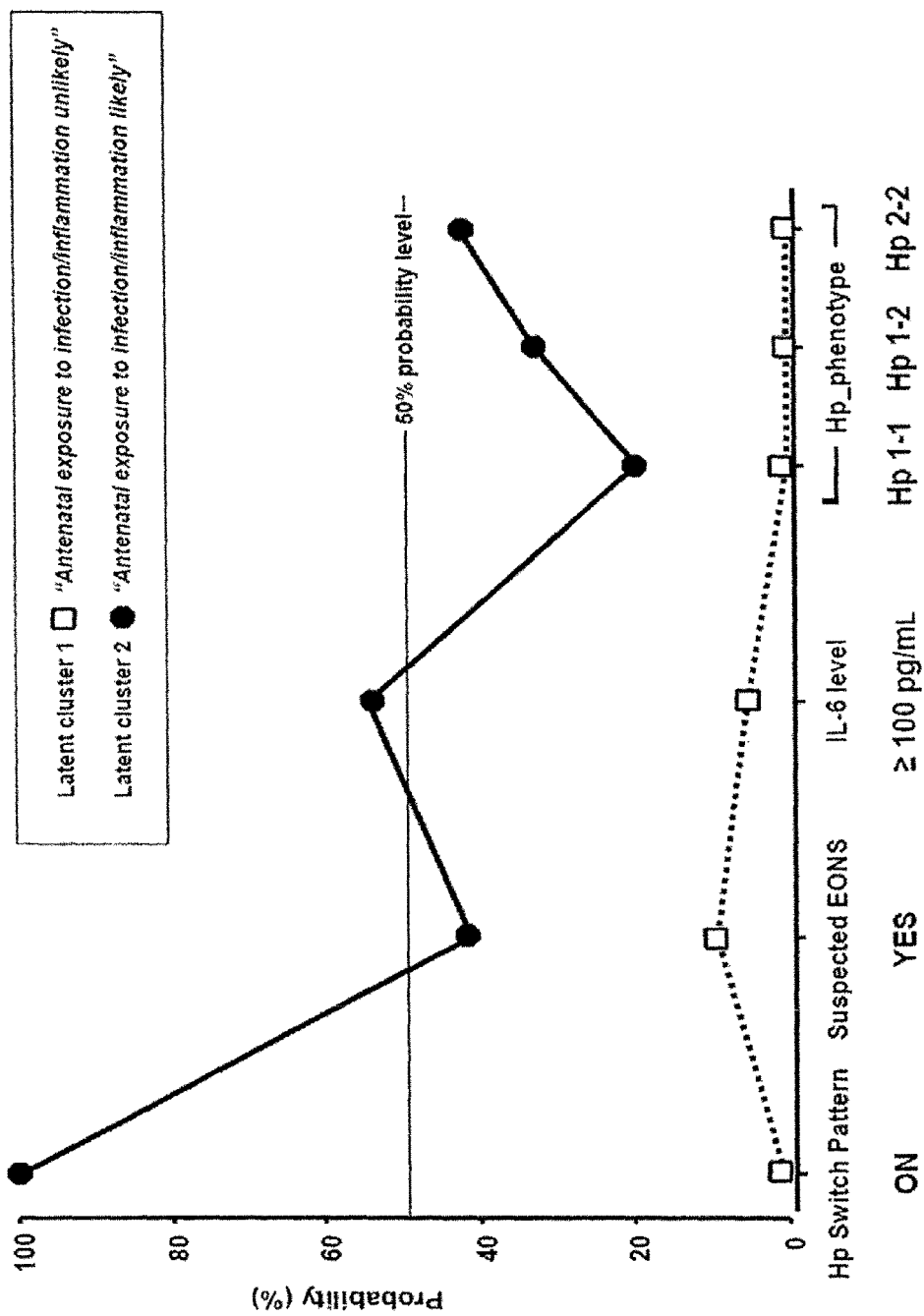
FIG. 21 is a graphic representation of latent class cluster analysis.

Latent class cluster analysis to identify the probability of "antenatal exposure to infection/inflammation" Chosen indicator variables were Hp switch pattern, IL-6 level and suspected EONS. Covariates were neonatal race, gender, Hp phenotype, GA, and membrane status. LCA analysis found a 2-cluster model as optimal solution to the newborn population (see Supplemental Methods, Supplemental Results, Table 7, details). All three indicators contributed significantly (P<0.001) albeit unequally at data clustering (Table 8). Most of the input was achieved from Hp switching (GK-θ: 0.98) and the least from suspected EONS (GK-θ: 0.14). Of the covariates, only Hp phenotype showed statistical disparity between the two clusters (P=0.002). The discriminative indicators, significant covariates and probability with which their modal characteristics (i.e., switch-on or switch-off) are expected to manifest in each of the two latent clusters are shown in FIG. 21. Cluster 1 was characterized by very low probability for Hp switch-on pattern and low probabilities for suspected EONS and elevated cord blood IL-6 (>100 pg/mL). Cluster 2 was characterized by a high probability for Hp switch-on pattern suggesting that our biomarkers could be a useful addition to the work-up of premature neonates at birth to increase the level of confidence that the newborn was exposed or not to an antenatal infections agent. Bayesian posterior probabilities of antenatal exposure to infection/inflammation derived from the analysis of our study population are shown in Table 9.

Figure 22:
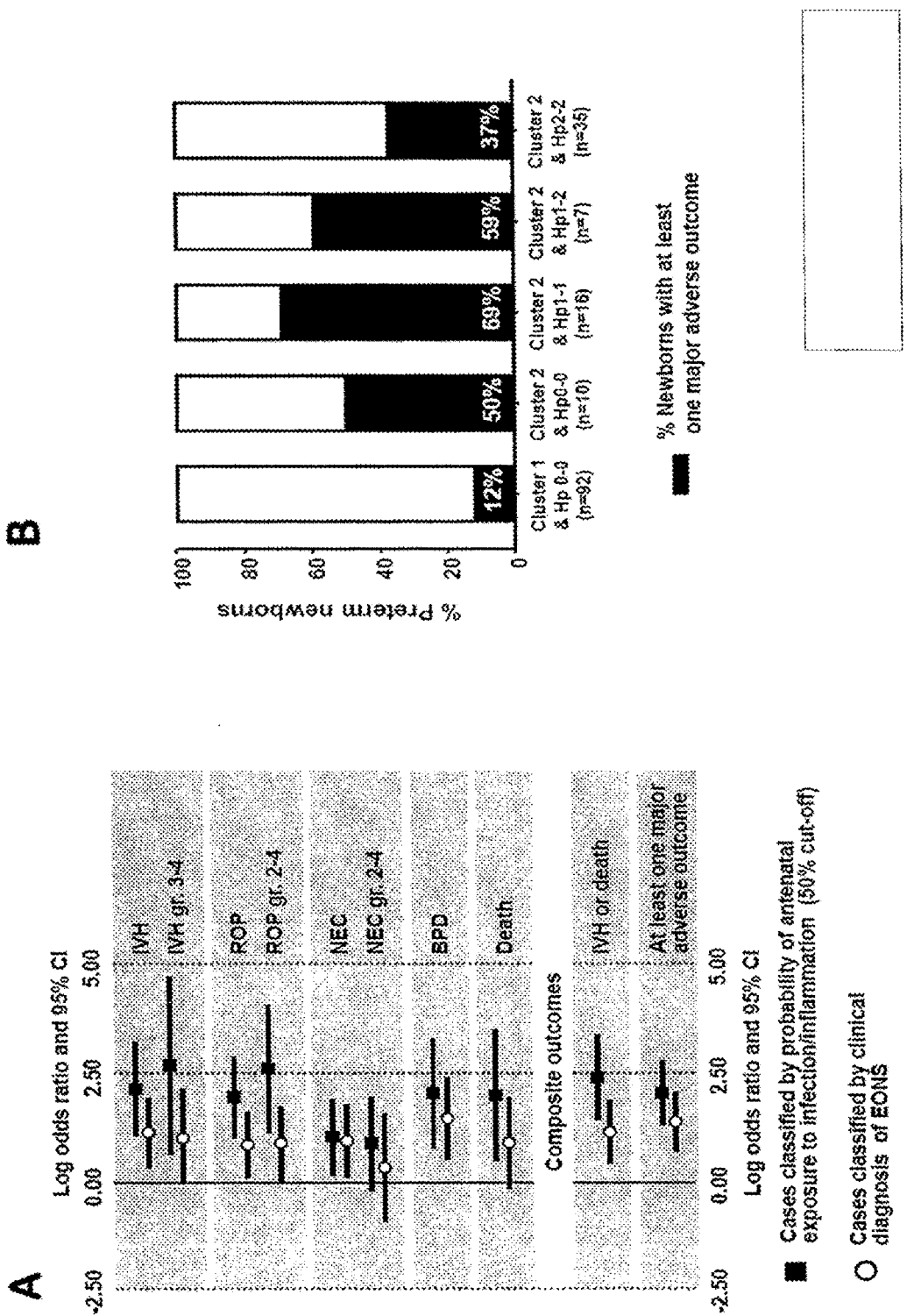
FIGS. 22A and 22B show, respectively, classification of cases based on probability of antenatal exposure to infection/inflammation (50% cut-off) and cases classified by clinical diagnosis of EONS (22A) and a disparity in adverse neonatal outcomes based on antenatal exposure to infection/inflammation and Hp phenotype (22B).
Figure 23:
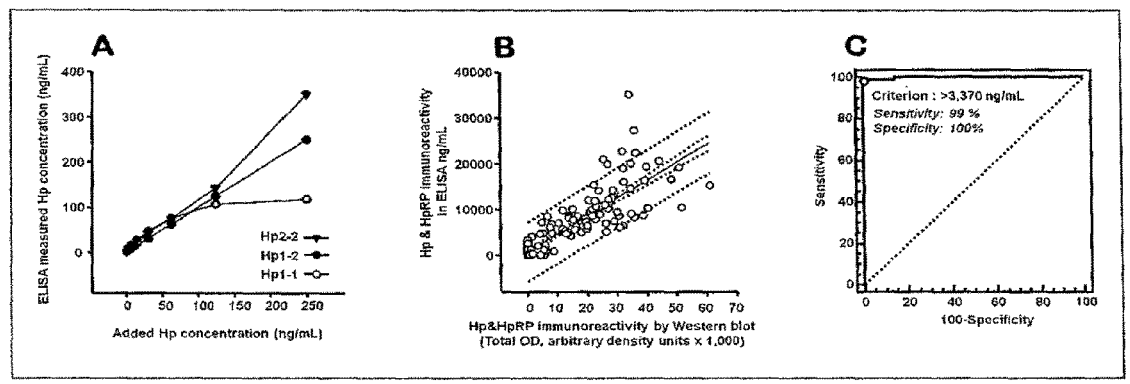
FIG. 23A-23C shows considerations for determination of cord blood Hp & HpRP immunoreactivity.
Figure 24:
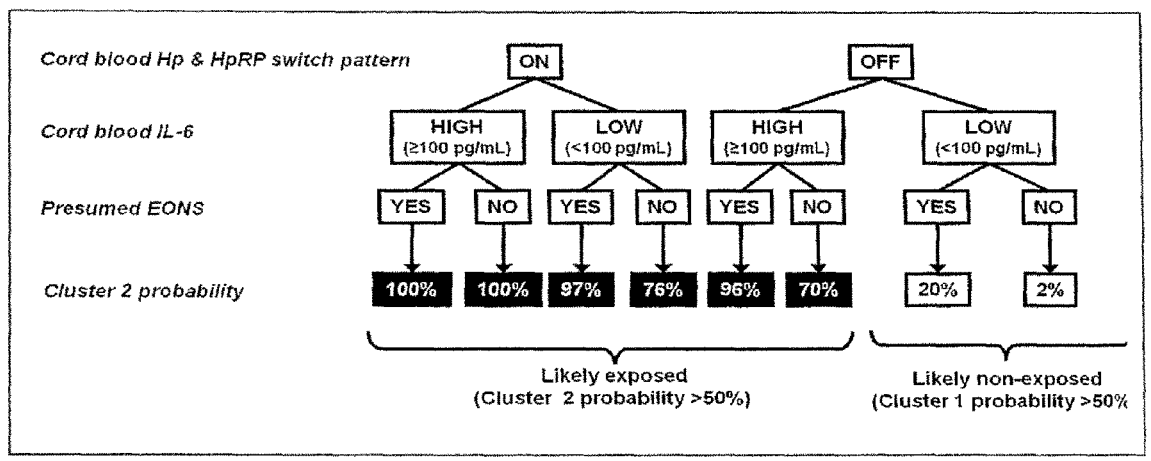
FIG. 24 is a work-up diagram to cluster newborns on probability of "antenatal IAI exposure" and lack thereof.

Relationships of antenatal exposure to infection/inflammation with neonatal outcome Each case was distributed to either cluster 1 (exposure unlikely, n=92) or cluster 2 (exposure likely, n=88) based on a posterior probability cut-off=50% (equivalent to both categories equally probably and to a useless algorithm). The agreement between the Applicant's classification of antenatal infectious exposure and a clinical diagnosis of EONS was "moderate" (Φ=0.416, P<0.001). The Applicant's classification agreed with the clinical diagnosis in 69% (124/180) of cases. However, the new algorithm identified a high probability of exposure in 27% (48/180) of cases deemed clinically EONS negative. The remaining 4% (8/180) of cases had been classified clinically as positive EONS, yet the Applicant's model argued against the exposed state. This suggests that, based on current clinical practice, ~30% of newborns are potentially misdiagnosed with respect to antenatal exposure to infection/inflammation. Table 10 presents parameters of association between the Applicant's new model and indicators of neonatal morbidity or mortality. Applicant determined that for all adverse outcomes, with the exception of NEC, the ORs increased in the context of the new model compared to the traditional diagnosis of EONS (FIG. 22A). The lower NNH resulting from the Applicant's classification suggests that inclusion in cluster 2 (e.g, likely exposed), and especially by a switched-on Hp at the time of birth, is a stronger risk factor of neonatal morbidity than the current clinical classification of EONS.

In multivariate logistic regression the two composite newborn outcomes were significantly predicted by the combination of GA (P<0.001), antenatal exposure to infection/inflammation (cluster 2 probability >50%, P<0.001) and the Hp phenotype (P<0.05). Excluded from the model were: cord blood IL-6, Hp&HpRP immunoreactivity by ELISA, suspected EONS or clinical diagnosis of EONS.

FIG. 22B demonstrates a disparity in adverse neonatal outcomes based on antenatal exposure to infection/inflammation and Hp phenotype. Among exposed newborns, those switched-on to a Hp2-2 phenotype had the lowest incidence of major morbidities (Chi square P=0.043) despite no difference in GA at birth (P=0.410).

Discussion

Isolation and growth in culture of bacteria isolated from a central body fluid (usually blood) is the current standard method to diagnose EONS.[39] Yet, 48 to 72 hours may pass until bacterial growth can be confirmed. Because even a 4-hour delay in initiation of antibiotics may increase mortality rate in culture proven sepsis, NBSCU around the world initiate universal "empirical antibiotic therapy" based on maternal risk factors or clinical suspicion of EONS.[40,41] In most circumstances if blood culture results are not reported as positive by 48 to 72 hours, then in the absence of neonatal clinical symptoms of sepsis, antibiotics are discontinued.[40,41,42] There are significant downsides to this therapeutic approach. Frequent monitoring of blood levels, renal and oto-toxicity, increase risk of NEC are just a few.[43,44] Not surprisingly, there is also concern that continuing this practice will further change the diversity of microbes in NBSCUs, and will pose in the future a significant therapeutic challenge.[42]

In the context of the narrow spectrum of currently identifiable bacteria,[45] attempts have been made to use physiologic parameters such as hematologic indices and cytokine profiles (e.g., IL-6, IL-1β, IL-8 and TNF-α), non-specific acute-phase reactants (e.g., C-reactive protein, fibrinogen, amyloid protein A, procalcitonin), neutrophil CD64 marker, and PCR to identify neonates with EONS.[46,47,48,49] Unfortunately, a large body of clinical evidence suggest that no currently available test or combination of tests have sufficient sensitivity and specificity to ensure treatment of infected newborns while allowing non-treatment of the non-infected infants.

There are several reasons why it is difficult to accurately diagnose EONS and why many newborns are treated with empiric antibiotics even when unnecessary. First is that bloodstream infection in EONS is fluctuates widely from 8% to 73%.[50] Many newborns with "suspected EONS" have non-specific clinical manifestations (lethargy, apnea, respiratory distress, hypoperfusion and shock) but negative cultures.[51] A second obstacle is technical and relates to the narrow spectrum of pathogens sought in microbiology laboratories. For example, searching for *Ureaplasma* and *Mycoplasma* spp. is not part of routine sepsis work-up in neonates. A study that evaluated the frequency of umbilical cord blood infections with these species found that that 23% of newborns born <32 weeks tested positive for these pathogens. It is also plausible that analogous to PTB, additional uncultivated and difficult-to-cultivate species could be also etiological agents of EONS.[52,53] In point, by using an amniotic fluid proteomic fingerprint (the MR score) as gold standard of intra-amniotic inflammation, the Applicant observed that by using culture-independent methods of bacterial identification (16SrRNA PCR) many women presenting with signs of PTB and "severe inflammation" with negative cultures had in fact evidence of bacterial footprints in amniotic fluid.[53,54,55,56,57] Furthermore, most samples of amniotic fluid with positive cultures contained additional bacteria compared to those found by cultures.[55] In fact, 60% of species detected by culture-independent methods were missed by general laboratory cultures. This study was in agreement with earlier reports suggesting that PCR can detect bacterial DNA in up to 60% of pregnancies complicated by PTB,[58,59] yet cautioning that its use alone cannot discriminate between in vivo infection and ex vivo contamination and thus may result in unnecessary early deliveries. Moreover, by clone analysis we determined that the missed prokaryotes belonged to the class of "uncultivated" and "difficult-to-cultivate" species.[55] Together, this evidence suggests that in pregnancies complicated by PTB, the fetus may encounter a wider microbial diversity that it was previously thought.

Several studies in adults reported links between particular Hp phenotypes and susceptibility to diseases with either infectious or oxidative stress components. Thus we sought to investigate whether a more complex biomarker signature accounting for both Hp phenotype and Hp&HpRP immunoreactivity has improved predictive value for EONS and for other prematurity-related complications.

Clinical assessment of premature newborns is notoriously non-specific. In the Present state of clinical practice, hematological indices are the only aids the neonatologist has available with respect to clinical decisions to be made shortly after birth of each newborn to prevent EONS complications (e.g., admission to NBSCU, i.v. antibiotic treatment and allocation of necessary resources). Given that results of cultures are not available at the time these decisions are taken, our LCA algorithm included "suspected" EONS (based solely on the implemented hematologic criteria) and cord blood indicators with potential for quick turnaround.

TABLE 3

2D-DIGE results and convergence of unambiguous identities by protein precursor into proteomics targets. (See column entitled "Protein precursor").

| IPI ID | Spot MW | Spot PI | Average DB score | Average ion score | Average % coverage | # Spots UP | # Spots DOWN | Protein precursor | SwissProt Acession | #Gels | Average fold UP | Average fold DOWN | Net change |
|---|---|---|---|---|---|---|---|---|---|---|---|---|---|
| NET CHANGE UP-REGULATED ||||||||||||||
| IPI00477597 | 38982.6 | 6.4 | 118 | 91 | 26 | 7 | 0 | HpRP | P00739 | 2 of 3 | 60 | 0 | 60 fold up |
| IPI00607707 | 43027.4 | 6.4 | 114 | 91 | 24 | 7 | 0 | Hp | P00738 | 2 of 3 | 33 | 0 | 33 fold up |
| IPI00641737 | 46693.4 | 6.3 | 419 | 345 | 42 | 18 | 0 | | | | | | |
| IPI00478493 | 38427.3 | 6.1 | 426 | 344 | 50 | 18 | 0 | | | | | | |
| IPI00431645 | 31361.8 | 8.5 | 460 | 376 | 68 | 15 | 0 | | | | | | |
| IPI00022443 | 68633.0 | 5.5 | 393 | 270 | 54 | 5 | 0 | AFP | P02771 | 2 of 3 | 7 | 0 | 7 fold up |
| IPI00742696 | 52882.9 | 5.3 | 732 | 622 | 56 | 1 | 1 | VDBP | P02774 | 2 of 3 | 8 | −6 | 2 fold up |
| NET CHANGE DOWN-REGULATED ||||||||||||||
| IPI00022434 | 71657.6 | 6.3 | 765 | 590 | 67 | 2 | 9 | ALB | P02768 | 3 of 3 | 4 | −10 | 6 fold down |
| IPI00745872 | 69321.5 | 5.9 | 708 | 544 | 64 | 3 | 9 | | | | | | |
| IPI00878517 | 56175.3 | 6.8 | 642 | 517 | 64 | 2 | 9 | | | | | | |
| IPI00384697 | 47329.7 | 6.0 | 531 | 430 | 62 | 2 | 9 | | | | | | |
| IPI00216773 | 45130.4 | 5.8 | 390 | 289 | 68 | 1 | 7 | | | | | | |
| IPI00304273 | 45371.5 | 5.3 | 382 | 189 | 79 | 2 | 1 | APOA4 | P06727 | 2 of 3 | 9 | −4 | 5 fold down |
| IPI00847179 | 45344.5 | 5.3 | 350 | 172 | 75 | 2 | 1 | | | | | | |
| IPI00021842 | 36131.8 | 5.7 | 841 | 576 | 120 | 0 | 2 | APOE | P02649 | 2 of 3 | 0 | −3 | 3 fold down |
| IPI00878953 | 32537.8 | 7.0 | 591 | 421 | 101 | 0 | 2 | | | | | | |

TABLE 3-continued

2D-DIGE results and convergence of unambiguous identities by protein precursor into proteomics targets. (See column entitled "Protein precursor").

| IPI ID | Spot MW | Spot PI | Average DB score | Average ion score | Average % coverage | # Spots UP | # Spots DOWN | Protein precursor | SwissProt Acession | #Gels | Average fold UP | Average fold DOWN | Net change |
|---|---|---|---|---|---|---|---|---|---|---|---|---|---|
| IPI00879456 | 24888.0 | 5.8 | 448 | 292 | 109 | 0 | 2 | | | | | | |
| IPI00298828 | 38272.7 | 8.3 | 482 | 406 | 58 | 4 | 4 | | | | 3 | −6 | 3 fold down |
| | | | | | NO NET CHANGE | | | | | | | | |
| IPI00478003 | 163174.9 | 6.0 | 765 | 572 | 37 | 3 | 1 | A2MG | P01023 | 2 of 3 | 2 | −2 | zero |

Abbreviations:
HpRP, haptoglobin-related protein;
Hp, haptoglobin;
AFP, α-fetoprotein;
VDBP, vitamin-D binding-protein;
ALB, albumin;
APOA4, apolipoprotein-A4;
APOE, apolipoprotein-E;
APOH, apolipoprotein-H;
A2MG; A2MG, α-microglobulin.

TABLE 4

Demographic, clinical and outcome characteristics of pregnancies that provided cord blood for the $1^{st}$-level validation (n = 174).

| | VALIDATION COHORT | | |
|---|---|---|---|
| Variable | NO EONS n = 129 | YES EONS n = 45 | P Value |
| Maternal demographic and clinical characteristics at enrollment (amniocentesis) | | | |
| Maternal age, years † | 30 [23-34] | 26 [21-34] | 0.157 |
| Gravidity † | 2 [1-4] | 3 [2-4] | 0.394 |
| Parity † | 1 [0-2] | 1 [0-2] | 0.884 |
| Race § | | | 0.090 |
| Caucasian | 58 (45) | 11 (24) | |
| African-American | 44 (34) | 19 (42) | |
| Hispanic | 20 (16) | 12 (27) | |
| Other | 7 (5) | 3 (7) | |
| Non-Caucasian race § | 71 (55) | 34 (76) | 0.025 |
| Gestational age, weeks † | 29 [26-32] | 26 [25-29] | <0.001 |
| Cervical dilation, cm † | 1 [0-3] | 3 [1-4] | 0.001 |
| Ruptured membranes § | 81 (63) | 25 (56) | 0.497 |
| Uterine contractions § | 56 (43) | 20 (44) | 0.957 |
| History of preterm birth § | 33 (26) | 18 (40) | 0.101 |
| Clinical chorioamnionitis § | 11 (9) | 5 (11) | 0.828 |
| Antenatal drug treatments/exposure | | | |
| Steroids § | 119 (92) | 45 (100) | 0.121 |
| Antibiotics § | 107 (83) | 39 (87) | 0.727 |
| Tocolysis § | 53 (41) | 22 (49) | 0.462 |
| Magnesiun sulfate § | 42 (32) | 20 (44) | 0.210 |
| Progesterone during pregnancy § | 18 (14) | 10 (22) | 0.287 |
| Pregnancy outcome characteristics | | | |
| Amniocentesis-to-delivery, hours † | 24 [8-111] | 8 [5-20] | 0.003 |
| Indicated preterm delivery § | 66 (51) | 31 (69) | 0.059 |
| Gestational age at delivery, weeks † | 30 [28-33] | 26 [25-30] | <0.001 |
| Birthweight, grams † | 1.450 [1.090-1.985] | 920 [770-1.517] | <0.001* |
| Cesarean delivery § | 58 (45) | 14 (33) | 0.236 |
| Apgar score at 1 minute † | 8 [5-9] | 5 [3-7] | <0.001 |
| Apgar score at 5 minutes † | 9 [8-9] | 8 [6-8] | <0.001* |
| 1 min Apgar < 7 § | 42 (32) | 29 (64) | <0.001* |
| 5 min Apgar < 7 § | 14 (10) | 16 (36) | <0.001* |
| Newborn male gender § | 62 (48) | 20 (44) | 0.806 |

† Data presented as median [interquartile range] and analyzed by Mann Whitney tests.
§ Data presented as n (%) and analyzed by Chi square tests.
* Postnatal variable where correction for gestational age at birth in multivariate analysis resulted in a non-significant P value for EONS.

The bold font indicates variables remaining significant after GA correction.

TABLE 5

Laboratory analyses used for clinical management and/or counseling of pregnancies that provided cord blood for the 1$^{st}$-level validation (n = 174).

| | VALIDATION COHORT | | |
|---|---|---|---|
| Variable | NO EONS n = 129 | YES EONS n = 45 | P value |
| Amniotic fluid analysis | | | |
| Glucose. mg/dL † | 19 [10-32] | 3 [2-13] | <0.001 |
| LDH, U/L † | 260 [158-583] | 744 [270-2,365] | <0.001 |
| WBC, cells/mm³ † | 24 [4-540] | 444 [59-1,840] | <0.001 |
| Positive Gram stain § | 27 (21) | 31 (69) | <0.001 |
| Positive microbial cultures § | 28 (30) | 36 (80) | <0.001 |
| Umbilical cord blood analysis | | | |
| Arterial pH † | 7.31 [7.28-7.34] | 7.32 [7.25-7.35] | 0.972 |
| Arterial base deficit † | 4.4 [3.2-5.5] | 6.1 [3.5-9.4] | 0.074 |
| Venous pH | 7.36 [7.33-7.39] | 7.38 [7.28-7.40] | 0.440 |
| Venous base deficit | 3.8 [2.2-5.1] | 4.8 [2.4-8.0] | 0.143 |
| Arterial or Venous pH < 7 § | 1 (1) | 2 (6) | 0.287 |
| Placental histological analysis | | | |
| Chorionic plate inflammation, stages II-III § | 60 (48) | 41 (91) | <0.001 |
| Amnionitis, stages 2-4 § | 46 (36) | 37 (82) | <0.001 |
| Choriodeciduitis, stages 2-4 § | 84 (66) | 42 (93) | <0.001 |
| Funisitis, stages 1-4 | 45 (35) | 30 (67) | <0.001 |
| Neonatal sepsis work-up | | | |
| WBC, cells × 1,000/mm³ † | 10 [8-14] | 15 [9.3-21] | 0.003 |
| Hemoglobin. mg/dL † | 15.1 [13.8-16.2] | 14 [12.6-15.4] | 0.004* |
| Hematocrit. % † | 46.1 [41.7-50.5] | 43.6 [39.2-47.9] | 0.014* |
| Platelets, cells × 1,000/mm³ † | 269 [222-308] | 236 [176-331] | 0.118 |
| Segmented neutrophils, % † | 36 [25-44] | 27 [19-39] | 0.010 |
| Immature neutrophils (bands), % † | 2 [0-6] | 17 [13-25] | <0.001 |
| Lymphocytes, % † | 44 [32-57] | 29 [22-45] | <0.001 |
| Monocytes. % † | 11 [7-15] | 10 [8-15] | 0.901 |
| Absolute neutrophil count (ANC), cells/mm³ | 3.550 [2.164-6.166] | 4.028 [2.148-6.778] | 0.688 |
| Absolute band count (ABC), cells/mm³ | 255 [0-674] | 2,560 [1,456-3,808] | <0.001 |
| Immature/total neutrophil (I:T) ratio, % | 2 [0-6] | 17 [13-25] | <0.001 |
| Suspected EONS § | 0 (0) | 41 (91) | <0.001 |
| Culture positive EONS § | 0 (0) | 7 (16) | <0.001 |

† Data presented as median [interquartile range] and analyzed by Mann Whitney tests.
§ Data presented as n (%) and analyzed by Chi square tests.
* Postnatal variable where correction for gestational age at birth in multivariate analysis resulted in a non-significant P value for EONS.

The bold font indicates variables remaining significant after GA correction.

TABLE 6

Cord blood analytes measured in the 1$^{st}$-level validation (n = 174).

| | VALIDATION COHORT | | |
|---|---|---|---|
| Variable | NO EONS n = 129 | YES EONS n = 45 | P value |
| Potential cord blood proteomic biomarkers | | | |
| Hp&HpRP, ng/mL | 666.1 [16.9-6,818.0] | 9,013.1 [4,448.6-12,463.4] | <0.001 |
| AFP, µg/nL | 354.7 [213.0-606.4] | 320.1 [154.0-466.4] | 0.258 |
| VDBP, total, µg/mL | 381.0 [270.4-477.3] | 438.4 [335.3-522.9] | 0.145 |
| VDBP, actin bound, µg/mL | 204.7 [126.1-275.1] | 232.1 [151.8-366.3] | 0.132 |
| VDBP, actin free. µg/mL | 144.3 [111.8-192.6] | 161.4 [117.5-202.9] | 0.549 |
| APOA4, ng/mL | 2,372.8 [1,850.1-2,836.1] | 2,143.0 [1,836.6-2,577.3] | 0.338 |
| APOE, µg/mL | 284.2 [215.0-396.9] | 331.1 [203.6-484.2] | 0.404 |
| APOH, µg/mL | 136.8 [121.2-166.3] | 145.3 [94.4-177.2] | 0.950 |

TABLE 6-continued

Cord blood analytes measured in the 1ˢᵗ-level validation (n = 174).

| | VALIDATION COHORT | | |
|---|---|---|---|
| Variable | NO EONS n = 129 | YES EONS n = 45 | P value |
| Other research analytes | | | |
| Total protein, mg/mL | 41.9 [36.6-49.4] | 35.9 [31.6-43.6] | 0.008* |
| IL-6, pg/mL | 8.1 [5.6-36.6] | 106.5 [22.3-506.9] | <0.001 |

†Data presented as median [interquartile range] and analyzed by Mann Whitney tests.
§Data presented as n (%) and analyzed by Chi square tests.
*Postnatal variable where correction for gestational age at birth in multivariate analysis resulted in a non-significant P value for EONS.

The table above should read "Total protein" which means: Despite albumin depletion prior to 2D-DIGE, Applicant noted consistent changes in 12 spots matching to albumin (45-72 kDa), Table 3). Although albumin variants and fragments thereof could be true biomarkers, specific knowledge on antibody affinity against each of the peptides is lacking at this time. Thus, changes in serum albumin are indirectly validated through the non-immunological measure of total protein concentration.

TABLE 7

Fit indices for possible latent-class analysis (LCA) models.

| Model | # clusters | LL | BIC (LL) | AIC (LL) | Npar | $L^2$ | df | P value | Class Err |
|---|---|---|---|---|---|---|---|---|---|
| Model1 | 1 | −329.54 | 674.65 | 665.07 | 3 | 451.23 | 177 | <0.001 | 0.000 |
| Model2 | 2 | −177.84 | 428.38 | 383.68 | 14 | 147.84 | 166 | 0.84 | 0.002 |
| Model3 | 3 | −166.34 | 462.50 | 382.68 | 25 | 124.84 | 155 | 0.97 | 0.032 |
| Model4 | 4 | −157.27 | 501.49 | 386.55 | 36 | 106.70 | 144 | 0.99 | 0.039 |

Abbreviations: LL, log-likelihood; BIC, Bayesian Information Criterion; AIC, Akaike Information Criterion. These statistical indicators (information criteria) weigh out the fit and parsimony by adjusting the LL to account for the number of parameters in the model. The lower the BIC and AIC values, the better the model. Npar, number of parameters; $L^2$, likelihood-ratio goodness-of-fit value for the current model. df, degrees of freedom; Class Err, classification error. When classification of cases is based on modal assignment (to the class having the highest membership probability), the proportion of cases that are expected to be misclassified is reported by this statistical indicator. The closer this value is to 0 the better.

TABLE 8

Contribution of indicator variables in discriminating between latent clusters and partitioning of covariates between the clusters.

| Variable | Variable levels | Wald statistic | P value | Goodman-Kruskal tau b |
|---|---|---|---|---|
| Indicators | | | | |
| Hp&HpRP switch pattern | 2 (ON or OFF) | 14.88 | <0.001 | 0.98 |
| Cord blood IL-6 ≥ 100 pg/mL | 2 (YES or No) | 36.63 | <0.001 | 0.30 |
| Suspected EONS | 2 (YES or NO) | 21.32 | <0.001 | 0.14 |
| Covariates | | | | |
| Hp phenotype | 4 (Hp0-0. 1-1. 1-2, 2-2) | 14.57 | 0.002 | NA |
| Gender | 2 (male or female) | 0.40 | 0.530 | NA |
| Race | 2 (Caucasian or not) | 1.97 | 0.160 | NA |
| GA at delivery | 2 (<30 wks or ≥30 wks) | 1.0 | 0.320 | NA |
| Membrane status | 2 (PPROM or intact) | 1.97 | 0.160 | NA |

Wald statistic values are provided to assess the statistical significance of each nominal parameter. A non-significant associated P value means that the indicator does not discriminate between the clusters in a statistically significant way.
Goodman Kruskal tau b (G-Kθ) is a more general coefficient of association between two nominal variables. In this case it represents the strength of association between the respective indicator and our latent variable "antenatal exposure to infection/inflammation". The closer to 1 the G-Kθ value, the higher the association and the contribution of the respective indicator in discriminating between latent clusters of the final model.

TABLE 9

Bayesian posterior probabilities of "antenatal IAI exposure" and lack thereof derived from the study population (n = 180).

| Clinical scenarios | | # Cases | Cluster 1 (likely unexposed) probability | Cluster 2 (likely exposed) probability |
|---|---|---|---|---|
| NO suspected EONS & Hp switch pattern OFF | IL-6 Low (<100 pg/mL) | 85 | 98% | 2% |
| NO suspected EONS & Hp switch pattern OFF | IL-6 High (≥100 pg/mL) | 3 | 30% | 70% |
| NO suspected EONS & Hp switch pattern ON | IL-6 Low (<100 pg/mL) | 23 | 24% | 76% |
| NO suspected EONS & Hp switch pattern ON | IL-6 High (≥100 pg/mL) | 26 | 0% | 100% |
| YES suspected EONS & Hp switch pattern OFF | IL-6 Low (<100 pg/mL) | 7 | 80% | 20% |
| YES suspected EONS & Hp switch pattern OFF | IL-6 High (≥100 pg/mL) | 2 | 4% | 96% |
| YES suspected EONS & Hp switch pattern ON | IL-6 Low (<100 pg/mL) | 15 | 3% | 97% |
| YES suspected EONS & Hp switch pattern ON | IL-6 High (≥100 pg/mL) | 19 | 0% | 100% |

TABLE 10

Comparison of case classification by probability of "antenatal IAI exposure" with current clinical diagnosis of EONS for prediction of short-term adverse neonatal outcomes ($2^{nd}$-level validation).

| Adverse outcomes | # of Preterm newborns | | Classification by probability of "antenatal exposure to infection/inflammation" | | | | | Classification by current clinical diagnosis of EONS | | | | |
|---|---|---|---|---|---|---|---|---|---|---|---|---|
| | Adverse outcome present | Total assessed | >50% Cluster 1 § | >50% Cluster 2 § | P value | OR [95% GI] | NNH | YES § | NO § | P value | OR [95% CI] | NNH |
| Individual outcomes | | | | | | | | | | | | |
| IVH | 30 | 170 | 4 (5%) | 26 (30%) | <0.001 | 8.7 [2.9-26.2] | 2.3 | 15 (12%) | 15 (31%) | 0.007 | 3.2 [1.4-7.3] | 3.8 |
| IVH grade 3-4 | 14 | 170 | 1 (1%) | 13 (15%) | 0.003 | 14.8 [1.9-115.8] | 2.1 | 7 (6%) | 7 (15%) | 0.114 | 2.8 [0.9-8.5] | 4.2 |
| ROP | 37 | 169 | 6 (7%) | 31 (36%) | <0.001 | 7.2 [2.8-18.5] | 2.4 | 21 (17%) | 16 (33%) | 0.040 | 2.4 [1.1-5.1] | 5.3 |
| ROP grade 2-4 | 24 | 169 | 2 (2%) | 22 (26%) | <0.001 | 13.9 [3.2-61.4] | 2.1 | 13 (11%) | 11 (23%) | 0.072 | 2.5 [1.0-6.0] | 4.9 |
| NEC | 27 | 170 | 8 (9%) | 19 (22%) | 0.027 | 2.9 [1.2-7.0] | 4.0 | 15 (11%) | 12 (25%) | 0.042 | 2.6 [1.1-6.1] | 4.8 |
| NEC grade 2-4 | 16 | 170 | 5 (5%) | 11 (12%) | 0.161 | 2.5 [0.8-7.5] | 4.6 | 8 (6%) | 8 (17%) | 0.055 | 1.4 [0.4-4.9] | 3.9 |
| BPD | 20 | 167 | 3 (3%) | 17 (22%) | <0.001 | 8.2 [2.3-29.3] | 2.3 | 9 (45%) | 11 (26%) | 0.003 | 4.6 [1.7-12] | 2.9 |
| Death | 15 | 180 | 2 (2%) | 13 (15%) | 0.005 | 7.8 [1.7-35.7] | 2.5 | 8 (6.0%) | 7.0 (15%) | 0.127 | 2.6 [0.9-7.7] | 4.6 |
| Composite outcomes | | | | | | | | | | | | |
| IVH or death | 39 | 180 | 5 (5%) | 34 (39%) | <0.001 | 11.0 [4.0-29.7] | 2.0 | 21 (16%) | 18 (38%) | <0.001 | 3.2 [1.5-6.7] | 4.0 |
| At least one major adverse outcome * | 56 | 180 | 11 (12%) | 45 (51%) | <0.001 | 7.7 [3.6-16.4] | 2.2 | 30 (23%) | 26 (54%) | <0.001 | 4.0 [2.0-8.1] | 3.2 |

* Includes newborns with at least one of the following outcomes: IVH grade 3-4. ROP grade 2-4. NEC grade 2-4. BPD and/or death.

§ Data presented as n (%) and analyzed by Chi square tests.

In multivariate logistic regression the two composite newborn outcomes were significantly predicted by the combination of GA (P < 0.001), antenatal exposure to infection/inflammation (cluster-2 probability >50%, P < 0.001) and the Hp phenotype (P < 0.05). Excluded from the model were: cord blood IL-6, Hp&HpRP immunoreactivity by ELISA, presumed EONS or clinical diagnosis of EONS.

Supplemental Methods a) Inclusion, exclusion criteria and clinical management of the study population. Inclusion criteria: preterm singleton fetus born alive whose mothers had an amniocentesis to rule out intra-amniotic infection and inflammation (IAI), admission to Yale Newborn Special Care Unit (NBSCU), appropriate growth for gestational age (GA), normal anatomic ultrasonographic survey. Exclusion criteria for maternal enrollment included: chronic medical conditions (i.e. hypertension, diabetes, thyroid disease), HIV, hepatitis or other viral infections, fetal structural abnormalities or fetal heart rate abnormalities requiring immediate intervention (i.e bradycardia, or prolonged variable decelerations). Inclusion criteria for the term group: uncomplicated term pregnancy with indication for cesarean delivery for breech or prior uterine scar, appropriately grown fetus, reassuring fetal heart rate prior to surgery. Uterine contractions and/or cervical change consistent with labor were additional exclusion criteria for the term group.

Following amniocentesis each patient was followed prospectively to delivery, independent of our research protocol. In the absence of signs or symptoms of clinical chorioamnionitis (fever >37.8° C., uterine tenderness and/or fetal tachycardia), amniotic fluid laboratory results suggestive of infection, non-reassuring fetal heart and/or abruption, PPROM was managed expectantly. Prior to delivery, corticosteroids for lung maturity and antibiotics were administered when clinically indicated [87]. Induction of labor or a surgical delivery was performed for indications such as amniotic fluid laboratory results traditionally considered to indicate IAI, [88] prolapsed umbilical cord and/or GA≥34 weeks [89]. The neonatology resuscitation team was present at the time of delivery for all newborns.

b) Biochemical, microbiological studies of AF and histology of the placenta. Clinical amniotic fluid laboratory tests were: glucose (cut-off of ≤15 mg/dL), lactate dehydrogenase (LDH, cut-off ≥419 U/L), white blood cell count (WBC, cut-off ≥50 cells/mm$^3$), Gram stain and microbiological cultures for aerobes, anaerobes, Ureaplasma and Mycoplasma species [90,91].

In all 180 cases, hematoxylin-and-eosin stained sections of extraplacental membranes (amnion and chorio-decidua), chorionic plate, chorio-decidua and umbilical cord were examined systematically for inflammation. Three histological stages of chorioamnionitis [92] (stage I: intervillositis, stage II: chorionic inflammation, and stage III: full-thickness inflammation of both chorion and amnion) were complemented by a previously described histological grading system that includes 4 grades of inflammation of the amnion, chorio-decidua and umbilical cord [93].

c) Diagnoses of early-onset neonatal sepsis (EONS) and of other short-term neonatal outcomes. A diagnosis of "presumed EONS" was based on presence of at least two of the following hematological criteria: absolute neutrophil count of <7,500 or >14,500 cells/mm$^3$; absolute band count >1,500 cells/mm$^3$; immature/total neutrophil (I:T) ratio>0.16; platelet count <150,000 cells/mm [94]. "Clinical EONS" was defined as the presence of presumed EONS corroborated with clinical symptoms and/or a positive blood culture result ("confirmed" EONS) at ≤72 hours after birth. All neonates with clinical EONS received i.v. antibiotics in NBSCU.

Evaluation for intra-ventricular hemorrhage (IVH) was done per institutional protocol using serial cranial ultrasounds on days 3, 7-10 and 30 of life [95]. Additional scans were performed if clinically indicated. The diagnosis and grading of IVH was established by experienced pediatric radiologists: grade 1, germinal matrix hemorrhage; grade 2, intraventricular blood without distension of the ventricular system; grade 3, blood filling and distending the ventricular system and grade 4, parenchymal involvement of hemorrhage, also known as periventricular venous infarction [95]. The ophthalmologist classified retinopathy of prematurity (ROP) in each eye according to the international classification [96]. Clinical, metabolic, hematologic and abdominal x-ray abnormalities (i.e pneumatosis intestinalis, portal venous gas) criteria were used to diagnose necrotizing enterocolitis (NEC) [97]. Bronhopulmonary dysplasia (BPD) was defined as need of receiving supplemental oxygen at 36 weeks' corrected postmenstrual age [98].

d) Two-dimensional differential gel electrophoresis (2D-DIGE). Identification of low abundant proteins was facilitated with the aid of albumin and IgG removal kit (GE Healthcare, Piscataway, N.J.), as previously described [99]. Cord blood proteins (50 µg) were labeled with either Cy5 (EONS group) or Cy3 (idiopathic PTB group). A reference pool (25 µg total protein) was labeled with Cy2 and used as internal control. For each pair, labeled samples were pooled and isoelectric focusing performed using an isoelectric point range of 3-10. SDS-PAGE on a 12% gel was performed for the second dimension. After spot detection, automatic background correction, spot volume normalization and volume ratio calculation, dye ratios were determined using DeCyder Extended Data Analysis software (GE Healthcare). Spots corresponding to ≥1.5-fold changes were robotically excised using the Ettan Spot Picker instrument (GE Healthcare) and subjected to automated in-gel tryptic digestion on the Ettan TA Digester (GE Healthcare). Automated MALDI-MS/MS spectra were acquired on the 4800 TOF/TOF proteomics analyzer (Applied Biosystems, Foster City, Calif.). The resulting peptide sequences along with spot information (Cy5/Cy3 ratio, location on gels) were uploaded in the web-accessible Yale Protein Expression Database (YPED http://medicine.yale.edu/keck/proteomics/yped/index.aspx) [100].

e) Immunoassay procedures. ELISA for haptoglobin and haptoglobin-related protein immunoreactivity (Hp&HpRP): Samples were diluted with blocking buffer (5% non-fat dry milk) 100, 1,000 or 10,000-fold (cord blood) or only 10,000-fold (maternal blood). A mixed phenotype Hp standard (Hp1-2, Sigma) was used to prepare a 7-point standard curve (250-3.9 ng/ml). Immunoassays for α-fetoprotein (AFP, R&D Systems, Minneapolis, Minn.), total vitamin D-binding protein (VDBP, ICL Inc, Newberg, Oreg.), actin-free VDBP (Alpco, Salem, N.H.), Apolipoprotein (Apo) A4 (Cederlane Labs, Burlington, N.C.), ApoE (MBL International, Woburn, Mass. and ApoH (Enzyme Research Laboratories, South Bend, Ind.) were performed according to each procedure summary. In pilot experiments we determined the cord blood serum optimal sample dilutions for AFP (50,000-fold), VDBP (total 50,000-fold, actin-free 5,000-fold), ApoA4 (100-fold), ApoE (500-fold) and ApoH (10,000-fold). IL-6 (Pierce-Endogen, Rockford, Ill.) was measured in amniotic fluid and cord blood to assess the inflammatory status of the two biological compartments. All samples were tested in duplicate by investigators unaware of case origin or outcome. Cord serum total protein was quantified using bicinchoninic acid (BCA) assay (Pierce Biotechnology, Rockford, Ill.).

f) Western blotting determination of Hp&HpRP, Hp switch-on pattern and Hp phenotype. SDS-PAGE gels (10-20%, InVitrogen, Carlsbad, Calif.) were loaded with equal amounts of cord blood protein (2 µg/lane) mixed 1:2 with reducing sample buffer (Bio-Rad, La Jolla, Calif.) and boiled for 5 min. After electrophoretic transfer, nitrocellulose membranes (Bio-Rad) were blocked with 5% milk and then incubated overnight at 4° C. rabbit anti-Hp polyclonal antibody (1:3,000, Sigma, St Louis, Mo.). Detection was performed using biotinylated goat anti-rabbit secondary antibody (1:5,000, Jackson Immunoresearch, West Grove, Pa.) followed by streptavidin-linked horseradish peroxidase, (1:8,000, Amersham Biosystems, Piscataway, N.J.), chemiluminescence (ECL-Plus, Amersham) and a timed 3 min. exposure to film (Kodak Biomax). Optical density of the bands of interest was analyzed with Image J software (NIH, http:\\rsb.info.nih-.gov). The results were expressed as the optical density of each band and as total optical density calculated from the sum of α- and β-chains. Purified Hp from blood of adults with known phenotypes (Hp1-1, Hp1-2 and Hp2-2, Sigma) were used as positive controls.

g) Statistical analysis. Normality testing was performed using the Shapiro-Wilk test. Data were compared with one-way ANOVA followed by Holm-Sidak method (parametric) or Kruskal-Wallis on ranks followed by Dunn's tests (non-parametric) as appropriate. Pearson correlations were used to measure co-linearity between the selected independent variables as well as other relevant relationships between dependent and independent variables. Comparisons between proportions were done with Chi-square tests. The phi-coefficient of correlation (Φ), an index of agreement for binary data was calculated. Stepwise multivariable regression analysis was used to determine concurrent relationships between variables and to correct for possible influences of gestational age and birthweight. Statistical analyses were performed with Sigma-Plot 11.0 (Systat Software), MedCalc (Broekstraat, Belgium), PASW Statistics (SPSS Inc) and Latent Gold 4.5. (Statistical Innovations) softwares. A P<0.05 was considered statistically significant.

Figure 5:
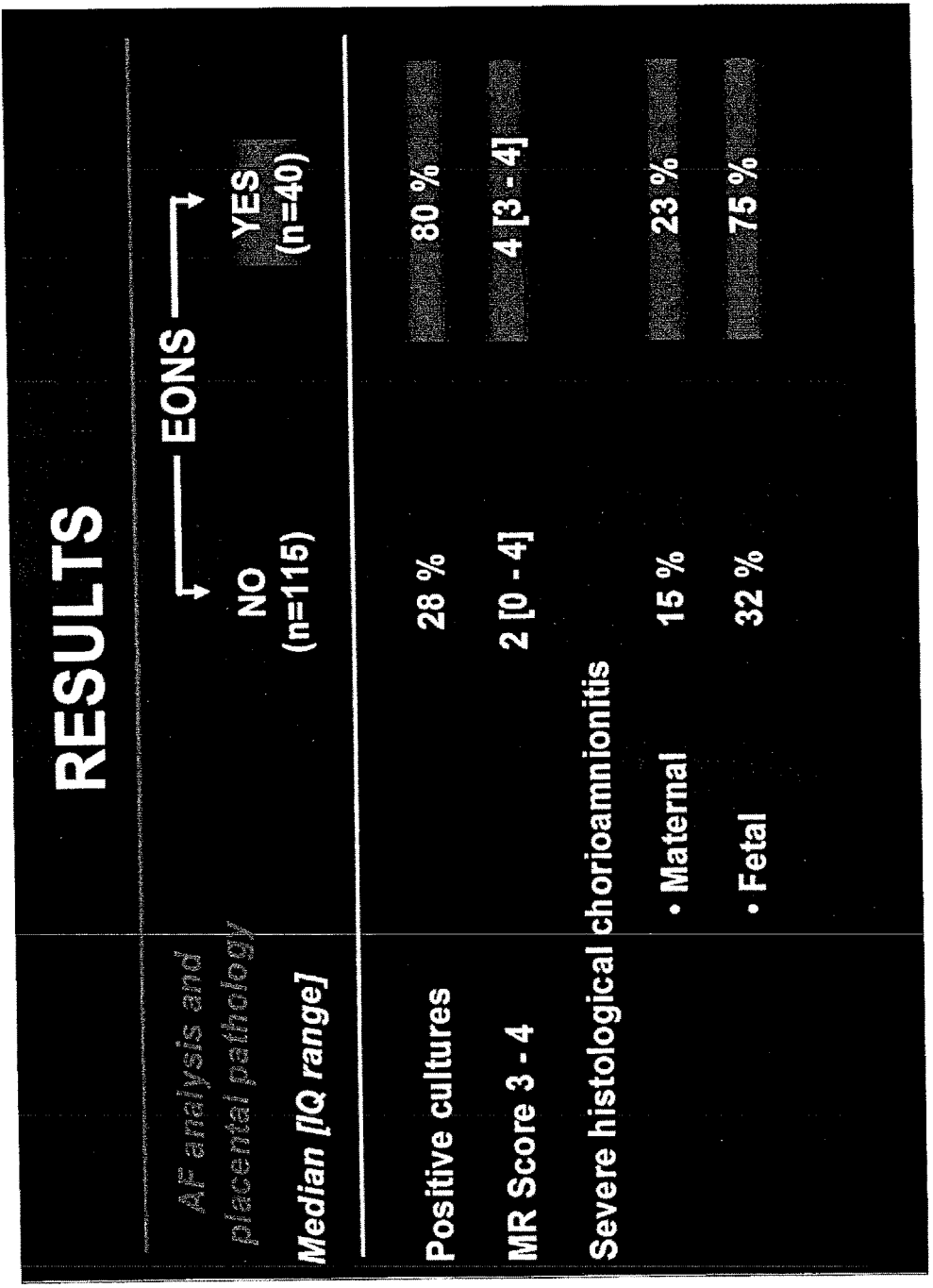
FIG. 5 shows further results of study described herein. Neonates with early onset sepsis were more frequently delivered in the setting of intra-amniotic infection and inflammation, as determined by microbial cultures and the MR score. Their placenta showed more often evidence of severe maternal and fetal inflammation.
Figure 7:
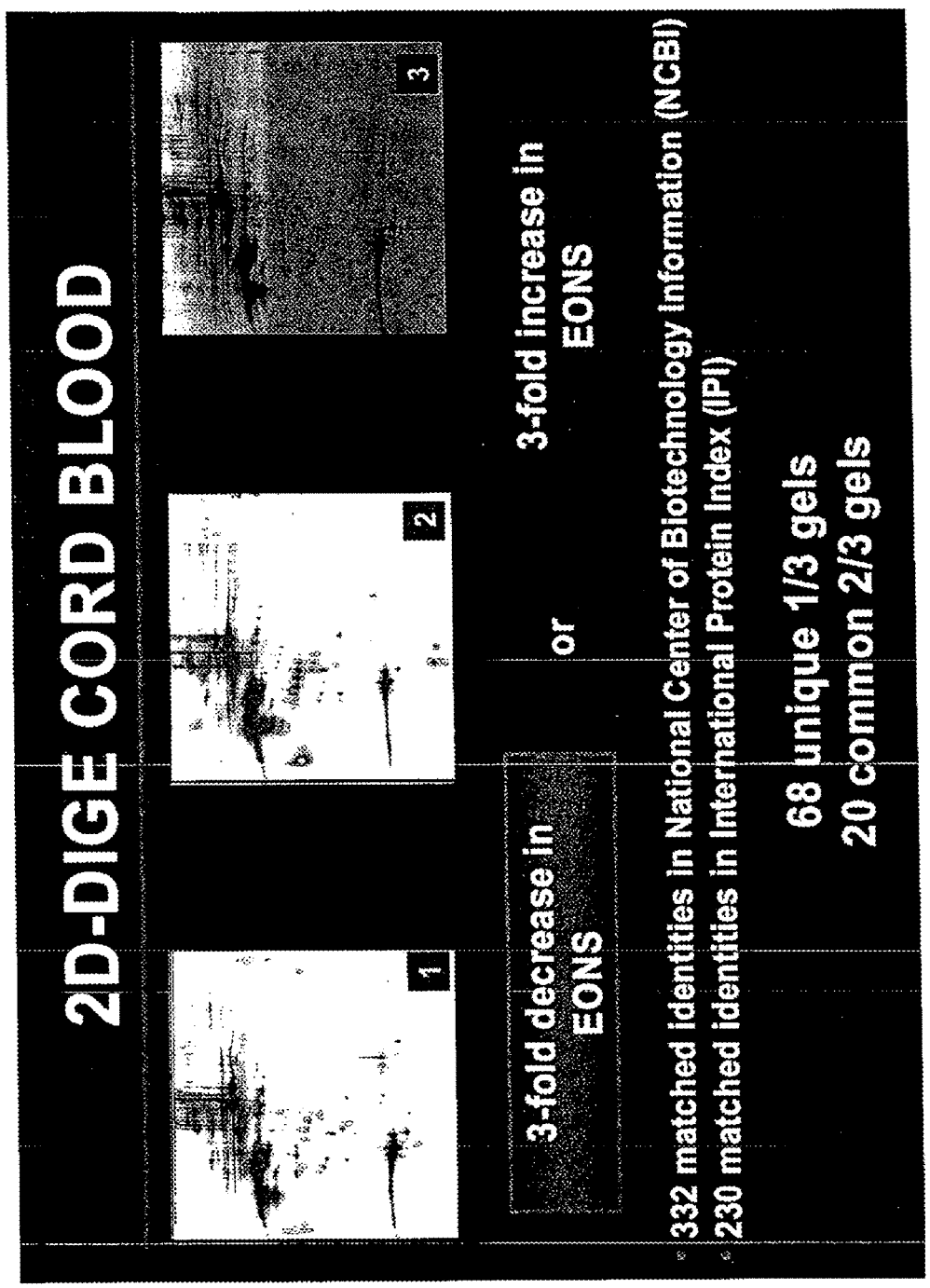
FIG. 7 presents 2 dimensional differential gel electrophoresis data. Three gels were created. Each display differentially expressed proteins or peptides between a neonate with proven sepsis and its matched control. For the purpose of this study we concentrated our attention on the proteins which were at least 3 fold down-regulated (marked in red) or 3 fold upregulated (marked in blue). 332 and 230 identities were matched in 2 database resources. Using the International Protein Index database Applicant determined that of the 230 identities 68 were unique and present in at least one out of 3 gels. Applicant concentrated on the 20 identities found common in 2 out of 3 gels.
Figure 8:
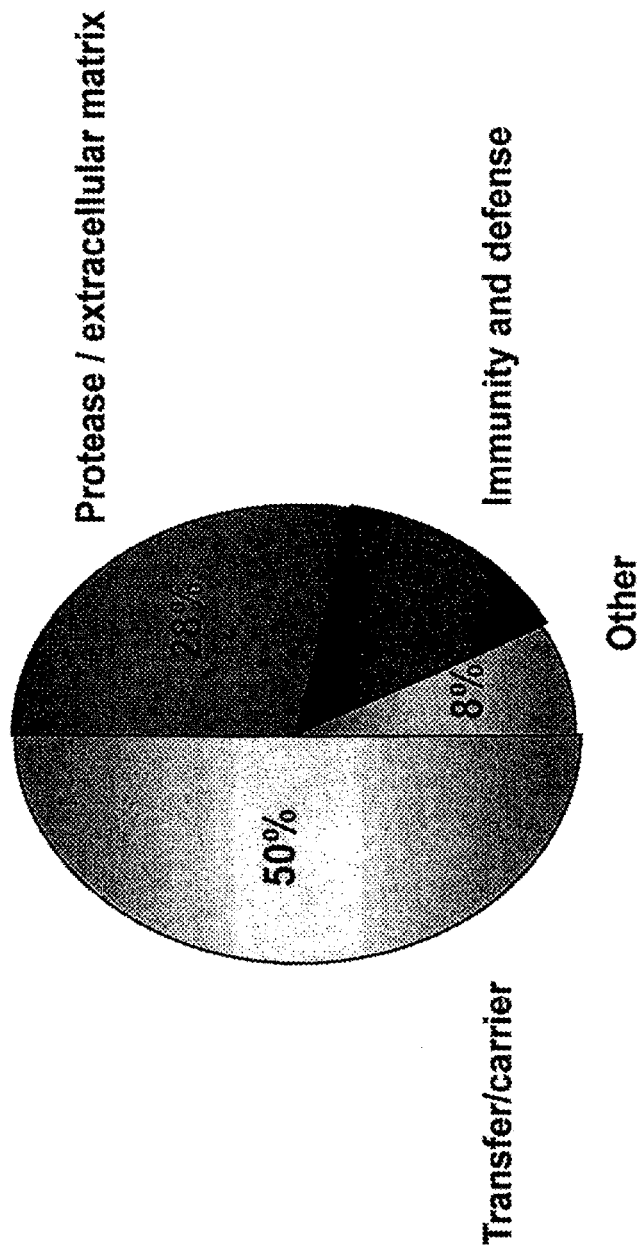
FIG. 8 is a representation of the ontological classification of these 20 common identities, which showed that transfer/carrier, proteases/extracellular matrix and immunity and defense were the molecular functions and biological processes most affected in neonates with early onset sepsis.
Figure 10:
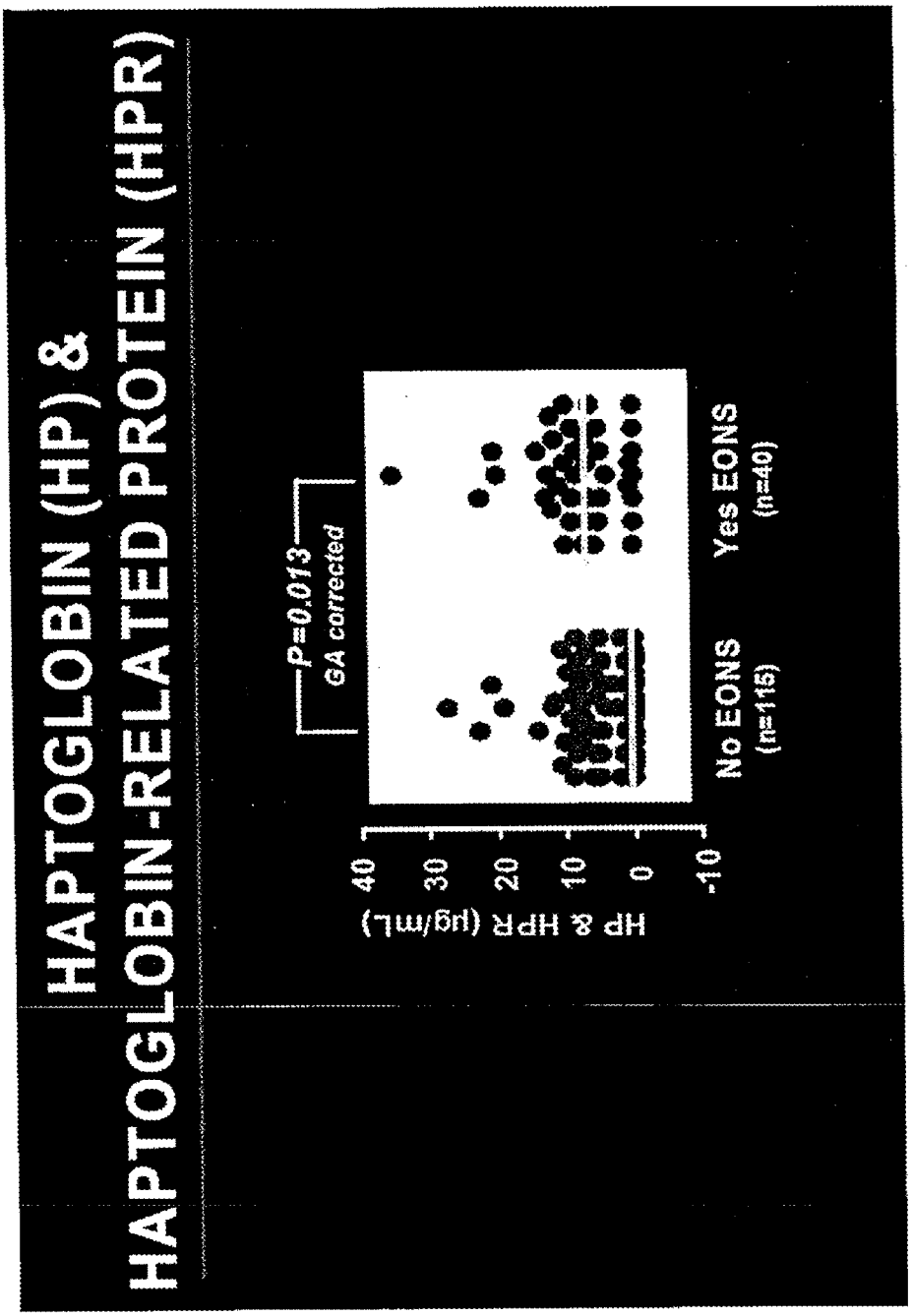
FIG. 10 shows results of assessment of Hp and HpRP (EONS, no EONS). These differences remained significant following correction for gestational age at delivery.
Figure 11:
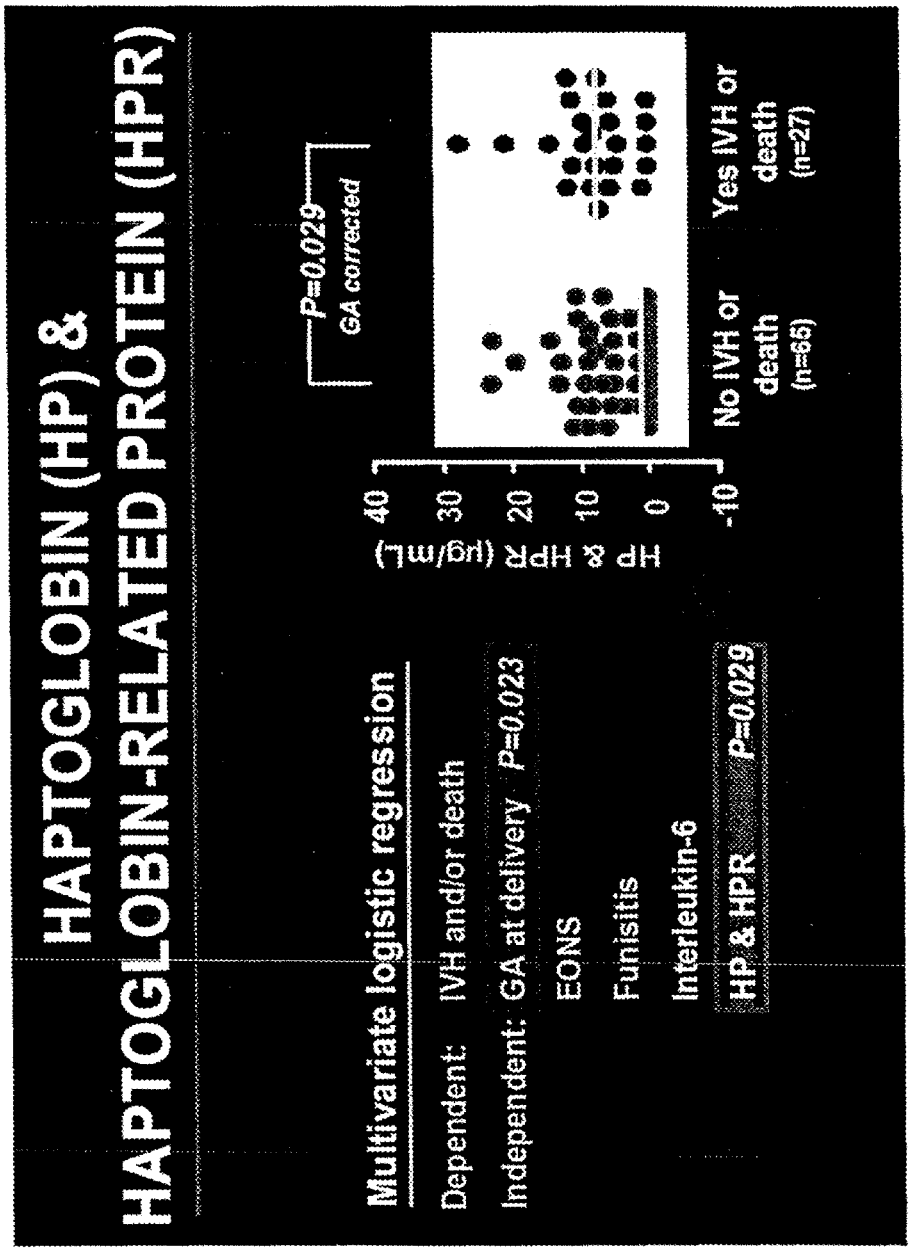
FIG. 11 shows results of an assessment of relevance of haptoglobin or haptoglobin-related proteins for neonatal outcomes other than early onset sepsis. Multivariate logistic regression analysis showed that gestational age at delivery and haptoglobin are independent predictors of intra-ventricular hemorrhage or death. Neonates who were to develop IVH or die had significantly higher haptoglobin levels at birth even after correction for gestational age.
Figure 12:
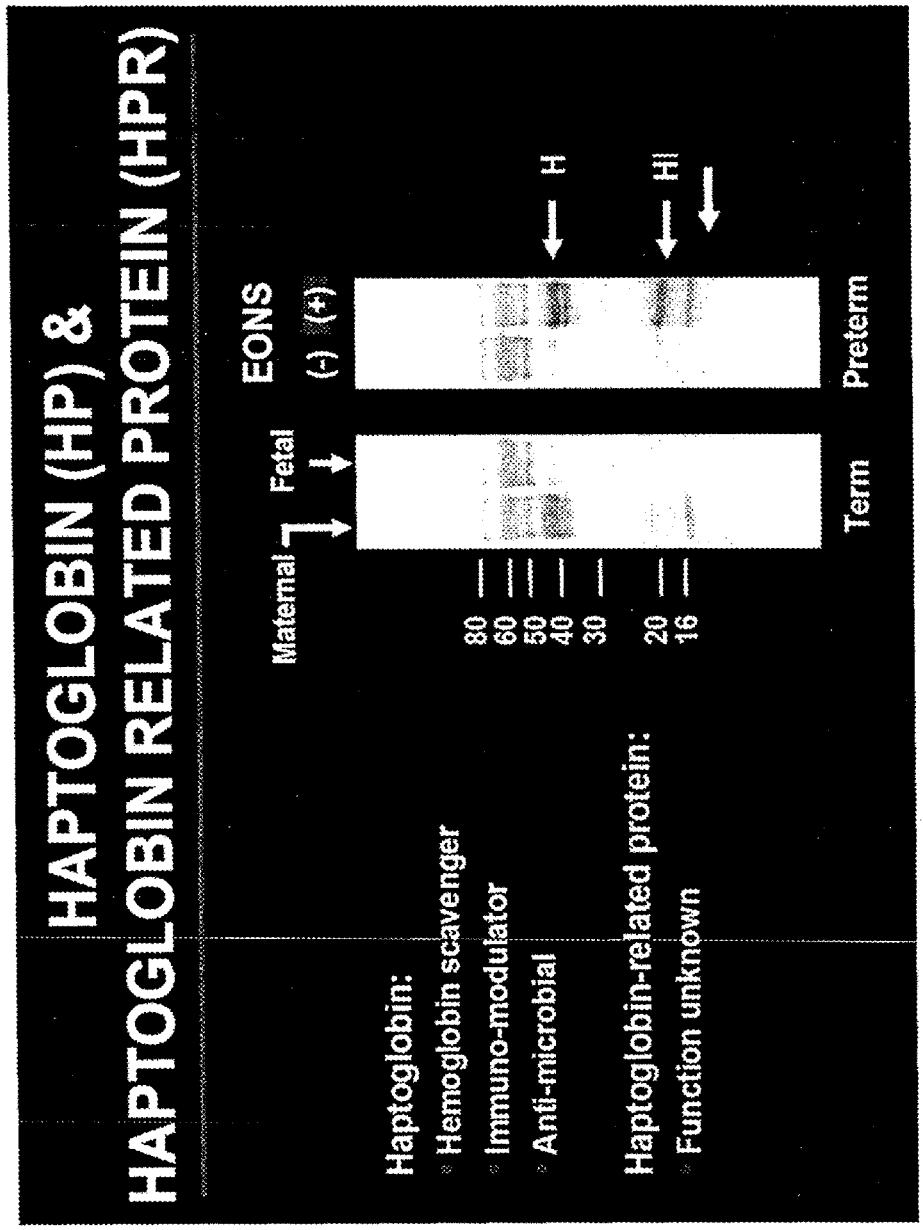
FIG. 12 shows results of Applicant's study of haptoglobin in the adult and fetus. Previous studies showed that haptoglobin is absent in the normal term fetus, as shown on the left of this Western blot. Applicant demonstrated that switching of haptoglobin and haptoglobin related protein expression toward an adult phenotype occurs prior to birth in infants with early onset neonatal sepsis, as shown on the right.

Supplemental Results a) Clinical and laboratory characteristics of the mothers and newborns who provided cord blood used during the 1$^{st}$-level validation are included in Table S2, and Table S3, respectively. Mothers of neonates with EONS were of lower GA at enrollment (amniocentesis), had shorter amniocentesis-to-delivery intervals, and delivered at earlier GAs newborns with lower birthweights and lower Apgar scores. GA at delivery is an important determinant of neonatal maturity and outcome. Following correction for GA at birth we determined that EONS impacted independently on the 1-minute Apgar score. Women who delivered neonates with EONS more often had amniotic fluid biochemical and microbiological tests results consistent with IAI. There was a higher frequency of histological chorioamnionitis and funisitis in the EONS group. Neonatal hematological tests and indices that were affected by EONS independent of GA were: neonatal WBC, neutrophil and lymphocyte counts, ABC and I:T ratio. Upon admission to NBSCU; 41 newborns were diagnosed with "presumed" EONS and placed promptly on i.v. antibiotics. In only 3 of these blood cultures returned a positive result. Blood cultures tested positive in another 4 newborns that did not show evidence of "presumed" EONS at admission. Thus, a total of 45 newborns from the 1$^{st}$-level validation cohort had clinical diagnosis of EONS. Together, these results point to the relevance of this cohort for validation of CB biomarkers resulting from antenatal encounters with etiological agents of intra-amniotic infection, inflammation and EONS.

b) Considerations for determination of cord blood Hp&HpRP immunoreactivity. Western blotting under denaturing and reduced conditions was far superior for detecting expressed Hp&HpRP patterns in cord blood compared to the peroxidase method [101] which appeared suitable only for adult blood (data not shown). Free hemoglobin present in coagulated samples is known to alter immunonephelometric measurements. The denaturing and reducing conditions of our Western blots were chosen to minimize such types of interference. The ELISA used was also specifically optimized for cord blood. Use of milk as both sample diluent and blocking buffer was critical to prevent non-specific binding. Moreover, the ELISA was ~3 orders of magnitude more sensitive than the immunonephelometric method used clinically in adults and employed by earlier studies that discarded Hp as marker of newborn sepsis. By using immunonephelometry as detection method for Hp, Kalayci et al. used a neonatal blood level cut-off of 250 μg/mL as indicator of sepsis [102]. This cut-off is ~75-fold higher compared to our optimal ELISA cut-off indicative of the Hp switch-on pattern (3.37 μg/mL). The highest cord blood Hp&HpRP immunoreactivity measured in our cohort was only ~35 μg/mL, with a median of only 9 μg/mL in the EONS group. Although lower than what is measured in adult blood, cord blood concentration of Hp&HpRP is relatively high and it can be used as a biomarker (>80-fold the IL-6 level in the same group). To summarize, during the validation phase Applicant opted for a different laboratory technique (sensitive ELISA+Western blot) to detect and quantify the levels of cord blood Hp. This is in contrast to other previous studies and is a possible explanation for the observation that Hp&HpRP is a useful biomarker for EONS. FIG. 5A illustrates differences in optical density (OD) readings obtained with standard curves prepared with Hp purified from adult blood of different phenotypes: Hp1-1, 1-2 and 2-2. The same concentration of Hp1-1 measured less in ELISA compared to Hp1-2 and to Hp2-2 which rendered the highest values. This data suggests that different Hp phenotypes impact on Hp&HpRP ELISA levels, and argues that reliance on immunoreactivity level alone remains simplistic.

There was a significant direct correlation between the total optical density of Hp&HpRP immunoreactivity by Western blot and by ELISA (R=0.863, P<0.001, FIG. 5B). A Hp&HpRP immunoreactivity >3,370 ng/mL in ELISA was best in indicating a switched-on Hp pattern in our preterm newborns (ROC area: 0.998, 95% CI [93.5-100], FIG. 5C). This indicates that a binary indicator derived from ELISA immunoreactivity can potentially be used in lieu of Western blotting for determination of the Hp switch pattern. However, until isoform-specific antibodies are available, Western blotting remains an accessible method for concurrent determination of the phenotype.

c) Latent-class analysis (LCA) to identify the probability of "antenatal IAI exposure". Chosen indicator variables were the cord blood Hp&HpRP switch pattern, IL-6 level and presumed EONS. Covariates were neonatal race, gender, Hp phenotype, GA at birth and membrane status. In our analysis LCA derived 4 models. In Table 7 shows the goodness of fit results for the 4 models used. A decrease in the values of the Bayesian Information Criterion (BIC) indicates an improvement in the fit, with increasing the number of clusters. Generally models with P>0.05 provides an adequate fit (no significant difference between the model and the data). The model with the fewest number of parameters (most parsimonious) should be selected. Based on these criteria, Model 2 (2-cluster solution) appeared the best fit of our data. We next compared Model 2 with Model 3 using bootstrap statistical procedures. This analysis indicated that the improvement in classification rendered by Model 3 did not reach statistical significance (−2LL difference: 23, P=0.07). Thus, Model 2 was chosen as the best fit for the data.

To understand the type of clinical scenarios that were allocated to the clusters Applicant explored: 1) how the 3 indicators (Hp&HpRP switch pattern, cord blood IL-6≥100 pg/mL, EONS) participated at clustering of the data and 2) whether any of the covariates (Hp phenotype, gender, GA, membrane status) showed statistical significance. Table 8 displays the contribution of the indicator variables at discriminating the two latent clusters along with information on covariates. Although the covariates were not set to drive the clustering, their significant difference would bring more information about the characteristics of the cases composing each cluster (i.e. earlier GA, racial characteristics, etc). In the LCA model used, most of the input was achieved from Hp switching (GK-θ: 0.98). The least input was obtained from presumed EONS (GK-θ: 0.14). Of the covariates, only Hp phenotype showed statistical disparity between the two clusters (P=0.002). FIG. 6 displays a practical algorithm (data showed in a flowchart format) related to distribution of the cases to either cluster-1 (likely non-exposed) or cluster-2 (likely exposed). Most of the input for the algorithm is derived from two cord blood indicators (Hp switch pattern and IL-6≥100 ng/mL). A diagnosis of presumed EONS aids with adjusting the probability for cluster assignment, but its contribution to the clustering is minor compared to the two aforementioned indicators.

REFERENCES FOR PAGES 1-57

1. Bryce J, Boschi-Pinto C, Shibuya K, et al. WHO Child Health Epidemiology Reference Group. WHO estimates of the causes of death in children. Lancet 2005; 365: 1147-52.

2. Hamilton B E et al. Births: Preliminary Data for 2007. Natl Vital Stat Rep 2009; 57 (12):1-23 (accessed May 23, 2009).
3. Stoll B J, Hansen N I, Adams-Chapman I, et al. Neurodevelopmental and growth impairment among extremely low-birth-weight infants with neonatal infection. JAMA 2004; 292: 2357-65.
4. Slattery M M, Morrison J J. Preterm delivery. Lancet. 2002; 360:1489-97.
5. Retrieved on Sep. 14, 2008. http://www.marchofdimes.com/prematurity/21198_10734.asp.
6. Kenyon S L, Pike K, Jones D R, Brocklehurst P, Marlow N, Salt A, Taylor D J. Childhood outcomes after prescription of antibiotics to pregnant women with preterm rupture of the membranes: 7-year follow-up of the ORACLE I trial. Lancet 2008; doi: 10.1016/s0140-6736 (08) 61202-7.
7. Kenyon S L, Pike K, Jones D R, Brocklehurst P, Marlow N, Salt A, Taylor D J. Childhood outcomes after prescription of antibiotics to pregnant women with spontaneous preterm labour: 7-year follow-up of the ORACLE II trial. Lancet 2008; doi: 10.1016/s0140-6736 (08) 61203-9.
8. Green N S, Damus K, Simpson J L et al. March of Dimes Scientific Advisory Committee on Prematurity. Research agenda for preterm birth: recommendations from the March of Dimes. Am J Obstet Gynecol. 2005; 193, 626-635.
9. Institute of Medicine of the National Academies. Preterm Birth. Causes, Consequences, and Prevention. Eds: Behrman R E, Butler A S. The National Academies Press, Washington D.C. (2007).
10. Sinclair K D, Allegrucci C, Singh R, Gardner D S, Sebastian S, Bispham J, Thurston A, Huntley J F, Rees W D, Maloney C A, Lea R G, Craigon J, McEvoy T G, Young L E. DNA methylation, insulin resistance, and blood pressure in offspring determined by maternal periconceptional B vitamin and methionine status. Proc Natl Acad Sci USA. 2007; 104 (49):19351-6.
11. Tita A T, Rouse D J. Progesterone for preterm birth prevention: an evolving intervention. Am J Obstet Gynecol 2009; 200: 219-24.
12. Denney J M, Culhane J F, Goldenberg R L. Prevention of preterm birth. Womens Health (Lond Engl) 2008; 4: 625-38.
13. Lockwood C J, Kuczynski E. Markers of risk for preterm delivery. J Perinat Med. 27, 5-20 (1999).
14. Draper E S, Manktelow B, Field D J, James D. Prediction of survival for preterm births by weight and gestational age: retrospective population based study. BMJ 1999; 319: 1093-7.
15. Grigg J, Arnon S, Chase A, Silverman M. Inflammatory cells in the lungs of premature infants on the first day of life. Perinatal risk factors and origin of cells. Arch Dis Child 1993; 69: 40-3.
16. Bizzarro M J, Raskind C, Baltimore R S, Gallagher P G. Seventy-five years of neonatal sepsis at Yale: 1928-2003. Pediatrics 2005; 116: 595-602.
17. Buhimschi C S, Bhandari V, Han Y W, Dulay A T, Baumbusch M A, Madri J A, Buhimschi I A. Using proteomics in perinatal and neonatal sepsis: hopes and challenges for the future. Curr Opin Infect Dis 2009; 22 (3):235-43.
18. Steer P J. The epidemiology of preterm labour—why have advances not equated to reduced incidence? BJOG. 2006; 113 Suppl 3:1-3.
19. Larsen J W, Goldkrand J W, Hanson T M et al. Intrauterine infection on an obstetric service. Obstet Gynecol. 43, 838-843 (1974).
20. Buhimschi C S, Bhandari V, Hamar B D et al. Proteomic profiling of the AF to detect inflammation, infection, and neonatal sepsis. PLoS Med. 4, e18 (2007).
21. Klein L L, Gibbs R S. Infection and preterm birth. Obstet Gynecol Clin North Am. 32, 397-410 (2005).
22. Goldenberg R L, Culhane J F, Johnson D C. Maternal infection and adverse fetal and neonatal outcomes. Clin Perinatol. 2005; 32: 523-59.
23. Buhimschi I A, Zhao G, Rosenberg V A, Thung S, Buhimschi C S. Multidimensional proteomics analysis of AF to provide insight into the mechanisms of idiopathic preterm birth. PLoS ONE. 2008; 3: e2049.
24. Klein L L, Gibbs R S. Infection and preterm birth. Obstet Gynecol Clin North Am. 2005; 32: 397-410.
25. Bizzarro M J, Dembry L M, Baltimore R S, et al. Changing patterns in neonatal *Escherichia coli* sepsis and ampicillin resistance in the era of intrapartum antibiotic prophylaxis. Pediatrics 2008; 121: 689-696.
26. Larsen J W, Sever J L. Group B *Streptococcus* and pregnancy: a review. Am J Obstet Gynecol 2008; 198: 440-8.
27. Pettker C M, Buhimschi I A, Magloire L K, Sfakianaki A K, Hamar B D, Buhimschi C S. Value of placental microbial evaluation in diagnosing intra-amniotic infection. Obstet Gynecol. 2007; 109: 739-49.
28. Barron, E L Jorgensen, J H, Landry, M L, et al. 2007. Bacteriology. P 974. In Murray P R (ed). Manual of clinical Bacteriology, 9th ed, ASM Press, Washington, D.C.
29. Dong J, Olano J P, McBride J W, et al. Emerging pathogens: challenges and successes of molecular diagnostics. J Mol Diagn. 2008; 10:185-197.
30. Kuypers M M. Microbiology. Sizing up the uncultivated majority. Science 2007; 317:1510-1.
31. Hitti J, Riley D E, Krohn M A, Hillier S L, Agnew K J, Krieger J N, Eschenbach D A. Broad-spectrum bacterial rDNA polymerase chain reaction assay for detecting AF infection among women in premature labor. Clin Infect Dis 1997; 24:1228-32.
32. Markenson G, Martin R, Tillotson-Criss M, Foley K S, Stewart R S Jr, Yancey M. The use of polymerase chain reaction to detect bacteria in A F in pregnancies complicated with preterm labor. Am J Obstet Gynecol. 1997; 177; 1471-7.
33. Han Y W, Zhang L, Chung P, Kirchner L, Buhimschi I A, Buhimschi C S Evidence of uncultivated bacteria as etiologic agents of intra-amniotic infection and inflammation leading to preterm birth. Am J Obstet Gynecol 2007; 197: S66.
34. Han Y W, Shen T, Chung P, Buhimschi I A, Buhimschi C S. Uncultivable bacteria as etiologic agents of intra-amniotic inflammation leading to preterm birth. J Clin Microbiol 2009; 47: 38-47.
35. Goldenberg R L, Hauth J C, Andrews W W. Intrauterine infection and preterm delivery. N Engl J Med. 342, 1500-1507 (2000).
36. Andrews W W, Goldenberg R L, Hauth J C. Preterm labor: emerging role of genital tract infections. Infect Agents Dis. 4, 196-211 (1995).
37. Ng P C, Lam H S. Diagnostic markers for neonatal sepsis. Curr Opin Pediatr 2006; 18: 125-31.
38. Smulian J C, Bhandari V, Campbell W A, Rodis J F, Vintzileos A M. Value of umbilical artery and vein levels of interleukin-6 and soluble intracellular adhesion molecule-1 as predictors of neonatal hematologic indices and suspected early sepsis. J Matern Fetal Med 1997; 6: 254-9.

39. Gonzalez B E, Mercado C K, Johnson L, Brodsky N L, Bhandari V. Early markers of late-onset sepsis in premature neonates: clinical, hematological and cytokine profile. Perinat Med 2003; 31:60-8.
40. Cotten C M, Taylor S, Stoll B, Goldberg R N, Hansen N I, Sanchez P J, Ambalavanan N, Benjamin D K Jr; NICHD Neonatal Research Network. Prolonged duration of initial empirical antibiotic treatment is associated with increased rates of necrotizing enterocolitis and death for extremely low birth weight infants. Pediatrics 2009; 123: 58-66.
41. Kalenic S, Francetic I, Polak J, Zele-Starcevic L, Bencic Z. Impact of ampicillin and cefuroxime on bacterial colonization and infection in patients on a neonatal intensive care unit. The Journal of Hospital Infection 1993; 23: 35-41.
42. Buhimschi C S, Dulay A T, Abdel-Razeq S, Zhao G, Lee S, Hodgson E J, Bhandari V, Buhimschi I A. Fetal inflammatory response in women with proteomic biomarkers characteristic of intra-amniotic inflammation and preterm birth. BJOG 2009 116: 257-67.
43. Buttery J P. Blood cultures in newborns and children: optimising an everyday test. Arch Dis Child Fetal Neonatal Ed. 2002; 87: F25-28.
44 Miller M E. Host defenses in the human neonate. Pediatric Clinics of North America 1977; 24:413-23.
45. Goldenberg R L, Andrews W W, Goepfert A R, et al. The Alabama Preterm Birth Study: umbilical CB *Ureaplasma urealyticum* and *Mycoplasma hominis* cultures in very preterm newborn infants. Am J Obstet Gynecol. 2008; 198: e1-5.
46. Jordan J A, Durso M B, Butchko A R, Jones J G, Brozanski B S. Evaluating the near-term infant for early onset sepsis: progress and challenges to consider with 16S rDNA polymerase chain reaction testing. J Mol Diagn. 2006; 8: 357-363.
47. Rodwell R L, Taylor K M, Tudehope D I, Gray P H. Hematologic scoring system in early diagnosis of sepsis in neutropenic newborns. Pediatr Infect Dis J. 1993; 12: 372-376.
48. Bhandari V, Wang C, Rinder C, Rinder C, Rinder H. Hematologic profile of sepsis in neonates: neutrophil CD64 as a diagnostic marker. Pediatrics 2008; 121:129-134.
49. Buhimschi C S, Bhandari V, Hamar B D et al. Proteomic profiling of the amniotic fluid to detect inflammation, infection, and neonatal sepsis. PLoS Med. 4, e18 (2007).
50. Buhimschi I A, Buhimschi C S, Weiner C P, Kimura T, Hamar B D, Sfakianaki A K, Norwitz E R, Funai E F, Ratner E. Proteomic but not enzyme-linked immunosorbent assay technology detects amniotic fluid monomeric calgranulins from their complexed calprotectin form. Clin Diagn Lab Immunol 2005; 12: 837-44.
51. Buhimschi I A, Buhimschi C S, Christner R, Weiner C P. Proteomics technology for the accurate diagnosis of inflammation in twin pregnancies. BJOG 2005; 112: 250-5.
52. Buhimschi C S, Pettker C M, Magloire L K, Martin R, Norwitz E, Funai E, Buhimschi I A. Proteomic technology and delayed interval delivery in multiple pregnancies. Int J Gynaecol Obstet 2005; 90: 48-50.
53. Buhimschi C S, Weiner C P, Buhimschi I A. Clinical proteomics Part II. The emerging role of proteomics over genomics in spontaneous preterm labor/birth. Obstet Gynecol Surv 2006; 61: 543-53.
54. Buhimschi I A, Buhimschi C S. Proteomics of the amniotic fluid in assessment of the placenta. Relevance for preterm birth. Placenta 2008; 29: S95-101.
55 Holzheimer R G. Antibiotic induced endotoxin release and clinical sepsis: a review. J. Chemother. 2001 November; 13 Spec No 1 (1):159-72. Review.
56. Freedman R M, Ingram D I, Gross I, Ehrenkranz R A, Warshaw J B, Baltimore R S. A half century of neonatal sepsis at Yale: 1928 to 1978. American Journal of Diseases of Children 1981; 135:140-4.
57. Yurdakök M. Antibiotic use in neonatal sepsis. Turk J Pediatr 1998; 40:17-33.
58. Mtitimila E I, Cooke R W. Antibiotic regimens for suspected early neonatal sepsis. Cochrane Database Syst Rev 2004:CD004495.
59. Spitzer A R, Kirkby S, Kornhauser M. Practice variation in suspected neonatal sepsis: a costly problem in neonatal intensive care. J Perinatol 2005 25: 265-9.
60. Dobryszycka W. Biological functions of haptoglobin—new pieces to an old puzzle. Eur J Clin Chem Clin Biochem 1997; 35:647-54.
61. Jue D M, Shim B S, Kang Y S. Inhibition of prostaglandin synthase activity of sheep seminal vesicular gland by human serum haptoglobin. Mol Cell Biochem. 1983; 51 (2):141-7.
62. Oh S K, Very D L, Walker J, Raam S, Ju S T. An analogy between fetal haptoglobin and a potent immunosuppressant in cancer. Cancer Res. 1987; 47: 5120-6.
63. Oh S K, Pavlotsky N, Tauber A L Specific binding of haptoglobin to human neutrophils and its functional consequences. J Leukoc Biol. 1990 February; 47 (2):142-8.
64 Haptoglobin: a natural bacteriostat. Eaton J W, Brandt P, Mahoney J R, Lee J T Jr. Science. 1982 Feb. 5; 215 (4533): 691-3.
65. Berkova N, Lemay A, Dresser D W, Fontaine J Y, Kerizit J, Goupil S. Haptoglobin is present in human endometrium and shows elevated levels in the decidua during pregnancy. Mol Hum Reprod. 2001; 7:747-54.
66. Smithies O, Connell G E, Dixon G H. Nature. 1962 Oct. 20; 196:232-6. Chromosomal rearrangements and the evolution of haptoglobin genes.
67. Maeda N, Smithies O. The evolution of multigene families: human haptoglobin genes. Annu Rev Genet. 1986; 20:81-108.
68. Cox S E, Doherty C, Atkinson S H, Nweneka C V, Fulford A J, Ghattas H, Rockett K A, Kwiatkowski D P, Prentice A M. Haplotype association between haptoglobin (Hp2) and Hp promoter SNP (A-61C) may explain previous controversy of haptoglobin and malaria protection. PLoS ONE. 2007 Apr. 11; 2 (4):e362.
69. Tseng C F, Lin C C, Huang H Y, Liu H C, Mao S J. Antioxidant role of human haptoglobin. Proteomics. 2004 August; 4 (8):2221-8.
70. Asleh R, Levy A P. In vivo and in vitro studies establishing haptoglobin as a major susceptibility gene for diabetic vascular disease. Vasc Health Risk Manag. 2005; 1 (1):19-28.
71 Quaye I K. Haptoglobin, inflammation and disease. Trans R Soc Trop Med Hyg. 2008 August; 102 (8):735-42. Epub 2008 May 16.
72. Melamed-Frank M, Lache O, Enav B I, Szafranek T, Levy N S, Ricklis R M, Levy A P. Structure-function analysis of the antioxidant properties of haptoglobin. Blood. 2001 Dec. 15; 98 (13):3693-8. Blood. 2001 Dec. 15; 98 (13): 3693-8.
73. Sinclair K D, Allegrucci C, Singh R, Gardner D S, Sebastian S, Bispham J, Thurston A, Huntley J F, Rees W D, Maloney C A, Lea R G, Craigon J, McEvoy T G, Young L E. DNA methylation, insulin resistance, and blood pressure in offspring determined by maternal periconceptional B vitamin and methionine status. Proc Natl Acad Sci USA. 2007; 104 (49):19351-6.
74. Bueler M R, Bersinger N A. Antiserum to pregnancy-associated plasma protein A (PAPP-A) recognizes human haptoglobin. Br J Obstet Gynaecol. 1989 July; 96 (7):867-9.
75 Smith A B, Esko J D, Hajduk S L. Killing of trypanosomes by the human haptoglobin-related protein. Science. 1995 Apr. 14; 268 (5208):284-6.
76. Michael L Bishop; Edward P Fody; Larry E Schoeff Clinical chemistry: principles, procedures, correlations Philadelphia: Lippincott Williams & Wilkins, ©2005.
77. Tang D, Kang R, Xiao W, Zhang H, Lotze M T, Wang H, Xiao X: Quercetin prevents lipopolysaccharide-induced HMGB1 release and proinflammatory function. Am J Respir Cell Mol. Biol. 2009 (Epub ahead of print)
78. Yang H, Ochani M, Li J, Tanovic M, Harris H E, Susarla S M, Ulloa L, Wang H, DiRaimo R, Czura C J, Wang H, Roth J, Warren H S, Fink M P, Fenton M J, Andersson U, Tracey K J: Reversing established sepsis with antagonists of endogenous high-mobility group box 1. Proc Natl Acad Sci USA. 2004; 101:296-301.
79. Zhang H, Tasaka S, Shiraishi Y, Fukunaga K, Yamada W, Seki H, Ogawa Y, Miyamoto K, Nakano Y, Hasegawa N, Miyasho T, Maruyama I, Ishizaka A: Role of soluble receptor for advanced glycation end products on endotoxin-induced lung injury. Am J Respir Crit Care Med. 2008; 178:356-362.
80. Lutterloh E C, Opal S M, Pittman D D, Keith J C Jr, Tan X Y, Clancy B M, Palmer H, Milarski K, Sun Y, Palardy J E, Parejo N A, Kessimian N: Inhibition of the RAGE products increases survival in experimental models of severe sepsis and systemic infection. Crit Care 2007; 11:R122.
81. Ekong U, Zeng S, Dun H, Feirt N, Guo J, Ippagunta N, Guarrera J V, Lu Y, Weinberg A, Qu W, Ramasamy R, Schmidt A M, Emond J C: Blockade of the receptor for advanced glycation end products attenuates acetaminophen-induced hepatotoxicity in mice. J Gastroenterol Hepatol. 2006; 21:682-688.
82. Zeng S, Feirt N, Goldstein M, Guarrera J, Ippagunta N, Ekong U, Dun H, Lu Y, Qu W, Schmidt A M, Emond J C: Blockade of receptor for advanced glycation end product (RAGE) attenuates ischemia and reperfusion injury to the liver in mice. Hepatology. 2004; 39:422-432.
83. Stern D, Yan S D, Yan S F, Schmidt A M: Receptor for advanced glycation endproducts: a multiligand receptor magnifying cell stress in diverse pathologic settings. Adv Drug Deliv Rev 2002; 54:1615-1625.
84. Muhammad S, Barakat W, Stoyanov S, Murikinati S, Yang H, Tracey K J, Bendszus M, Rossetti G, Nawroth P P, Bierhaus A, Schwaninger M: The HMGB1 receptor RAGE mediates ischemic brain damage. J Neurosci. 2008; 28:12023-12031.
85. Speer C H, Bruns A, Gahr M. Sequential determination of CRP, alpha 1-antitrypsin and haptoglobin in neonatal septicaemia. Acta Paediatr Scand 72: 679-83, 1983.
86. Ayhan Gazi KALAYCI1, Fazh YILMAZER1, Bahattin ADAM2, Recep SANCAK1, Sükrü KÜçÜKÖDÜK1 The Importance of Fibronectin, Haptoglobin, Ceruloplasmin and Transferrin in the Early Diagnosis of Neonatal Sepsis Turk J Med Sci 30 (2000) 151-155

REFERENCES FOR EXAMPLE 6

1. Robertson C M, Watt M J, Yasui Y. Changes in the prevalence of cerebral palsy for children born very prematurely within a population-based program over 30 years. JAMA. 2007 297 (24):2733-40.
2. Buhimschi C S, Bhandari V, Hamar B D, Bahtiyar M O, Zhao G, Sfakianaki A K, Pettker C M, Magloire L, Funai E, Norwitz E R, Paidas M, Copel J A, Weiner C P, Lockwood C J, Buhimschi I A. Proteomic profiling of the amniotic fluid to detect inflammation, infection, and neonatal sepsis. PLoS Med. 2007; 4:e18.
3. Tita A T, Andrews W W. Diagnosis and management of clinical chorioamnionitis. Clin Perinatol. 2010; 37:339-54.
4. Klinger G, Levy I, Sirota L, Boyko V, Lerner-Geva L, Reichman B; in collaboration with the Israel Neonatal Network. Outcome of early-onset sepsis in a national cohort of very low birth weight infants. Pediatrics. 2010; 125:e736-40.
5. Hintz S R, Kendrick D E, Wilson-Costello D E, Das A, Bell E F, Vohr B R, Higgins R D; NICHD Neonatal Research Network. Early-childhood neurodevelopmental outcomes are not improving for infants born at <25 weeks' gestational age. Pediatrics 2011; 127:62-70.
6. Kolialexi A, Mavrou A, Spyrou G, Tsangaris G T. Mass spectrometry-based proteomics in reproductive medicine. Mass Spectrom Rev. 2008; 27:624-34.
7. Buhimschi C S, Bhandari V, Han Y W, Dulay A T, Baumbusch M A, Madri J A, Buhimschi I A. Using proteomics in perinatal and neonatal sepsis: hopes and challenges for the future. Curr Opin Infect Dis. 2009; 22:235-43.
8. Amon S, Litmanovitz I. Diagnostic tests in neonatal sepsis. Curr Opin Infect Dis. 2008; 21:223-7. Buhimschi et al. -25
9. Ng P C, Ang I L, Chiu R W, Li K, Lam H S, Wong R P, Chui K M, Cheung H M, Ng E W, Fok T F, Sung J J, Lo Y M, Poon T C. Host-response biomarkers for diagnosis of late-onset septicemia and necrotizing enterocolitis in preterm infants. J Clin Invest. 2010; 120:2989-3000.
10. Buhimschi I A, Buhimschi C S. The role of proteomics in the diagnosis of chorioamnionitis and early-onset neonatal sepsis. Clin Perinatol. 2010; 37:355-74.
11. Buhimschi I A, Christner R, Buhimschi C S. Proteomic biomarker analysis of amniotic fluid for identification of intra-amniotic inflammation. BJOG. 2005; 112:173-81.
12. Hadlock F P, Deter R L, Harrist R B, Park S K. Computer assisted analysis of fetal age in the third trimester using multiple fetal growth parameters. J Clin Ultrasound 1983; 11:313-6.
13. ACOG Committee on Practice Bulletins-Obstetrics. ACOG Practice Bulletin No. 80: premature rupture of membranes. Clinical management guidelines for obstetrician-gynecologists. Obstet Gynecol 2007; 109:1007-19.
14. Naef R W 3rd, Allbert J R, Ross E L, Weber B M, Martin R W, Morrison J C. Premature rupture of membranes at 34 to 37 weeks' gestation: aggressive versus conservative management. Am J Obstet Gynecol. 1998; 178:126-130.
15. Edwards R K, Clark P, Locksmith Gregory J, Duff P. Performance characteristics of putative tests for subclinical chorioamnionitis. Infect Dis Obstet Gynecol 2001; 9:209-214.
16. Garry D, Figueroa R, Aguero-Rosenfeld M, Martinez E, Visintainer P, Tejani N. A comparison of rapid amniotic fluid markers in the prediction of microbial invasion of the uterine cavity and preterm delivery Am J Obstet Gynecol 1996; 175:1336-1341.
17. Naeye R L. Disorders of the placenta and decidua. (1992) In: Disorder of the Placenta, Fetus and Neonate: Diagnosis and Clinical Significance. St. Louis: Mosby, pp. 118-247. Buhimschi et al. -26
18. Salafia C M, Weigl C, Silberman L. The prevalence and distribution of acute placental inflammation in uncomplicated term pregnancies. Obstet Gynecol 1989; 73: 383-389.

19. Rodwell R L, Taylor K M, Tudehope D I, Gray P H. Hematologic scoring system in early diagnosis of sepsis in neutropenic newborns. Pediatr Infect Dis J 1993; 12:372-376.
20. McCrea H J, Ment L R. The diagnosis, management, and postnatal prevention of intraventricular hemorrhage in the preterm neonate. Clin Perinatol 2008; 35:777-92.
21. An international classification of retinopathy of prematurity. The Committee for the Classification of Retinopathy of Prematurity. Arch Ophthalmol 1984; 102:1130-1134.
22. Uauy R D, Fanaroff A A, Korones S B, Phillips E A, Phillips J B, Wright L L. Necrotizing enterocolitis in very low birth weight infants: biodemographic and clinical correlates. National Institute of Child Health and Human Development Neonatal Research Network. J Pediatr 1991; 119:630-8.
23. Bhandari A, Bhandari V. Bronchopulmonary dysplasia: an update. Indian J Pediatr 2007; 74:73-7.
24. Buhimschi C S, Dulay A T, Abdel-Razeq S, Zhao G, Lee S, Hodgson E J, Bhandari V, Buhimschi I A. Fetal inflammatory response in women with proteomic biomarkers characteristic of intra-amniotic inflammation and preterm birth. BJOG 2009 116: 257-67.
25. Ramström M, Hagman C, Mitchell J K, Derrick P J, Håkansson P, Bergquist J. Depletion of high-abundant proteins in body fluids prior to liquid chromatography fourier transform ion cyclotron resonance mass spectrometry. J Proteome Res 2005; 4:410-6.
26. Shifman M A, Li Y, Colangelo C M, Stone K L, Wu T L, Cheung K H, Miller P L, Williams K R. YPED: a web-accessible database system for protein expression analysis. J Proteome Res 2007; 6:4019-24. Buhimschi et al. -27
27. Kersey P J, Duarte J, Williams A, Karavidopoulou Y, Birney E, Apweiler R. The International Protein Index: an integrated database for proteomics experiments. Proteomics 2004; 4:1985-8.
28. Maeda N, Smithies O. The evolution of multigene families: human haptoglobin genes. Annu Rev Gene 1986; 20:81-108.
29. Hatada S, Grant D J, Maeda N. An intronic endogenous retrovirus-like sequence attenuates human haptoglobin-related gene expression in an orientation-dependent manner. Gene 2003; 319:55-63.
30. Bensi G, Raugei G, Klefenz H, Cortese R. Structure and expression of the human haptoglobin locus. EMBO J 1985; 4:119-26.
31. Dobryszycka W. Biological functions of haptoglobin—new pieces to an old puzzle. Eur J Clin Chem Clin Biochem 1997; 35:647-54.
32. Smithies O, Connell G E, Dixon G H. Chromosomal rearrangements and the evolution of haptoglobin genes. Nature 1962; 196:232-6.
33. Maeda N. The evolution of multigene families: human haptoglobin genes. Annu Rev Genet. 1986; 20:81-108.
34. Vermunt J K, Magidson J: Latent class cluster analysis. In Applied latent class analysis. Edited by Hagenaars J, McCutcheon A. Cambridge University Press; 2002:89-106
35. Huck S W. Reading statistics and research (3-rd edition). Addison Wessly Longman New York, 2000: 628-9.
36. Rausen A R, Gerald P S, Diamond L K. Haptoglobin patterns in CB serums. Nature 1961; 191:717. Buhimschi et al. -28
37. Michael L Bishop; Edward P Fody; Larry E Schoeff Clinical chemistry: principles, procedures, correlations Philadelphia: Lippincott Williams & Wilkins, 2005.
38 Oliviero S, Cortese R. The human haptoglobin gene promoter: interleukin-6-responsive elements interact with a DNA-binding protein induced by interleukin-6. EMBO J. 1989; 8:1145-51.
39. Gerdes J S. Diagnosis and management of bacterial infections in the neonate. Pediatr Clin North Am. 2004; 51:939-59.
40. Yurdakök M. Antibiotic use in neonatal sepsis. Turk J Pediatri 1998; 40:17-33.
41. Mtitimila E I, Cooke R W. Antibiotic regimens for suspected early neonatal sepsis. Cochrane Database Syst Rev 2004:CD004495.
42. Bizzarro M J, Dembry L M, Baltimore R S, Gallagher P G. Changing patterns in neonatal *Escherichia coli* sepsis and ampicillin resistance in the era of intrapartum antibiotic prophylaxis. Pediatrics. 2008; 121:689-96.
43. Cotten C M, Taylor S, Stoll B, Goldberg R N, Hansen N I, Sanchez P J, Ambalavanan N, Benjamin D K Jr; NICHD Neonatal Research Network. Prolonged duration of initial empirical antibiotic treatment is associated with increased rates of necrotizing enterocolitis and death for extremely low birth weight infants. Pediatrics 2009; 123: 58-66.
44. Kalenic S, Francetic I, Polak J, Zele-Starcevic L, Bencic Z. Impact of ampicillin and cefuroxime on bacterial colonization and infection in patients on a neonatal intensive care unit. The Journal of Hospital Infection 1993; 23: 35-41.
45. Goldenberg R L, Andrews W W, Goepfert A R, et al. The Alabama Preterm Birth Study: umbilical CB *Ureaplasma urealyticum* and *Mycoplasma hominis* cultures in very preterm newborn infants. Am J Obstet Gynecol. 2008; 198: e1-5. Buhimschi et al. -29
46. Gabay C, Kushner I. Acute-phase proteins and other systemic responses to inflammation. N Engl J Med. 1999; 340:448-54.
47. Rodwell R L, Leslie A L, Tudehope D I. Early diagnosis of neonatal sepsis using a hematologic scoring system. J. Pediatr. 1988; 112:761-7.
48. Santana Reyes C, García-Muñoz F, Reyes D, González G, Dominguez C, Domenech E. Role of cytokines (interleukin-1beta, 6, 8, tumour necrosis factor-alpha, and soluble receptor of interleukin-2) and C-reactive protein in the diagnosis of neonatal sepsis. Acta Paediatr. 2003; 92:221-7.
49. Bhandari V, Wang C, Rinder C, Rinder H. Hematologic profile of sepsis in neonates: neutrophil CD64 as a diagnostic marker. Pediatrics. 2008; 121:129-34.
50. Buttery J P. Blood cultures in newborns and children: optimising an everyday test. Arch Dis Child Fetal Neonatal Ed. 2002; 87: F25-28.
51 Miller M E. Host defenses in the human neonate. Pediatric Clinics of North America 1977; 24:413-23.
52. Han Y W, Shen T, Chung P, Buhimschi I A, Buhimschi C S. Uncultivable bacteria as etiologic agents of intra-amniotic inflammation leading to preterm birth. J Clin Microbiol 2009; 47: 38-47.
53 Buhimschi C S, Bhandari V, Hamar B D et al. Proteomic profiling of the AF to detect inflammation, infection, and neonatal sepsis. PLoS Med. 4, e18 (2007).
54. Han Y W, Zhang L, Chung P, Kirchner L, Buhimschi I A, Buhimschi C S Evidence of uncultivated bacteria as etiologic agents of intra-amniotic infection and inflammation leading to preterm birth. Am J Obstet Gynecol 2007; 197: S66.
55. Han Y W, Shen T, Chung P, Buhimschi I A, Buhimschi C S. Uncultivable bacteria as etiologic agents of intra-amniotic inflammation leading to preterm birth. J Clin Microbiol 2009; 47: 38-47. Buhimschi et al. -30
56. Dong J, Olano J P, McBride J W, et al. Emerging pathogens: challenges and successes of molecular diagnostics. J Mol Diagn. 2008; 10:185-197.
57. Kuypers M M. Microbiology. Sizing up the uncultivated majority. Science 2007; 317:1510-1.
58. Hitti J, Riley D E, Krohn M A, Hillier S L, Agnew K J, Krieger J N, Eschenbach D A. Broadspectrum bacterial rDNA polymerase chain reaction assay for detecting A F infection among women in premature labor. Clin Infect Dis 1997; 24:1228-32.
59. Markenson G, Martin R, Tillotson-Criss M, Foley K S, Stewart R S Jr, Yancey M. The use of polymerase chain reaction to detect bacteria in A F in pregnancies complicated with preterm labor. Am J Obstet Gynecol. 1997; 177; 1471-7.

REFERENCES FOR SUPPLEMENTAL METHODS AND RESULTS

[87]. ACOG Committee on Practice Bulletins-Obstetrics (2007) ACOG Practice Bulletin No. 80: premature rupture of membranes. Clinical management guidelines for obstetrician-gynecologists. Obstet Gynecol 109: 1007-1019.

[88]. Buhimschi C S, Bhandari V, Hamar B D, et al. (2007) Proteomic profiling of the amniotic fluid to detect inflammation, infection, and neonatal sepsis. PLoS Med 4: e18.

[89]. Naef R W 3rd, Allbert J R, Ross E L, Weber B M, Martin R W, et al. (1998) Premature rupture of membranes at 34 to 37 weeks' gestation: aggressive versus conservative management. Am J Obstet Gynecol 178: 126-130.

[90]. Edwards R K, Clark P, Locksmith Gregory J, Duff P (2001) Performance characteristics of putative tests for subclinical chorioamnionitis. Infect Dis Obstet Gynecol 9: 209-214.

[91]. Garry D, Figueroa R, Aguero-Rosenfeld M, Martinez E, Visintainer P, et al. (1996) A comparison of rapid amniotic fluid markers in the prediction of microbial invasion of the uterine cavity and preterm delivery. Am J Obstet Gynecol 175: 1336-1341.

[92]. Naeye R L. Disorders of the placenta and decidua. (1992) In: Disorder of the Placenta, Fetus and Neonate: Diagnosis and Clinical Significance. St. Louis: Mosby, pp. 118-247.

[93]. Salafia C M, Weigl C, Silberman L (1989) The prevalence and distribution of acute placental inflammation in uncomplicated term pregnancies. Obstet Gynecol 73: 383-389.

[94]. Buhimschi C S, Buhimschi I A, Abdel-Razeq S., Rosenberg V A, Thung S F, et al. (2007) Proteomic biomarkers of intra-amniotic inflammation: relationship with funisitis and early-onset sepsis in the premature neonate. Pediatr Res 61: 318-324.

[95]. McCrea H J, Ment L R (2008) The diagnosis, management, and postnatal prevention of intraventricular hemorrhage in the preterm neonate. Clin Perinatol 35: 777-792.

[96]. An international classification of retinopathy of prematurity (1984) The Committee for the Classification of Retinopathy of Prematurity Arch Ophthalmol 102: 1130-1134.

[97]. Uauy R D, Fanaroff A A, Korones S B, Phillips E A, Phillips J B, et al. (1991) Necrotizing enterocolitis in very low birth weight infants: biodemographic and clinical correlates. National Institute of Child Health and Human Development Neonatal Research Network. J Pediatr 119: 630-638.

[98]. Bhandari A, Bhandari V (2009) Pitfalls, problems, and progress in bronchopulmonary dysplasia. Pediatrics 123: 1562-1573.

99. Ramström M, Hagman C, Mitchell J K, Derrick P J, Håkansson P, et al. (2005) Depletion of high-abundant proteins in body fluids prior to liquid chromatography fourier transform ion cyclotron resonance mass spectrometry. J Proteome Res 4: 410-416.

100. Shifman M A, Li Y, Colangelo C M, Stone K L, Wu T L, et al. (2007) YPED: a web-accessible database system for protein expression analysis. J Proteome Res 6: 4019-4024.

101. Nyman M (1959) Serum haptoglobin. Methodical and clinical studies. Scand J Clin Lab Invest 11 (Supp 39): 1-169.

[102]. Kalayci A G Yilmazer F, Adam B, Sancak R, Küçüködüks (2000) The importance of fibronectin, haptoglobin, ceruloplasmin and transferrin in the early diagnosis of neonatal sepsis. Turk J Med Sci 30: 151-155.

The invention claimed is:
1. A method of diagnosing, aiding in diagnosing or predicting risk of developing early onset neonatal sepsis (EONS) in a newborn subject, comprising:
(a) determining if switching of an Hp 0-0 phenotype to an Hp 1-1, an Hp 2-2 or an Hp 1-2 phenotype has occurred in the newborn subject; and
(b) diagnosing or aiding in diagnosing the newborn subject as having EONS, or predicting that the newborn subject is at increased risk of developing EONS, if switching of an Hp 0-0 phenotype to an Hp 1-1, an Hp 2-2 or an Hp 1-2 phenotype has occurred.
2. The method of claim 1, wherein the biological sample is a blood sample.
3. The method of claim 2, wherein the blood sample is an umbilical cord blood sample.
4. The method of claim 3, wherein the umbilical cord blood sample is an umbilical cord blood serum sample.
5. The method of claim 1, wherein the biological sample is a decidua sample or a placental sample.
6. The method of claim 1, wherein the biological sample is provided within 24 hours, within 48 hours, or within 72 hours after birth of the newborn subject.
7. The method of claim 1, further comprising assessing the likelihood that the newborn subject will develop intraventricular haemorrhage (IVH), retinopathy of prematurity (ROP), necrotizing enterocolitis (NEC) or bronchopulmonary dysplasia (BPD) if the newborn subject is diagnosed with EONS.
8. The method of claim 1, wherein the newborn subject is a preterm birth (PTB) newborn subject.

* * * * *